(12) United States Patent
Sisk et al.

(10) Patent No.: US 9,328,086 B2
(45) Date of Patent: *May 3, 2016

(54) SUBSTITUTED BIPYRIDINES FOR USE IN ORGANIC LIGHT-EMITTING DEVICES

(75) Inventors: David T. Sisk, San Diego, CA (US); Sazzadur Rahman Khan, San Diego, CA (US); Amane Mochizuki, San Diego, CA (US)

(73) Assignee: NITTO DENKO CORPORATION, Osaka (JP)

( * ) Notice: Subject to any disclaimer, the term of this patent is extended or adjusted under 35 U.S.C. 154(b) by 748 days.

This patent is subject to a terminal disclaimer.

(21) Appl. No.: 13/232,837

(22) Filed: Sep. 14, 2011

(65) Prior Publication Data

US 2012/0179089 A1    Jul. 12, 2012

Related U.S. Application Data

(60) Provisional application No. 61/383,602, filed on Sep. 16, 2010.

(51) Int. Cl.
*C07D 401/04* (2006.01)
*C09K 11/06* (2006.01)
(Continued)

(52) U.S. Cl.
CPC ............ *C07D 401/04* (2013.01); *C07D 401/14* (2013.01); *C07D 413/14* (2013.01);
(Continued)

(58) Field of Classification Search
CPC .. C07D 401/04; C07D 413/14; C07D 417/14; C07D 401/14; H01L 51/5048; H01L 51/0085; H01L 51/0072; H01L 51/0077; H01L 51/5092; H01L 51/0061; H01L 51/5012
USPC .......................................... 546/257; 514/334
See application file for complete search history.

(56) References Cited

U.S. PATENT DOCUMENTS 5,766,779 A    6/1998  Shi et al.
6,541,490 B1   4/2003  Campbell et al.
(Continued)

FOREIGN PATENT DOCUMENTS

CN    101 219 989    7/2008
EP      0 825 803    2/1998
(Continued)

OTHER PUBLICATIONS

Soler; Photochemistry and Photobiology, 2000, 71, 724-729.*
(Continued)

*Primary Examiner* — Janet L Andres
*Assistant Examiner* — Daniel Carcanague
(74) *Attorney, Agent, or Firm* — Knobbe, Martens, Olson & Bear, LLP

(57) ABSTRACT

Optionally substituted bipyridine compounds, optionally substituted phenylbipyridine compounds, or optionally substituted bis-phenylbipyridine compounds may be useful in light-emitting devices. Some examples include, but are not limited to, optionally substituted 4-(5-(6-(4-(diphenylamino) phenyl)pyridin-3-yl)pyridin-2-yl)-N,N-diphenylbenzenamine, optionally substituted 9-(4-(5-(6-(4-(9H-carbazol-9-yl)phenyl)pyridin-3-yl)pyridin-2-yl)phenyl)-9H-carbazole, optionally substituted 4-(5-(6-(benzo[d]thiazol-2-yl)pyridin-3-yl)pyridin-2-yl)-N,N-diphenylbenzenamine, optionally substituted 4-(5-(6-(benzo[d]oxazol-2-yl)pyridin-3-yl)pyridin-2-yl)-N,N-diphenylbenzenamine, optionally substituted N,N-diphenyl-4-(5-(6-(1-phenyl-1H-benzo[d]imidazol-2-yl)pyridin-3-yl)pyridin-2-yl)benzenamine, optionally substituted 4-(5-(6-(4-(9H-carbazol-9-yl)phenyl)pyridin-3-yl)pyridin-2-yl)-N,N-diphenylbenzenamine, optionally substituted 2-(5-(6-(benzo[d]thiazol-2-yl)pyridin-3-yl)pyridin-2-yl)benzo[d]thiazole, optionally substituted 2-(5-(6-(benzo[d]thiazol-2-yl)pyridin-3-yl)pyridin-2-yl)benzo[d]oxazole, optionally substituted 9-(4-(5-(6-(benzo[d]thiazol-2-yl)pyridin-3-yl)pyridin-2-yl)phenyl)-9H-carbazole, optionally substituted 9-(4-(5-(6-(benzo[d]oxazol-2-yl)pyridin-3-yl)pyridin-2-yl)phenyl)-9H-carbazole, optionally substituted 9-(4-(6'-(1-phenyl-1H-benzo[d]imidazol-2-yl)-3,3'-bipyridin-6-yl)phenyl)-9H-carbazole, and 6,6'-bis(9-phenyl-9H-carbazol-3-yl)-3,3'-bipyridine.

38 Claims, 6 Drawing Sheets

(51) Int. Cl.

| | |
|---|---|
| A61N 5/06 | (2006.01) |
| C07D 417/14 | (2006.01) |
| C07D 413/14 | (2006.01) |
| C07D 401/14 | (2006.01) |
| A61M 37/00 | (2006.01) |
| H01L 51/54 | (2006.01) |
| H01L 51/00 | (2006.01) |
| H01L 51/50 | (2006.01) |

(52) U.S. Cl.
CPC .......... *C07D417/14* (2013.01); *H01L 51/0061* (2013.01); *H01L 51/0072* (2013.01); *H01L 51/0077* (2013.01); *H01L 51/0085* (2013.01); *H01L 51/5012* (2013.01); *H01L 51/5048* (2013.01); *H01L 51/5092* (2013.01)

(56) References Cited

U.S. PATENT DOCUMENTS

| | | |
|---|---|---|
| 6,723,445 B2 | 4/2004 | Li et al. |
| 6,916,555 B2 * | 7/2005 | Suzuki et al. .................. 428/690 |
| 7,579,353 B2 | 8/2009 | Fiandor Roman et al. |
| 8,003,229 B2 | 8/2011 | Sisk et al. |
| 8,057,921 B2 | 11/2011 | Sisk et al. |
| 8,062,770 B2 | 11/2011 | Sisk et al. |
| 8,062,771 B2 | 11/2011 | Sisk et al. |
| 8,062,772 B2 | 11/2011 | Sisk et al. |
| 8,062,773 B2 | 11/2011 | Sisk et al. |
| 8,263,238 B2 | 9/2012 | Sisk et al. |
| 8,585,926 B2 * | 11/2013 | Zheng ...................... 252/301.16 |
| 8,952,364 B2 * | 2/2015 | Lai et al. .......... 257/40 |
| 2002/0024293 A1 | 2/2002 | Igarashi et al. |
| 2002/0034656 A1 | 3/2002 | Thompson et al. |
| 2003/0072964 A1 | 4/2003 | Kwong et al. |
| 2003/0124381 A1 | 7/2003 | Thompson et al. |
| 2003/0234608 A1 | 12/2003 | Lee et al. |
| 2004/0024293 A1 | 2/2004 | Lawrence et al. |
| 2005/0127823 A1 | 6/2005 | Iwakuma et al. |
| 2005/0282036 A1 | 12/2005 | D'Andrade et al. |
| 2006/0222886 A1 | 10/2006 | Kwong et al. |
| 2007/0015006 A1 | 1/2007 | Lee et al. |
| 2007/0075631 A1 | 4/2007 | Tung et al. |
| 2007/0129613 A1 | 6/2007 | Rochester et al. |
| 2008/0166591 A1 | 7/2008 | Yamada et al. |
| 2009/0000658 A1 | 1/2009 | Zakeeruddin et al. |
| 2009/0021146 A1 * | 1/2009 | Iida et al. ...................... 313/504 |
| 2009/0134783 A1 | 5/2009 | Lin et al. |
| 2009/0214921 A1 | 8/2009 | Uensal et al. |
| 2009/0306385 A1 | 12/2009 | Walters et al. |
| 2010/0060154 A1 | 3/2010 | Nomura et al. |
| 2011/0196158 A1 * | 8/2011 | Zheng ........................... 546/256 |
| 2011/0306922 A1 * | 12/2011 | Khan et al. ...................... 604/20 |
| 2012/0037900 A1 | 2/2012 | Sisk et al. |
| 2012/0223635 A1 * | 9/2012 | Mochizuki et al. ........... 313/512 |
| 2013/0069044 A1 * | 3/2013 | Ma .................. 257/40 |
| 2013/0075706 A1 * | 3/2013 | Zheng et al. ..................... 257/40 |
| 2013/0140534 A1 * | 6/2013 | Lai et al. .......................... 257/40 |
| 2014/0014883 A1 * | 1/2014 | Zheng ........................... 252/500 |
| 2014/0066627 A1 * | 3/2014 | Zheng et al. .................. 546/256 |

FOREIGN PATENT DOCUMENTS

| | | |
|---|---|---|
| EP | 1 857 521 | 11/2007 |
| EP | 1 858 094 | 11/2007 |
| JP | 2000-186066 | 7/2000 |
| JP | 2002-324678 | 11/2002 |
| JP | 2004-075603 | 3/2004 |
| JP | 2004-273190 | 9/2004 |
| JP | 2007-291092 | 11/2007 |
| JP | 2008-115131 | 5/2008 |
| JP | 2008-120696 | 5/2008 |
| JP | 2008-133225 | 6/2008 |
| JP | 2008-156266 | 7/2008 |
| JP | 2008-162910 | 7/2008 |
| JP | 2008-214306 | 9/2008 |
| JP | 2008-214307 | 9/2008 |
| JP | 2009-158848 | 7/2009 |
| JP | 2009224763 | * 10/2009 |
| JP | 2010-083862 | 4/2010 |
| JP | 2010-513971 | 4/2010 |
| KR | 10-2009-0073850 | 7/2009 |
| KR | 10-2009-0073852 | 7/2009 |
| KR | 10-2010-0075079 | 7/2010 |
| WO | WO 03/078541 | 9/2003 |
| WO | WO 2004/074399 | 9/2004 |
| WO | WO 2006/080229 | 8/2006 |
| WO | WO 2006/095539 | 9/2006 |
| WO | WO 2008/027132 | 3/2008 |
| WO | WO 2009/096549 | 8/2009 |
| WO | WO 2010/076991 | 7/2010 |
| WO | WO 2010/090925 | 8/2010 |
| WO | WO 2011/156414 | 12/2011 |
| WO | WO 2012/037269 | 3/2012 |

OTHER PUBLICATIONS

Pawar; Indian Journal of Chemistry B, 1976, 14B, 375 366.*
Koene; Chem. Mater. 1998, 10, 2235-2250.*
Adachi et al., "Nearly 100% Internal Phosphorescence Efficiency in an Organic Light-Emitting Device", Journal of Applied Physics, vol. 90, Issue 10, Nov. 15, 2001, pp. 5048-5051.
Baldo et al., "High-Efficiency Fluorescent Organic Light-Emitting Devices Using a Phosphorescent Sensitizer", Nature, vol. 403, Feb. 17, 2000, pp. 750-753.
Billmeyer, et al., "Principles of Color Technology", 2nd edition, John Wiley & Sons, Inc., New York, 1981.
Cai et al., "Electron and Hole Transport in a Wide Bandgap Organic Phosphine Oxide for Blue Electrphosphorescence", Applied Physics Letters, vol. 92, Feb. 28, 2008, pp. 3.
Chen et al., "White Organic Light-Emitting Devices with a Bipolar Transport Layer Between Blue Fluorescent and Orange Phosphorescent Emitting Layers", Applied Physics Letters, vol. 91, Jul. 11, 2007, pp. 3.
Cheng et al., "White Organic Light-Emitting Devices Using a Phosphorescent Sensitizer", Applied Physics Letters, vol. 82, No. 24, Jun. 16, 2003, pp. 3.
CIE 1971, International Commission on Illumination, Colorimetry: Official Recommendations of the International Commission on Illumination, Publication CIE No. 15 (E-1.3.1) 1971, Bureau Central de la CIE, Paris, 1971.
D'Andrade et al, "Efficient Organic Electrophosphorescent White-Light-Emitting Device With a Triple Doped Emissive Layer", Advanced Materials, Apr. 5, 2004, vol. 16, Issue 7, pp. 624- 628.
D'Andrade et al., "White Light Emission Using Triplet Excimers in Electrophosphorescent Organic Light-Emitting Devices", Advanced Materials, Aug. 5, 2002, vol. 14, Issue 15, pp. 1032-1036.
D'Andrade et al., "White Organic Light-Emitting Devices for Solid-State Lighting", Advanced Materials, Sep. 16, 2004, vol. 16, Issue 18, pp. 1585-1595.
Guan et al., "The Host Materials Containing Carbazole and Oxadiazole Fragment for Red Triplet Emitter in Organic Light-Emitting Diodes", Science Direct, Organic Electronics 7, May 19, 2006, pp. 330-336.
Gustafsson et al. "Flexible Light-Emitting Diodes Made from Soluble Conducting Polymer," Nature, Jun. 11, 1992, vol. 357, pp. 477-479.
Kreimer-Birnbaum et al., "Modified Porphyrins, Chlorins, Phthalocyanines and Purpurins: Second-Generation Photosensitizers for Photodynamic Therapy", Semin Hematol, 1989, vol. 26, pp. 157-73.
Seo et al., "Highly Efficient White Organic Light-Emitting Diodes Using Two Emitting Material for Three Primary Colors (Red, Green and Blue)", Applied Physics Letters, vol. 90, May 16, 2007, pp. 3.
Spillane et al., "Benzothiazole Bipyridine Complexes of Ruthenium(II) with Cytotoxic Activity", Journal of Biological Inorganic Chemistry, 2007, vol. 12, No. 6, pp. 797-807.
Spillane et al., "Inert Benzothiazole Functionalised Ruthenium(II) Complexes; Potential DNA Hairpin Binding Agents", Dalton Transactions, 2006, vol. 25, pp. 3122-3123.

(56) References Cited

OTHER PUBLICATIONS

Spillane et al., "The Dichotomy in the DNA-Binding Behaviour of Ruthenium(II) Complexes Bearing Benzoxazole and Benzothiazole Groups", Journal of Inorganic Biochemistry, 2008, vol. 102, pp. 673-683.

Su et al., "Pyridine-Containing Bipolar Host Materials for Highly Efficient Blue Phosphorescent OLEDs", Chemical Materials, vol. 20, Feb. 12, 2008, pp. 1691-1693.

Sun et al., "Management of Singlet and Triplet Excitons for Efficient White Organic Light-Emitting Devices", Nature, Apr. 2006, vol. 440, pp. 908-912.

Wang et al., "2,5. Bis [4. (9H.9. Carbazolyl) phenyl] pyridine Synthesis and Characterization", Huaxue Shiji, 2008, vol. 30, No. 4, pp. 280-282.

Wu et al., "Highly Efficient White-Electrophosphorescent Devices Based on Polyfluorene Copolymers Containing Charge-Transporting Pendent Units", Journal of Materials Chemistry, 2007, vol. 17, pp. 167-173.

Yu et al., "Synthesis and Characterization of Poly(Benzobisoxazole)s and Poly(Benzobisthiazole)s with 2,2'-bipyridyl units in the Backbone", Macromolecules, 1998, vol. 31, No. 17, pp. 5639-5646.

International Search Report and the Written Opinion in PCT Application No. PCT/US2011/051618, dated Dec. 16, 2011.

International Preliminary Report on Patentability in PCT Application No. PCT/US2011/051618, dated Mar. 28, 2013.

Cheng et al., "[6,6'-Bis(benzimidazol-2-yl-N3)-2,2'-bipyridine]dichlorocobalt(II)-Dimethylform-amide (1/2)", Acta Crystallographica Section C, 1997, vol. C53, pp. 1238-1240.

Liu et al., "Π-Conjugated Aromatic Enynes as a Single-Emitting Component for White Electroluminescence", Journal of American Chemical Society, 2006, vol. 128, No. 17, pp. 5592-5593.

Miao et al., "Crystal Structure of bis(3,3'-bis(1-ethyl-1$H$-benzimidazol-2-yl)-2,2'-bipyridine)Copper(II) Diperchlorate Monohydrate, [Cu($C_{28}H_{24}N_6$)$_2$][$ClO_4$]$_2$ • $H_2O$", NCS 222, 2007, pp. 323-326.

Miao et al., "Synthesis and Crystal Structure of 3,3'-Bis(2-benzimidazolyl)-2,2'-dipyridine with Hydrated Zinc(II) Perchlorate", Chinese Journal of Structural Chemistry, 2007, vol. 26, No. 4, pp. 439-444.

Stibrany, Robert Timothy, "Exploration of Benzimidazole Chemistry", Thesis, Rutgers University, New Jersey, 2008, pp. 3.

Zhao et al., "Studies of Third-Order Optical Nonlinearities of Model Compounds Containing Benzothiazole, Benzimidazole, and Benzoxazole Units", Chemistry of Materials, 1990, vol. 2, pp. 670-678.

\* cited by examiner

1mM ALA + 30J/cm2

No ALA + 30J/cm2

SUBSTITUTED BIPYRIDINES FOR USE IN ORGANIC LIGHT-EMITTING DEVICES

CROSS-REFERENCE TO RELATED APPLICATIONS

This application claims the benefit of U.S. Provisional Application No. 61/383,602, filed Sep. 16, 2010, which is incorporated by reference herein in its entirety.

BACKGROUND OF THE INVENTION

1. Field

The embodiments relate to compounds such as substituted biaryl ring systems for use in light-emitting devices.

2. Description of the Related Art

Organic light-emitting devices (OLEDs) have been widely developed for flat panel displays and are rapidly moving toward solid state lighting (SSL) applications. Such lighting applications include not only general lighting that may require primarily white color, but also special purpose lighting, such as photo-dynamic therapy application, that may require mono-color. In order to reduce the driving voltage of an OLED device and extend its operational lifetime, it may be helpful to develop new high performance host materials.

SUMMARY OF THE INVENTION

Some optionally substituted linear aryl ring systems are useful in light-emitting devices. For example, optionally substituted bipyridine compounds, optionally substituted phenylbipyridine compounds, or optionally substituted bis-phenylbipyridine compounds may be useful in light-emitting devices. For example, these compounds may comprise at least an optionally substituted aryl amine or an optionally substituted heteroaryl comprising a ring nitrogen as terminal rings of the linear ring system.

For example, some embodiments relate to a compound represented by Formula 1:

$$Hcy^1-(Ph)_n-Py-(Ph)_m-Hcy^2 \quad \text{(Formula 1)}$$

wherein Py may be optionally substituted 3,3'-bipyrindindiyl; each Ph may be independently optionally substituted phenyl; n and m are independently 0, 1, or 2; $Hcy^1$ and $Hcy^2$ are independently optionally substituted carbazolyl, optionally substituted diphenylamine, optionally substituted benzimidazolyl, optionally substituted benzothiazolyl and optionally substituted benzoxazolyl. Preferably, each $Hcy^1$ and $Hcy^2$ can be attached to the optionally substituted 3,3'-bipyrindindiyl or the optionally substituted phenyl, if present, at the para-position.

Some embodiments provide an organic light-emitting diode device comprising an organic component. The organic component may comprise a light-emitting component and a compound described herein. In some embodiments, the organic light-emitting diode further comprises: a cathode and an anode, wherein the organic component may be disposed between the anode and the cathode. In some embodiments the device is configured to emit light of a wavelength that can activate at least a portion of a photosensitive compound which has been administered to a tissue of a mammal. In some embodiments the device further comprises a dosage component configured to provide a sufficient amount of light to activate a sufficient portion of the photosensitive compound to provide a therapeutic effect for treating a disease.

Some embodiments relate to a composition comprising a compound described herein and a fluorescent compound or a phosphorescent compound.

Some embodiments relate to a composition comprising at least 10%, at least 20%, at least 50%, at least 80%, at least 90%, or at least 95%, up to about 100% by weight of a compound described herein.

In some embodiments, these devices may be used in a method of carrying out phototherapy comprising: exposing at least a portion of a tissue of a mammal to light from a device described herein. In some embodiments, the tissue comprises a photosensitive compound which is not naturally in the tissue, and at least a portion of the photosensitive compound is activated by exposing the portion of the tissue to light from the device.

Some embodiments provide a method of treating a disease, comprising: administering a photosensitive compound to a tissue of a mammal in need thereof; exposing at least a portion of the tissue to light from a device described herein; and wherein at least a portion of the photosensitive compound is activated by at least a portion of the light from the device to which the tissue is exposed, to thereby treat the disease.

Some embodiments provide a phototherapy system comprising: a device described herein; and a photosensitive compound; wherein the photosensitive compound is suitable for administration to a tissue of a mammal in need of phototherapy; and wherein the device is configured to emit light of a wavelength which can activate at least a portion of the photosensitive compound when it is in the tissue.

These and other embodiments are described in greater detail herein.

DETAILED DESCRIPTION OF THE PREFERRED EMBODIMENT

Figure 3:
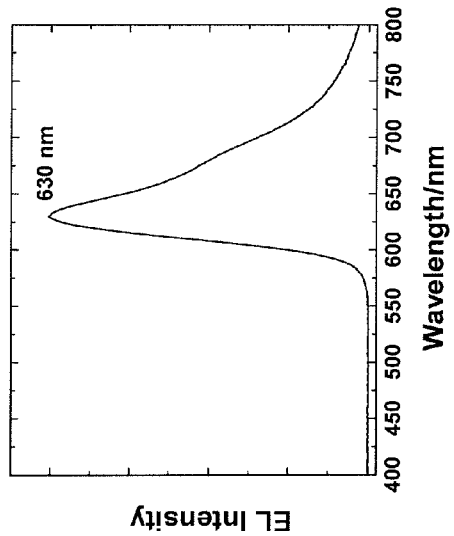
FIG. 3 is the electroluminescence spectrum of one embodiment of a light emitting device.

Unless otherwise indicated, when a chemical structural feature such as phenyl is referred to as being "optionally substituted," it includes a feature which may have no substituents (i.e. may be unsubstituted), or which may have one or more substituents. A feature that is "substituted" has one or more substituents. The term "substituent" has the ordinary meaning known to one of ordinary skill in the art. In some embodiments, the substituent includes an ordinary organic moiety known in the art, which may have a molecular weight (e.g. the sum of the atomic masses of the atoms of the substituent) of less than: about 500 g/mol, about 300 g/mol, about 200 g/mol, about 100 g/mol, or about 50 g/mol. In some embodiments, the substituent comprises: 0-30, 0-20, 0-10, or 0-5 carbon atoms; and 0-30, 0-20, 0-10, or 0-5 heteroatoms independently selected from: N, O, S, P, Si, F, Cl, Br, I, and combinations thereof; provided that the substituent comprises at least one atom selected from: C, N, O, S, P, Si, F, Cl, Br, and I. Examples of substituents include, but are not limited to, alkyl, alkenyl, alkynyl, heteroalkyl, heteroalkenyl, heteroalkynyl, aryl, heteroaryl, carbazolyl, arylalkyl, heteroarylalkyl, arylheteroalkyl, heteroarylheteroalkyl, hydroxy, protected hydroxy, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, and amino, including mono- and di-substituted amino groups, and the protected derivatives thereof. Some substituents, including alkyl, alkenyl, alkynyl, aryl, heteroaryl, etc., may themselves be further substituted with any substituent described above. In some embodiments, a substituent of a substituent may exclude a like group, such as a phenyl substituent of phenyl or an alkyl substituent of alkyl. In some embodiments, the substituent and any further substituents of the substituent may have a molecular weight (e.g. the sum of the atomic masses of the atoms of the substituent and its further substituents) of less than: about 500 g/mol, about 300 g/mol, about 200 g/mol, about 100 g/mol, or about 50 g/mol. In some embodiments, the substituent and any further substituents of the substituent may comprise: 2-30, 2-20, 2-10, or 2-5 carbon atoms; and 0-30, 0-20, 0-10, or 0-5 heteroatoms independently selected from: N, O, S, P, Si, F, Cl, Br, I, and combinations thereof.

Substituents may also be represented structurally to include, but not be limited to, —X—$R^b$, —$R^d$, —$R^a$—$R^c$, and —$R^a$—X—$R^c$, wherein:

$R^a$ may be optionally substituted hydrocarbyl, including optionally substituted alkyl, (such as optionally substituted linear alkyl, optionally substituted branched alkyl, optionally substituted cycloalkyl, etc.), optionally substituted alkenyl, (such as optionally substituted linear alkenyl, optionally substituted branched alkenyl, optionally substituted cycloalkenyl, etc.), optionally substituted alkynyl (such as optionally substituted linear alkynyl, optionally substituted branched alkynyl, optionally substituted cycloalkynyl, etc.), optionally substituted aryl, (such as optionally substituted phenyl, optionally substituted naphthyl, etc.) and the like; an optionally substituted heterocycle, such as optionally substituted heteroaryl (such as optionally substituted pyridinyl, optionally substituted thienyl, optionally substituted furyl, optionally substituted oxazolyl, optionally substituted thiazolyl, optionally substituted imidazolyl, optionally substituted benzothienyl, optionally substituted benzofuryl, optionally substituted benzoimidazole, optionally substituted benzothiazole, optionally substituted benzoxazole, optionally substituted quinolinyl, optionally substituted carbazolyl, etc.), an optionally substituted non-aromatic heterocycle (such as optionally substituted tetrahydrofuranyl, optionally substituted pyrrolidinyl, optionally substituted piperidinyl, optionally substituted dihydropyrrolyl, etc.), etc; and haloalkyl, including fluoroalkyl, perfluoroalkyl, chloralkyl, bromoalkyl, iodoalkyl, etc.;

$R^b$ and $R^c$ may independently be H or $R^a$;

$R^d$ may independently be $R^a$; halo; including F, Cl, Br, I; —CN; —CNO; —OCN; and —$NO_2$; and X may be O, S, —$NR^b$, —$X^1$—, —$X^a$—$X^1$—, —$X^1$—$X^b$—, or —$X^a$—$X^1$—$X^b$—, wherein $X^1$ may be CO or $SO_2$, and $X^a$ and $X^b$ may independently be O, S, or $NR^b$.

In some embodiments, $R^a$ may have 1-10, 1-6, or 1-3 carbon atoms, and $R^b$, $R^c$, and $R^d$ may have 0-10, 0-6, or 0-3 carbon atoms. In some embodiments, substituents may be selected from F, Cl, Br, I, —$CY_3$, $NO_2$, —CN, —CNO, —NCO, $R^b$, —$OR^b$, —$CO_2R^b$, —$OCOR^b$, —$NR^bCOR^c$, $CONR^bR^c$, —$NR^bR^c$, wherein each $R^b$ and $R^c$ may independently be H, optionally substituted phenyl, optionally substituted $C_{1-12}$ alkyl, or optionally substituted $C_{1-6}$ alkyl, and Y may be Cl, Br or I.

As used herein the term "aryl" has the ordinary meaning understood by a person of ordinary skill in the art, and may include an aromatic ring or aromatic ring system such as phenyl, naphthyl, etc.

As used herein, the term "alkyl" has the ordinary meaning understood by a person of ordinary skill in the art, and may include a moiety composed of carbon and hydrogen containing no double or triple bonds. Alkyl may be linear, branched, cyclic, or a combination thereof, and in some embodiments, may contain from one to thirty-five carbon atoms. Examples of alkyl groups include but are not limited to $CH_3$ (e.g. methyl), $C_2H_5$ (e.g. ethyl), $C_3H_7$ (e.g. propyl isomers such as propyl, isopropyl, etc.), $C_3H_6$ (e.g. cyclopropyl), $C_4H_9$ (e.g. butyl isomers) $C_4H_8$ (e.g. cyclobutyl isomers such as cyclobutyl, methylcyclopropyl, etc.), $C_5H_{11}$ (e.g. pentyl isomers), $C_5H_{10}$ (e.g. cyclopentyl isomers such as cyclopentyl, methylcyclobutyl, dimethylcyclopropyl, etc.) $C_6H_{13}$ (e.g. hexyl isomers), $C_6H_{12}$ (e.g. cyclohexyl isomers), $C_7H_{15}$ (e.g. heptyl isomers), $C_7H_{14}$ (e.g. cycloheptyl isomers), $C_8H_{17}$ (e.g. octyl isomers), $C_8H_{16}$ (e.g. cyclooctyl isomers), $C_9H_{19}$ (e.g. nonyl isomers), $C_9H_{18}$ (e.g. cyclononyl isomers), $C_{10}H_{21}$ (e.g. decyl isomers), $C_{10}H_{20}$ (e.g. cyclodecyl isomers), $C_{11}H_{23}$ (e.g. undecyl isomers), $C_{11}H_{22}$ (e.g. cycloundecyl isomers), $C_{12}H_{25}$ (e.g. dodecyl isomers), $C_{12}H_{24}$ (e.g. cyclododecyl isomers), $C_{13}H_{27}$ (e.g. tridecyl isomers), $C_{13}H_{26}$ (e.g. cyclotridecyl isomers), and the like.

An expression such as "$C_{1-12}$" (e.g. "$C_{1-12}$ alkyl") refers to the number of carbon atoms in a moiety, and similar expressions have similar meanings. Unless explicitly stated otherwise, expressions of this kind refer only to the parent alkyl moiety and do not limit any substituent which may be present.

As used herein, the term "haloalkyl" includes alkyl having one or more halo substituents (such as F, Cl, Br, or I). The term "fluoroalkyl" includes alkyl having one or more fluoro substituents. The term "perfluoroalkyl" includes fluoroalkyl wherein all hydrogen atom are replaced by fluoro such as —$CF_3$, —$C_2F_5$, —$C_3F_7$, —$C_4F_9$, etc.

The structures associated with some of the chemical names of compounds or moieties referred to herein are depicted below. These structures may be unsubstituted, as shown below, or a substituent may independently be in any position normally occupied by a hydrogen atom when the compound or moiety is unsubstituted.

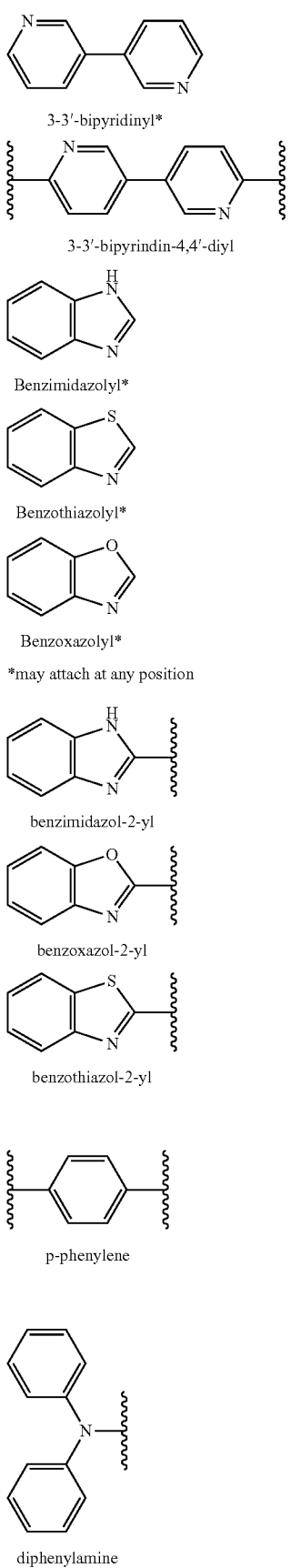
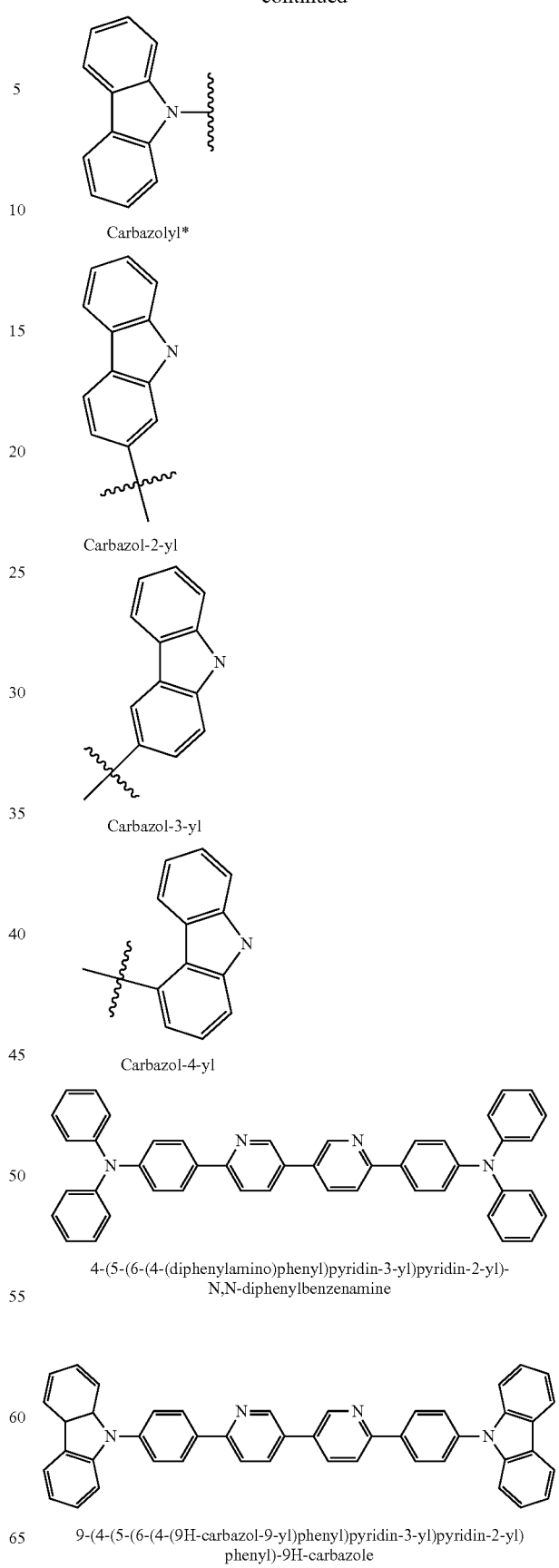

-continued

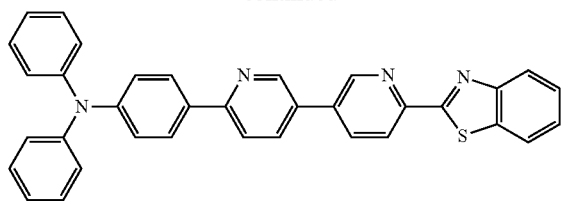

4-(5-(6-(benzo[d]thiazol-2-yl)pyridin-3-yl)pyridin-2-yl)-
N,N-diphenylbenzenamine

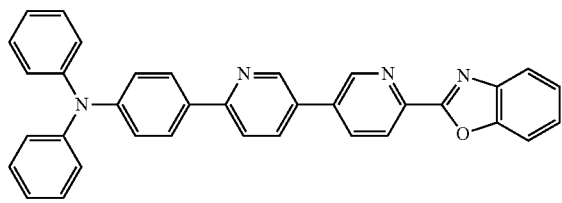

4-(5-(6-(benzo[d]oxazol-2-yl)pyridin-3-yl)pyridin-2-yl)-N,
N-diphenylbenzenamine

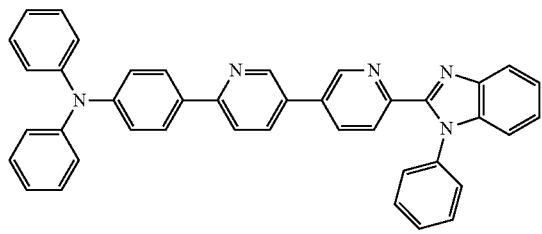

N,N-diphenyl-4-(5-(6-(1-phenyl-1H-benzo[d]imidazol-2-yl)pyridin-
3-yl)pyridin-2-yl)benzenamine

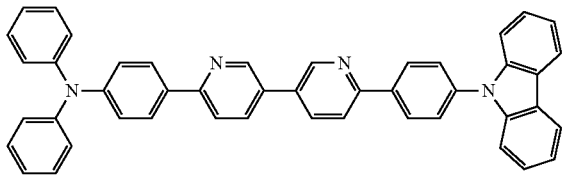

4-(5-(6-(4-(9H-carbazol-9-yl)phenyl)pyridin-3-yl)pyridin-2-yl)-N,
N-diphenylbenzenamine

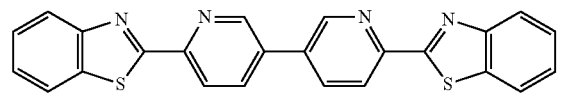

2-(5-(6-(benzo[d]thiazol-2-yl)pyridin-3-yl)pyridin-2-yl)benzo[d]thiazole

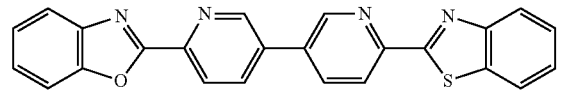

2-(5-6-(benzo[d]thiazol-2-yl)pyridin-3-yl)pyridin-2-yl)benzo[d]oxazole

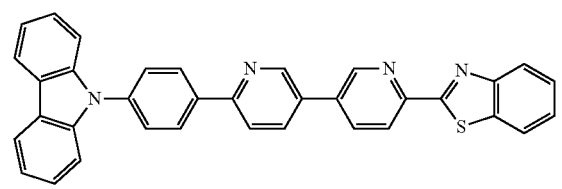

9-(4-(5-(6-(benzo[d]thiazol-2-yl)pyridin-3-yl)pyridin-2-yl)
phenyl)-9H-carbazole

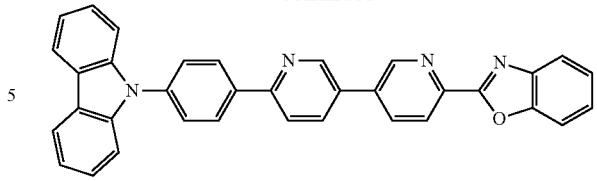

9-(4-(5-(6-(benzo[d]oxazol-2-yl)pyridin-3-yl)pyridin-2-yl)phenyl)-
9H-carbazole

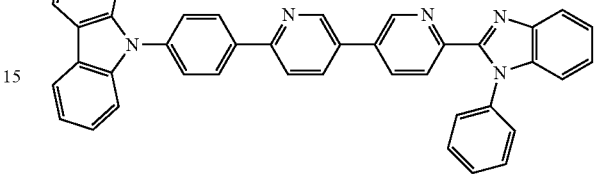

9-(4-(5-(6-(1-phenyl-1H-benzo[d]imidazol-2-yl)pyridin-3-yl)
pyridin-2-yl)phenyl)-9H-carbazole

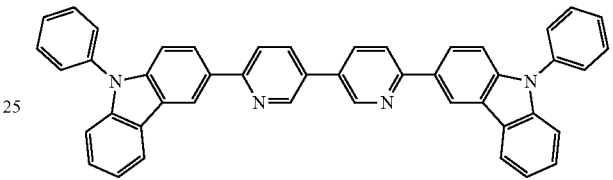

6,6'-bis(9-phenyl-9H-carbazol-3-yl)-3,3'-bipyridine

The term "low work function" has the ordinary meaning known to one of ordinary skill in the art, and may include a measure of the minimum energy required to extract an electron from the surface of the metal.

The term "high work function" has the ordinary meaning known to one of ordinary skill in the art, and may include a metal or alloy that easily injects holes and typically has a work function greater than or equal to about 4.5.

The term "low work function metal" has the ordinary meaning known to one of ordinary skill in the art, and may include a metal or alloy that easily loses electrons and typically has a work function less than about 4.3.

The expression "white light-emitting" has the ordinary meaning known to one of ordinary skill in the art, and may include a material that emits white light. In some embodiments, white light may have the approximate CIE color coordinates (X=⅓, Y=⅓). The CIE color coordinates (X=⅓, Y=⅓) may be referred to as the achromatic point. The X and Y color coordinates may be weights applied to the CIE primaries to match a color. A more detailed description of these terms may be found in CIE 1971, International Commission on Illumination, Colorimetry: Official Recommendations of the International Commission on Illumination, Publication CIE No. 15 (E-1.3.1) 1971, Bureau Central de la CIE, Paris, 1971 and in F. W. Billmeyer, Jr., M. Saltzman, Principles of Color Technology, 2nd edition, John Wiley & Sons, Inc., New York, 1981, both of which are hereby incorporated by reference in their entireties. The color rendering index (CRI) refers to the ability to render various colors and may have values ranging from 0 to 100, with 100 being the best.

Some embodiments relate to compounds represented by at least one of Formula 2, Formula 3, Formula 4, Formula 5, Formula 6, Formula 7, Formula 8, Formula 9, Formula 10, Formula 11, Formula 12, Formula 13, Formula 14, Formula 15, Formula 16, Formula 17, Formula 18, Formula 19, Formula 20, Formula 21, Formula 22, Formula 23, Formula 24, Formula 25, Formula 26, Formula 27, Formula 28, Formula 29, and/or Formula 30.

Formula 2
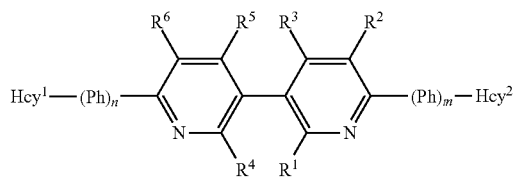
Formula 3
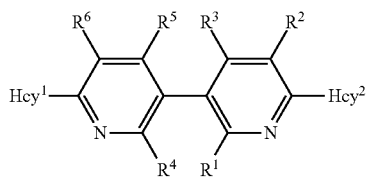
Formula 4
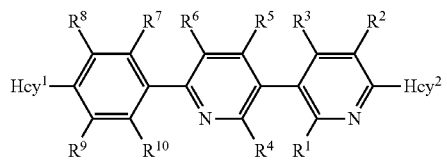
Formula 5
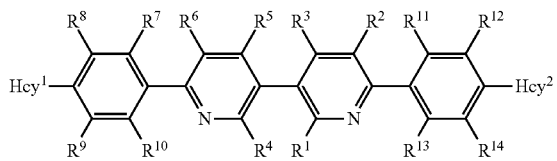
Formula 6
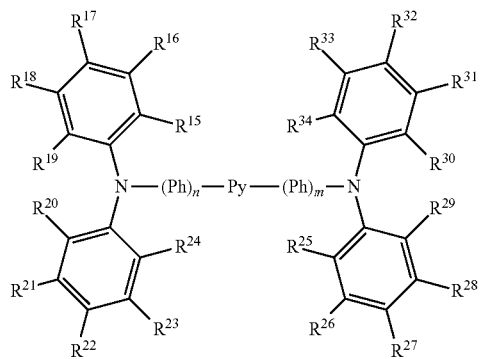
Formula 7
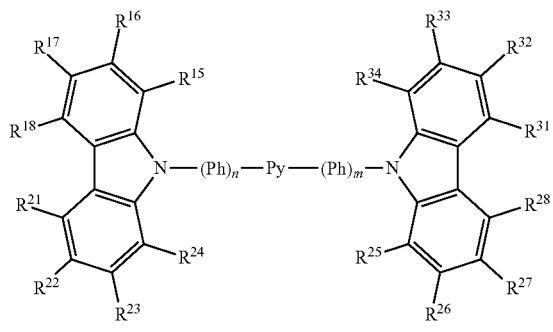
Formula 8
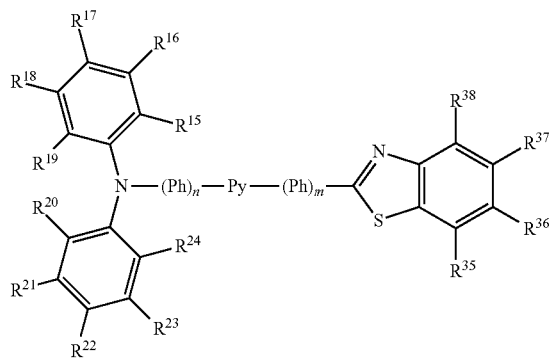
Formula 9
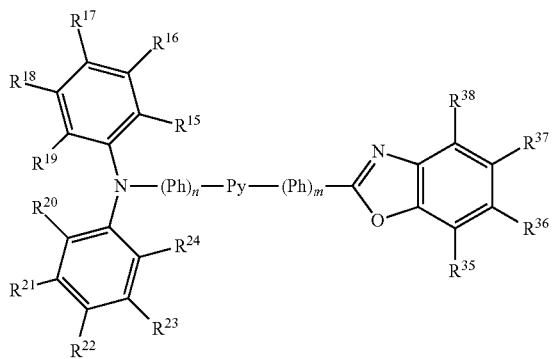
Formula 10
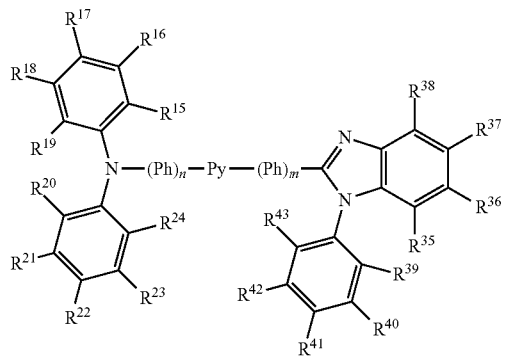
Formula 11
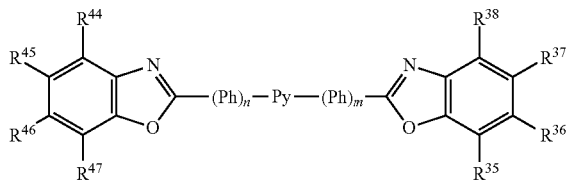

Formula 12
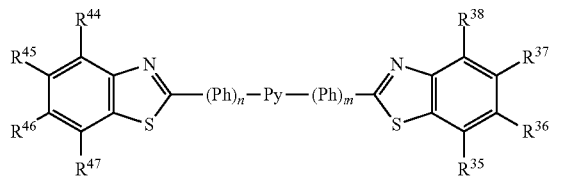
Formula 13
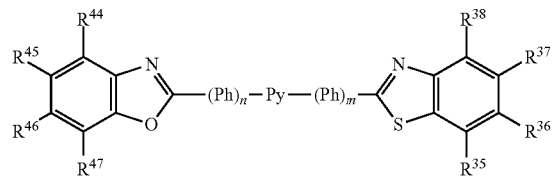
Formula 14
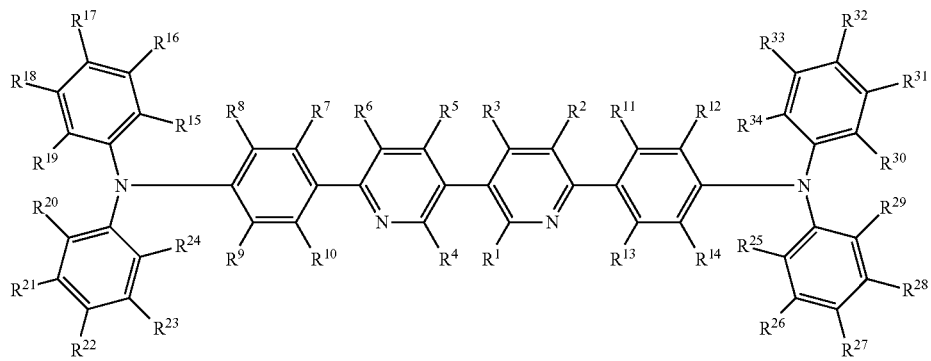
Formula 15
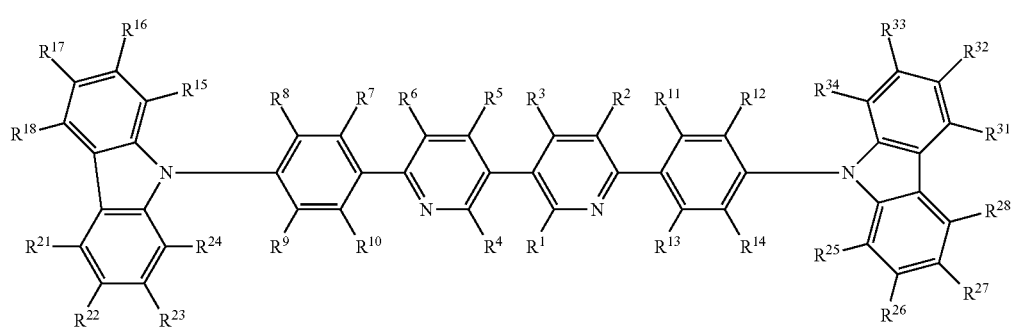
Formula 16
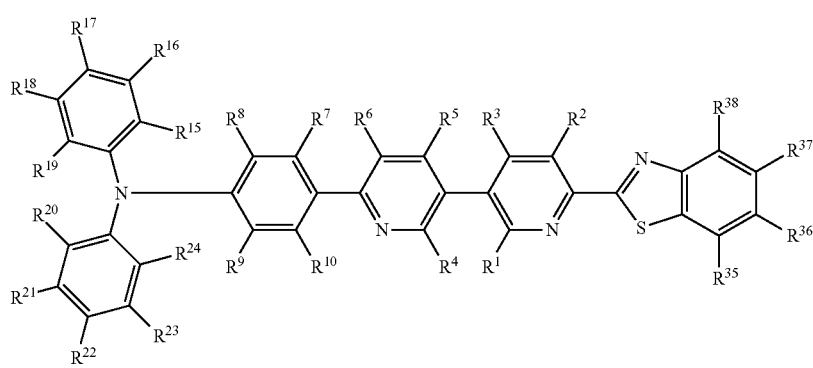
Formula 17
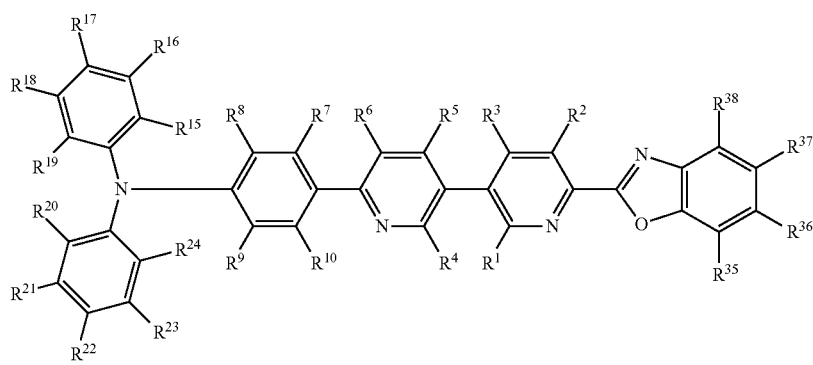

-continued
Formula 18
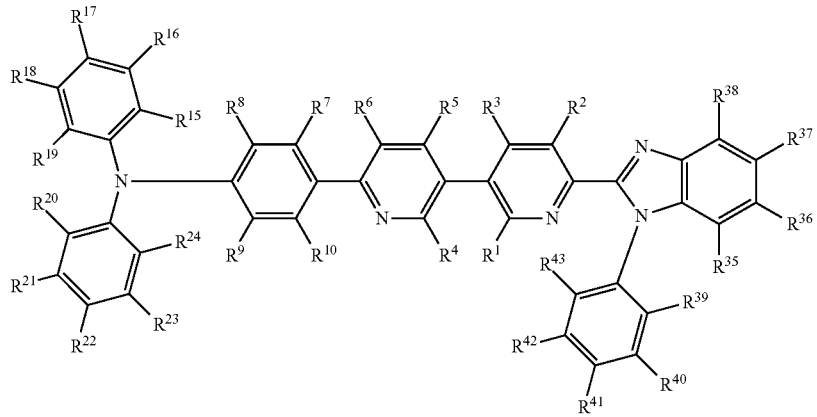
Formula 19
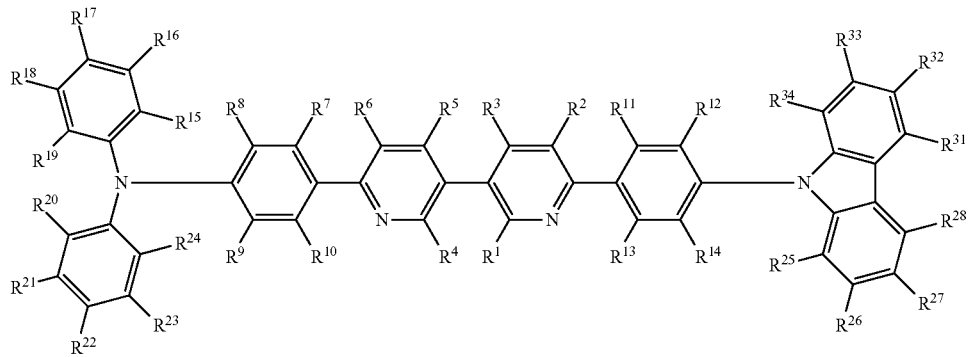
Formula 20
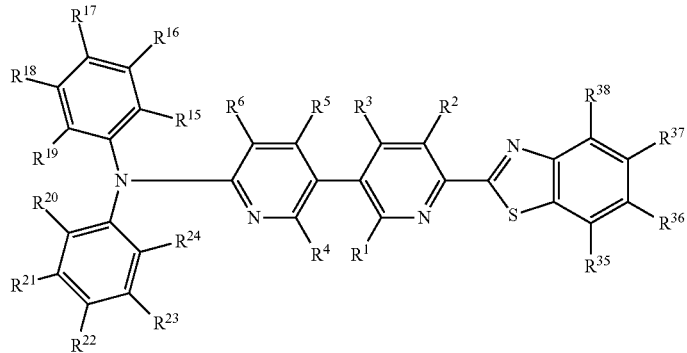
Formula 21
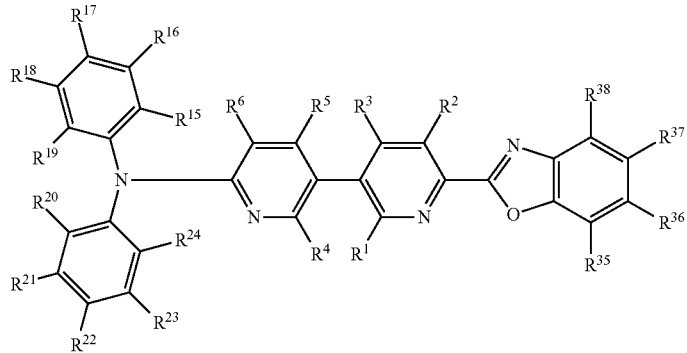

Formula 22
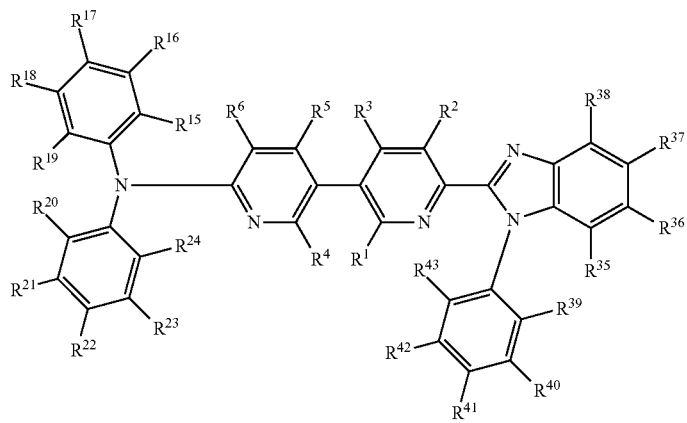
Formula 23
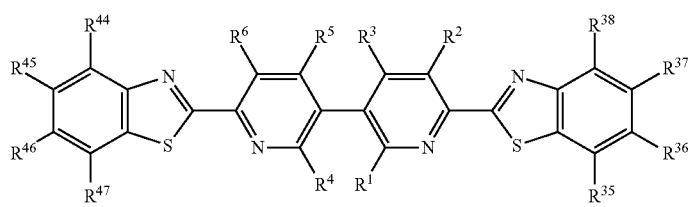
Formula 24
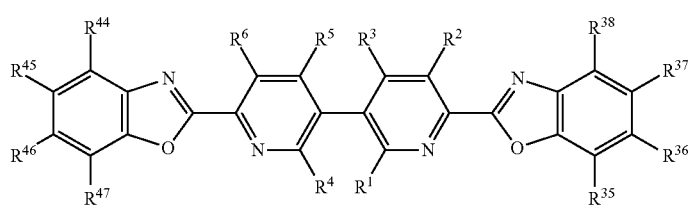
Formula 25
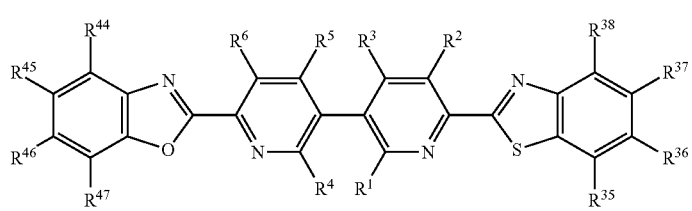
Formula 26
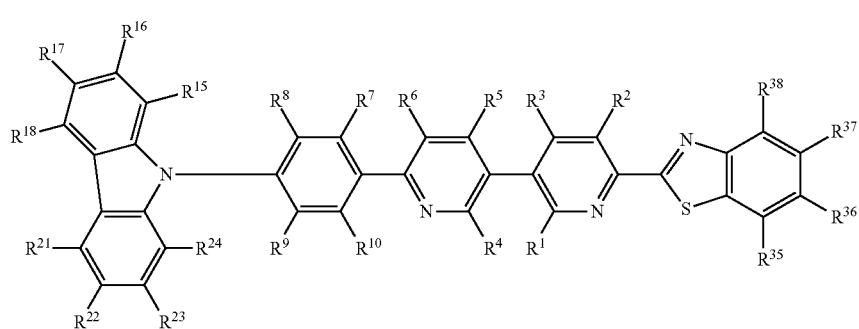

-continued

Formula 27

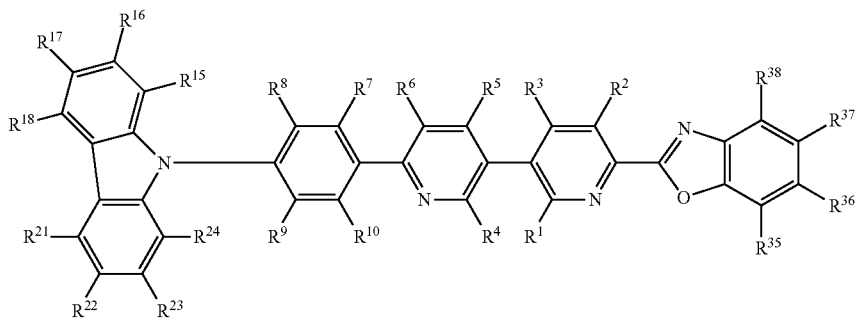

Formula 28

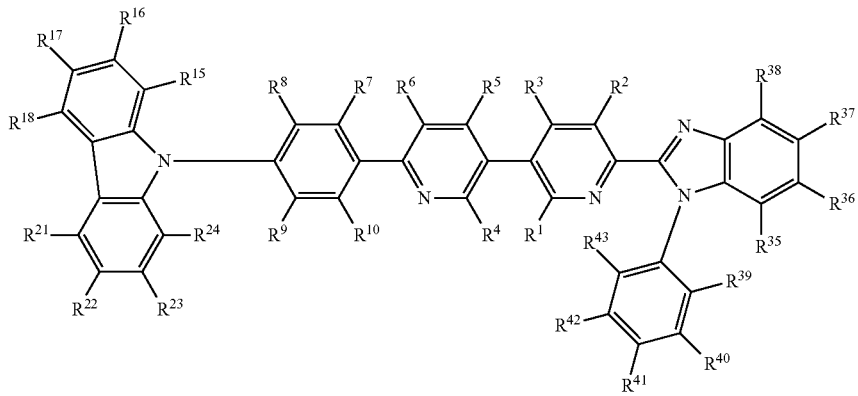

Formula 29

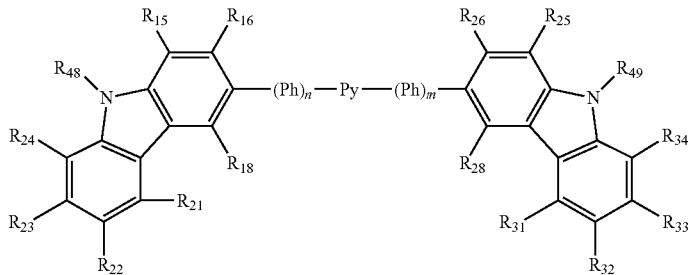

Formula 30

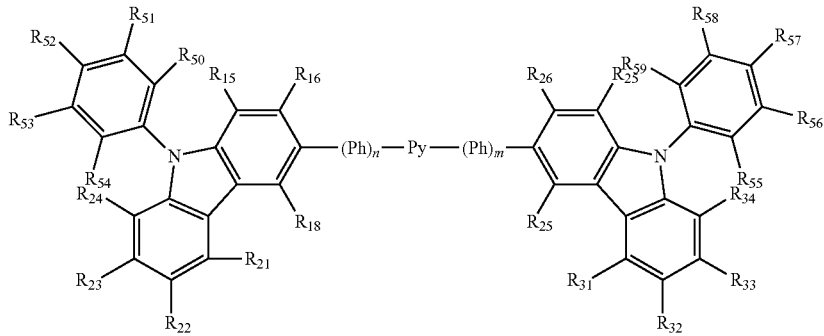

With respect to any relevant formula above, Py may be optionally substituted 3,3'-bipyrindindiyl, such as optionally substituted 3,3'-bipyrindin-4,4'-diyl. In some embodiments, Py may be unsubstituted, or may have 1, 2, 3, 4, 5, or 6 substituents, such as any substituent described above. In some embodiments, Py may be unsubstituted, or may have 1, 2, or 3 substituents independently selected from $CH_3$, $CH_2CH_3$, isopropyl, t-butyl, $CF_3$, F, Cl, Br, I, and $OCH_3$.

Also with respect to any relevant formula above, each Ph may be independently optionally substituted phenyl, such as optionally substituted p-phenylene. In some embodiments, each Ph may be unsubstituted, or may have 1, 2, 3, or 4 substituents, such as any substituent described above. In some embodiments, each Ph may be unsubstituted, or may have 1 or 2 substituents independently selected from $CH_3$, $CH_2CH_3$, isopropyl, t-butyl, $CF_3$, F, Cl, Br, I, and $OCH_3$.

Also with respect to any relevant formula above, n may be 0, 1, or 2. For example, -(Ph)$_n$- may be a bond connecting Hcy to Py, or -(Ph)$_n$- may be -Ph-, -Ph-Ph-, or -Ph-Ph-Ph-.

Also with respect to any relevant formula above, m may be 0, 1, or 2. For example, -(Ph)$_m$- may be a bond connecting Hcy to Py, or -(Ph)$_m$- may be -Ph-, -Ph-Ph-, or -Ph-Ph-Ph-.

Also with respect to any relevant formula above, $Hcy^1$ may be optionally substituted carbazolyl (for example, carbazoz-3-yl), optionally substituted diphenylamine, optionally substituted benzimidazolyl, optionally substituted benzothiazolyl and optionally substituted benzoxazolyl. In some embodiments, $Hcy^1$ may be unsubstituted carbazolyl, or carbazolyl having 1, 2, 3, 4, 5, 6, 7, or 8 substituents, such as any substituent described above. In some embodiments, $Hcy^1$ may be unsubstituted diphenylamine, or diphenylamine having 1, 2, 3, 4, 5, 6, 7, 8, 9 or 10 substituents, such as any substituent described above. In some embodiments, $Hcy^1$ may be unsubstituted benzimidazolyl, or benzimidazolyl having 1, 2, 3, or 4 substituents, such as any substituent described above. In some embodiments, $Hcy^1$ may be

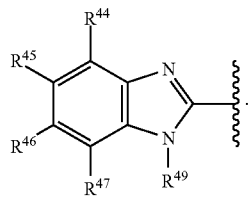

In some embodiments, $Hcy^1$ may be unsubstituted benzothiazolyl, or benzothiazolyl having 1, 2, 3, or 4 substituents, such as any substituent described above. In some embodiments, $Hcy^1$ may be unsubstituted benzoxazolyl, or benzoxazolyl having 1, 2, 3, or 4 substituents, such as any substituent described above. In some embodiments, the substituents of $Hcy^1$ may be independently selected from $CH_3$, $CH_2CH_3$, isopropyl, t-butyl, $CF_3$, F, Cl, Br, I, and $OCH_3$.

Also with respect to any relevant formula above, $Hcy^2$ may be optionally substituted carbazolyl (for example, carbazoz-3-yl), optionally substituted diphenylamine, optionally substituted benzimidazolyl, optionally substituted benzothiazolyl and optionally substituted benzoxazolyl. In some embodiments, $Hcy^2$ may be unsubstituted carbazolyl, or carbazolyl having 1, 2, 3, 4, 5, 6, 7, or 8 substituents, such as any substituent described above. In some embodiments, $Hcy^2$ may be unsubstituted diphenylamine, or diphenylamine having 1, 2, 3, 4, 5, 6, 7, 8, 9 or 10 substituents, such as any substituent described above. In some embodiments, $Hcy^2$ may be unsubstituted benzimidazolyl, or benzimidazolyl having 1, 2, 3, or 4 substituents, such as any substituent described above. In some embodiments, $Hcy^2$ may be

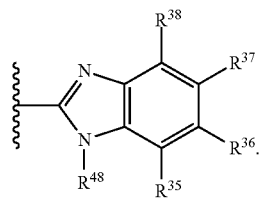

In some embodiments, $Hcy^2$ may be unsubstituted benzothiazolyl, or benzothiazolyl having 1, 2, 3, or 4 substituents, such as any substituent described above. In some embodiments, $Hcy^2$ may be unsubstituted benzoxazolyl, or benzoxazolyl having 1, 2, 3, or 4 substituents, such as any substituent described above. In some embodiments, the substituents of $Hcy^2$ may be independently selected from $CH_3$, $CH_2CH_3$, isopropyl, t-butyl, $CF_3$, F, Cl, Br, I, and $OCH_3$.

Also with respect to any relevant formula or structural depiction above, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, and $R^{59}$, also referred to herein as "$R^{1-59}$", may be H or any substituent. In some embodiments, any of $R^{1-59}$ may independently be F, Cl, Br, I, —CN, —CNO, —NCO, R', —OR', —COR', —CO$_2$R', —OCOR', —NR'COR'', CONR'R'', —NR'R'', wherein each R' and R'' may be independently H; optionally substituted phenyl; optionally substituted $C_{1-12}$ alkyl such as methyl, ethyl, propyl isomers, cyclopropyl, butyl isomers, cyclobutyl isomers (such as cyclobutyl, methylcyclopropyl, etc.), pentyl isomers, cyclopentyl isomers, hexyl isomers, cyclohexyl isomers, heptyl isomers, cycloheptyl isomers, octyl isomers, cyclooctyl isomers, nonyl isomers, cyclononyl isomers, decyl isomers, cyclodecyl isomers, or the like; or optionally substituted $C_{1-6}$ alkyl. In some embodiments each R' and R'' may be independently H, optionally substituted phenyl, $C_{1-12}$ alkyl, $C_{1-6}$ alkyl, optionally substituted $C_{1-12}$ alkyl having from 1-25 substituents, or optionally substituted $C_{1-6}$ alkyl having from 1-13 substituents, wherein the substituents are independently selected from F, Cl, Br, I, —CN, OH, SH, and $C_{1-12}$ O-alkyl. In some embodiments, $R^{19}$ and $R^{20}$ may together form a bond between the two phenyl rings. In some embodiments, $R^{48}$ and $R^{49}$ may be optionally substituted $C_{1-12}$ alkyl or optionally substituted phenyl.

In some embodiments related to Formula 2, at least one 1, at least 3, or all of any relevant moieties selected from $R^{1-59}$, such as $R^1$, $R^2$, $R^3$, $R^4$, $R^5$, and $R^6$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 3, at least one 1, at least 3, or all of any relevant moieties selected from $R^{1-59}$, such as $R^1$, $R^2$, $R^3$, $R^4$, $R^5$, and $R^6$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 4, at least one 1, at least 3, at least 6, or all of any relevant moieties selected from $R^{1-59}$, such as $R^1$, $R^2$, $R^3$, $R^4$, $R^5$, $R^6$, $R^7$, $R^8$, $R^9$, and $R^{10}$ may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 5, at least one 1, at least 5, at least 10, or all of any relevant moieties selected from $R^{1-59}$, such as $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 6, at least one 1, at least 5, at least 10, at least 15, or all of any relevant moieties selected from $R^{1-59}$, such as $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, and $R^{34}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 7, at least one 1, at least 4, at least 8, at least 12, or all of any relevant moieties selected from $R^{15}$, $R^{16}$, $R^{17}$, $R^{18}$, $R^{21}$, $R^{22}$, $R^{23}$, $R^{24}$, $R^{25}$, $R^{26}$, $R^{27}$, $R^{28}$, $R^{31}$, $R^{32}$, $R^{33}$, and $R^{34}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 8, at least one 1, at least 4, at least 8, at least 12, or all of any relevant moieties selected from $R^{1-59}$, such as $R^{15}$, $R^{16}$, $R^{17}$, $R^{18}$, $R^{19}$, $R^{20}$, $R^{21}$, $R^{22}$, $R^{23}$, $R^{24}$, $R^{35}$, $R^{36}$, $R^{37}$, and $R^{38}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 9, at least one 1, at least 4, at least 8, at least 12, or all of any relevant moieties selected from $R^{1-59}$, such as $R^{15}$, $R^{16}$, $R^{17}$, $R^{18}$, $R^{19}$, $R^{20}$, $R^{21}$, $R^{22}$, $R^{23}$, $R^{24}$, $R^{35}$, $R^{36}$, $R^{37}$, and $R^{38}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 10, at least one 1, at least 5, at least 10, at least 15, or all of any relevant moieties selected from $R^{1-59}$, such as $R^{15}$, $R^{16}$, $R^{17}$, $R^{18}$, $R^{19}$, $R^{20}$, $R^{21}$, $R^{22}$, $R^{23}$, $R^{24}$, $R^{35}$, $R^{36}$, $R^{37}$, $R^{38}$, $R^{39}$, $R^{40}$, $R^{41}$, $R^{42}$, and $R^{43}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 11, at least one 1, at least 3, at least 6, or all of any relevant moieties selected from $R^{1-59}$, such as $R^{35}$, $R^{36}$, $R^{37}$, $R^{38}$, $R^{44}$, $R^{45}$, $R^{46}$, and $R^{47}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 12, at least one 1, at least 3, at least 6, or all of any relevant moieties selected from $R^{1-59}$, such as $R^{35}$, $R^{36}$, $R^{37}$, $R^{38}$, $R^{44}$, $R^{45}$, $R^{46}$, and $R^{47}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 13, at least one 1, at least 3, at least 6, or all of any relevant moieties selected from $R^{1-59}$, such as $R^{35}$, $R^{36}$, $R^{37}$, $R^{38}$, $R^{44}$, $R^{45}$, $R^{46}$, and $R^{47}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 14, at least one 1, at least 5, at least 10, at least 15, at least 20, at least 25, at least 30, or all of any relevant moieties selected from $R^{1-59}$, such as $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, and $R^{34}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 15, at least one 1, at least 5, at least 10, at least 15, at least 20, at least 25, or all of any relevant moieties selected from $R^{1-59}$, such as $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{21}$, $R^{22}$, $R^{23}$, $R^{24}$, $R^{25}$, $R^{26}$, $R^{27}$, $R^{28}$, $R^{31}$, $R^{32}$, $R^{33}$, and $R^{34}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 16, at least one 1, at least 5, at least 10, at least 15, at least 20, or all of any relevant moieties selected from $R^{1-59}$, such as $R^1$, $R^2$, $R^3$, $R^4$, $R^5$, $R^6$, $R^7$, $R^8$, $R^9$, $R^{10}$, $R^{15}$, $R^{16}$, $R^{17}$, $R^{18}$, $R^{19}$, $R^{20}$, $R^{21}$, $R^{22}$, $R^{23}$, $R^{24}$, $R^{35}$, $R^{36}$, $R^{37}$, and $R^{38}$ may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 17, at least one 1, at least 5, at least 10, at least 15, at least 20, or all of any relevant moieties selected from $R^{1-59}$, such as $R^1$, $R^2$, $R^3$, $R^4$, $R^5$, $R^6$, $R^7$, $R^8$, $R^9$, $R^{10}$, $R^{15}$, $R^{16}$, $R^{17}$, $R^{18}$, $R^{19}$, $R^{20}$, $R^{21}$, $R^{22}$, $R^{23}$, $R^{24}$, $R^{35}$, $R^{36}$, $R^{37}$, and $R^{38}$ may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 18, at least one 1, at least 5, at least 10, at least 15, at least 20, at least 25, or all of any relevant moieties selected from $R^{1-59}$, such as $R^1$, $R^2$, $R^3$, $R^4$, $R^5$, $R^6$, $R^7$, $R^8$, $R^9$, $R^{10}$, $R^{15}$, $R^{16}$, $R^{17}$, $R^{18}$, $R^{19}$, $R^{20}$, $R^{21}$, $R^{22}$, $R^{23}$, $R^{24}$, $R^{35}$, $R^{36}$, $R^{37}$, $R^{38}$, $R^{39}$, $R^{40}$, $R^{41}$, $R^{42}$, and $R^{43}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 19, at least one 1, at least 5, at least 10, at least 15, at least 20, at least 25, at least 30, or all of any relevant moieties selected from $R^{1-59}$, such as $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{31}$, $R^{32}$, $R^{33}$, and $R^{34}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 20, at least one 1, at least 5, at least 10, at least 15, or all of any relevant moieties selected from $R^{1-59}$, such as $R^1$, $R^2$, $R^3$, $R^4$, $R^5$, $R^6$, $R^{15}$, $R^{16}$, $R^{17}$, $R^{18}$, $R^{19}$, $R^{20}$, $R^{21}$, $R^{22}$, $R^{23}$, $R^{24}$, $R^{35}$, $R^{36}$, $R^{37}$, and $R^{38}$ may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 21, at least one 1, at least 5, at least 10, at least 15, or all of any relevant moieties selected from $R^{1-59}$, such as $R^{41}$, $R^2$, $R^3$, $R^4$, $R^5$, $R^6$, $R^{15}$, $R^{16}$, $R^{17}$, $R^{18}$, $R^{19}$, $R^{20}$, $R^{21}$, $R^{22}$, $R^{23}$, $R^{24}$, $R^{35}$, $R^{36}$, $R^{37}$, and $R^{38}$ may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 22, at least one 1, at least 5, at least 10, at least 15, at least 20, or all of any relevant moieties selected from $R^{1-59}$, such as $R^1$, $R^2$, $R^3$, $R^4$, $R^5$, $R^6$, $R^{15}$, $R^{16}$, $R^{17}$, $R^{18}$, $R^{19}$, $R^{20}$, $R^{21}$, $R^{22}$, $R^{23}$, $R^{24}$, $R^{35}$, $R^{36}$ $R^{37}$, $R^{38}$, $R^{39}$, $R^{40}$, $R^{41}$, $R^{42}$ and $R^{43}$ may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 23, at least one 1, at least 5, at least 10, or all of any relevant moieties selected from $R^{1-59}$, such as $R^1$, $R^2$, $R^3$, $R^4$, $R^5$, $R^6$, $R^{35}$, $R^{36}$, $R^{37}$, $R^{38}$, $R^{44}$, $R^{45}$, $R^{46}$, and $R^{47}$ may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 24, at least one 1, at least 5, at least 10, or all of any relevant moieties selected from $R^{1-59}$, such as $R^1$, $R^2$, $R^3$, $R^4$, $R^5$, $R^6$, $R^{35}$, $R^{36}$, $R^{37}$, $R^{38}$, $R^{44}$, $R^{45}$, $R^{46}$, and $R^{47}$ may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 25, at least one 1, at least 5, at least 10, at least 15, at least 20, or all of any relevant moieties selected from $R^{1-59}$, such as $R^1$, $R^2$, $R^3$, $R^4$, $R^5$, $R^6$, $R^{35}$, $R^{36}$, $R^{37}$, $R^{38}$, $R^{44}$, $R^{45}$, $R^{46}$, and $R^{47}$ may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 26, at least one 1, at least 5, at least 10, at least 15, at least 20, or all of any relevant moieties selected from $R^{1-59}$, such as $R^1$, $R^2$, $R^3$, $R^4$, $R^5$, $R^6$, $R^7$, $R^8$, $R^9$, $R^{10}$, $R^{15}$, $R^{16}$, $R^{17}$, $R^{18}$, $R^{21}$, $R^{22}$, $R^{23}$, $R^{24}$, $R^{35}$, $R^{36}$, $R^{37}$, and $R^{38}$ may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 27, at least one 1, at least 5, at least 10, at least 15, at least 20, or all of any relevant moieties selected from $R^{1-59}$, such as $R^1$, $R^2$, $R^3$, $R^4$, $R^5$, $R^6$, $R^7$, $R^8$, $R^9$, $R^{10}$, $R^{15}$, $R^{16}$, $R^{17}$, $R^{18}$, $R^{21}$, $R^{22}$, $R^{23}$, $R^{24}$, $R^{35}$, $R^{36}$, $R^{37}$, and $R^{38}$ may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 28, at least one 1, at least 5, at least 10, at least 15, at least 20, at least 25, or all of any relevant moieties selected from $R^{1-59}$, such as $R^1$, $R^2$, $R^3$, $R^4$, $R^5$, $R^6$, $R^7$, $R^8$, $R^9$, $R^{10}$, $R^{15}$, $R^{16}$, $R^{17}$, $R^{18}$, $R^{21}$, $R^{22}$, $R^{23}$, $R^{24}$, $R^{35}$, $R^{36}$, $R^{37}$, $R^{38}$, $R^{39}$, $R^{40}$, $R^{41}$, $R^{42}$, and $R^{43}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 29, at least one 1, at least 5, at least 10, at least 15, at least 20, at least 25, or all of any relevant moieties selected from $R^{1-59}$, such as $R^{15}$, $R^{16}$, $R^{18}$, $R^{21}$, $R^{22}$, $R^{23}$, $R^{24}$, $R^{25}$, $R^{26}$, $R^{28}$, $R^{31}$, $R^{32}$, $R^{33}$, $R^{34}$, $R^{48}$, and $R^{49}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl.

In some embodiments related to Formula 30, at least one 1, at least 5, at least 10, at least 15, at least 20, at least 25, or all of any relevant moieties selected from $R^{1-59}$, such as $R^{15}$, $R^{16}$, $R^{18}$, $R^{21}$, $R^{22}$, $R^{23}$, $R^{24}$, $R^{25}$, $R^{26}$, $R^{28}$, $R^{31}$, $R^{32}$, $R^{33}$, $R^{34}$, $R^{50}$, $R^{51}$, $R^{52}$, $R^{53}$, $R^{54}$, $R^{55}$, $R^{56}$, $R^{57}$, $R^{58}$, and $R^{59}$, may be independently selected from the group consisting of H, F, Cl, Br, I, —CN, $C_{1-12}$ alkyl, $C_{1-6}$ alkyl, $C_{1-12}$ fluoroalkyl, $C_{1-6}$ fluoroalkyl, and optionally substituted phenyl. In some embodiments related to Formula 30, $R^{15}$, $R^{24}$, $R^{25}$, and $R^{34}$ are selected to be H.

Some embodiments relate to a compound selected from: optionally substituted 4-(5-(6-(4-(diphenylamino)phenyl) pyridin-3-yl)pyridin-2-yl)-N,N-diphenylbenzenamine, optionally substituted 9-(4-(5-(6-(4-(9H-carbazol-9-yl)phenyl)pyridin-3-yl)pyridin-2-yl)phenyl)-9H-carbazole, optionally substituted 4-(5-(6-(benzo[d]thiazol-2-yl)pyridin-3-yl) pyridin-2-yl)-N,N-diphenylbenzenamine, optionally substituted 4-(5-(6-(benzo[d]oxazol-2-yl)pyridin-3-yl)pyridin-2-yl)-N,N-diphenylbenzenamine, optionally substituted N,N-diphenyl-4-(5-(6-(1-phenyl-1H-benzo[d]imidazol-2-yl)pyridin-3-yl)pyridin-2-yl)benzenamine, optionally substituted 4-(5-(6-(4-(9H-carbazol-9-yl)phenyl)pyridin-3-yl)pyridin-2-yl)-N,N-diphenylbenzenamine, optionally substituted 2-(5-(6-(benzo[d]thiazol-2-yl)pyridin-3-yl)pyridin-2-yl)benzo[d]thiazole, and optionally substituted 2-(5-(6-(benzo[d]thiazol-2-yl)pyridin-3-yl)pyridin-2-yl)benzo[d]oxazole.

In some embodiments, the compound is not:

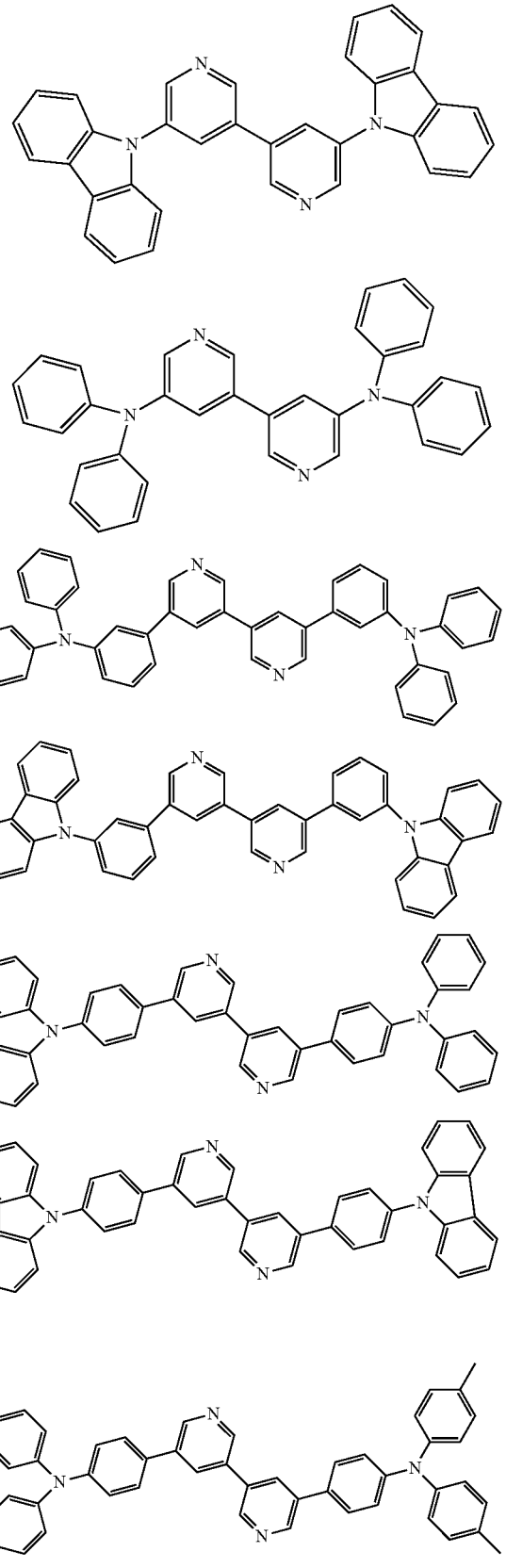

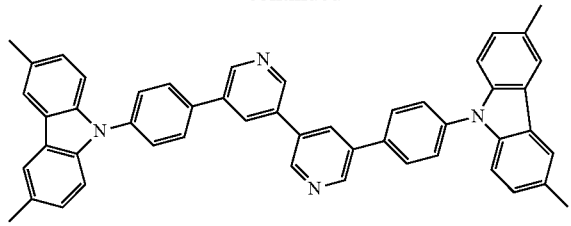

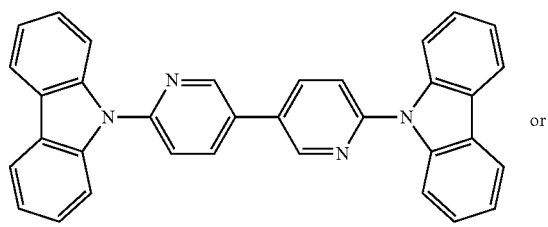

or

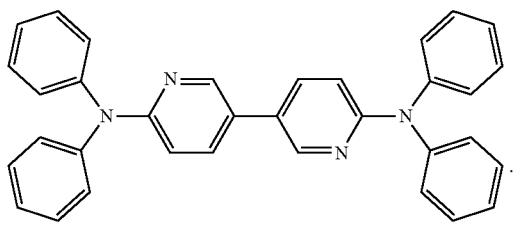

The compounds and compositions described herein can be incorporated into light-emitting devices in various ways. For example, an embodiment provides an organic component disposed between an anode and a cathode. In some embodiments, the device may be configured so that holes can be transferred from the anode to the organic component. In some embodiments, the device may be configured so that electrons can be transferred from the cathode to the organic component. The organic component may comprise the compounds and/or compositions described herein.

The anode may be a layer comprising a conventional material such as a metal, mixed metal, alloy, metal oxide or mixed-metal oxide, conductive polymer, and/or an inorganic material such as carbon nanotube (CNT). Examples of suitable metals include the Group 1 metals, the metals in Groups 4, 5, 6, and the Group 8-10 transition metals. If the anode layer is to be light-transmitting, metals in Group 10 and 11, such as Au, Pt, and Ag, or alloys thereof; or mixed-metal oxides of Group 12, 13, and 14 metals, such as indium-tin-oxide (ITO), indium-zinc-oxide (IZO), and the like, may be used. In some embodiments, the anode layer may be an organic material such as polyaniline. The use of polyaniline is described in "Flexible light-emitting diodes made from soluble conducting polymer," Nature, vol. 357, pp. 477-479 (11 Jun. 1992). Examples of suitable high work function metals and metal oxides include but are not limited to Au, Pt, or alloys thereof; ITO; IZO; and the like. In some embodiments, the anode layer can have a thickness in the range of about 1 nm to about 1000 nm.

A cathode may be a layer including a material having a lower work function than the anode layer. Examples of suitable materials for the cathode layer include those selected from alkali metals of Group 1, Group 2 metals, Group 12 metals including rare earth elements, lanthanides and actinides, materials such as aluminum, indium, calcium, barium, samarium and magnesium, and combinations thereof. Li-containing organometallic compounds, LiF, and $Li_2O$ may also be deposited between the organic layer and the cathode layer to lower the operating voltage. Suitable low work function metals include but are not limited to Al, Ag, Mg, Ca, Cu, Mg/Ag, LiF/Al, CsF, CsF/Al or alloys thereof. In some embodiments, the cathode layer can have a thickness in the range of about 1 nm to about 1000 nm.

In some embodiments, the organic component may comprise at least one light-emitting layer comprising a light-emitting component, and optionally, a host, such as a compound described herein, a hole-transport material, an electron-transport material, or an ambipolar material. In some embodiments, the device may be configured so that holes can be transferred from the anode to the light-emitting layer. In some embodiments, the device may be configured so that electrons can be transferred from the cathode to the light-emitting layer. If present, the amount of the host in a light-emitting layer can vary. In one embodiment, the amount of a host in a light-emitting layer may be in the range of from about 1% to about 99.9% by weight of the light-emitting layer. In another embodiment, the amount of a host in a light-emitting layer may be in the range of from about 90% to about 99% by weight of the light-emitting layer. In another embodiment, the amount of a host in a light-emitting layer may be about 97% by weight of the light-emitting layer.

In some embodiments, the mass of the light-emitting component may be about 0.1% to about 10%, about 1% to about 5%, or about 3% of the mass of the light-emitting layer. In some embodiments, the light-emitting layer may be a neat light-emitting layer, meaning that the light-emitting component is about 100% by weight of the light-emitting layer, or alternatively, the light-emitting layer consists essentially of light-emitting component. The light-emitting component may be a fluorescent and/or a phosphorescent compound. In some embodiments, the light-emitting component comprises a phosphorescent material.

The light-emitting component or compound may be chosen to vary the color of the light emitted by the light-emitting device. For example, a blue light-emitting component may emit a combination of visible photons so that the light appears to have a blue quality to an observer. In some embodiments, a blue light-emitting component may emit visible photons having an average wavelength in the range of about 440 nm or about 460 nm to about 490 nm or about 500 nm. The "average wavelength" of visible photons may include, when referring to the visible emission spectrum of a compound, the wavelength wherein the area under the curve for the part of the visible spectrum having a lower wavelength than the average wavelength is about equal to the area under the curve for the part of the visible spectrum having a higher wavelength than the average wavelength. Some non-limiting examples of compounds which may form part or all of a blue light-emitting component include iridium coordination compounds such as: bis-{2-[3,5-bis(trifluoromethyl)phenyl]pyridinato-N,C2'}iridium(III)-picolinate, bis(2-[4,6-difluorophenyl]pyridinato-N,C2')iridium (III) picolinate, bis(2-[4,6-difluorophenyl]pyridinato-N,C2')iridium(acetylacetonate), Iridium (III) bis(4,6-difluorophenylpyridinato)-3-(trifluoromethyl)-5-(pyridine-2-yl)-1,2,4-triazolate, Iridium (III) bis (4,6-difluorophenylpyridinato)-5-(pyridine-2-yl)-1H-tetrazolate, bis[2-(4,6-difluorophenyl)pyridinato-N,$C^{2'}$]iridium (III)tetra(1-pyrazolyl)borate, etc.

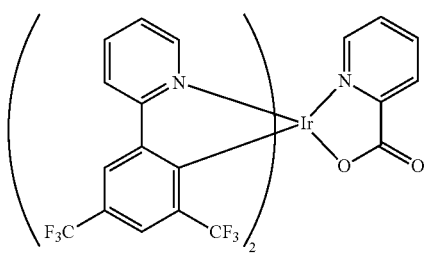

bis-{2-[3,5-bis(trifluoromethyl)phenyl]pyridinato-N,C2'}iridium(III)-picolinate (Ir(CF₃ppy)₂(Pic)

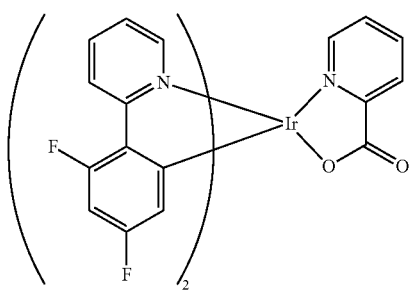

bis(2-[4,6-difluorophenyl]pyridinato-N,C2')iridium (III) picolinate [FIrPic]

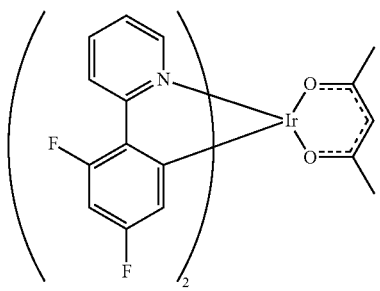

bis(2-[4,6-difluorophenyl]pyridinato-N,C2')iridium(acetylacetonate) [FIr(acac)]

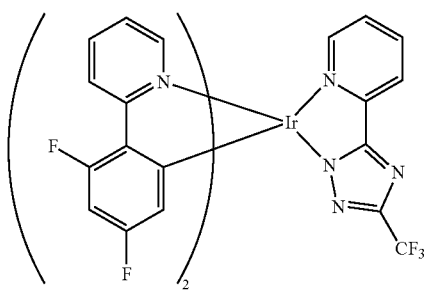

Iridium (III) bis(4,6-difluorophenylpyridinato)-3-(trifluoromethyl)-5-(pyridine-2-yl)-1,2,4-triazolate (FIrtaz)

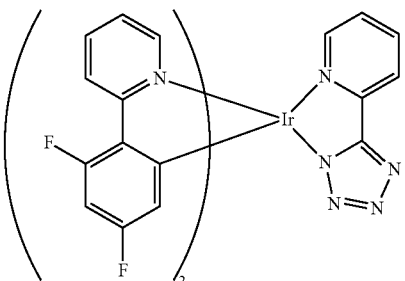

Iridium (III) bis(4,6-difluorophenylpyridinato)-5-(pyridine-2-yl)-1H-tetrazolate (FIrN4)

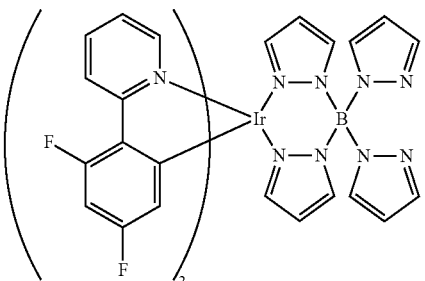

bis[2-(4,6-difluorophenyl)pyridinato-N,C2']iridium(III)tetra(1-pyrazolyl)borate (Fir6)

A red light-emitting component may emit a combination of visible photons so that the light appears to have a red quality to an observer. In some embodiments, a red light-emitting component may emit visible photons having an average wavelength in the range of about 600 nm or about 620 nm to about 780 nm or about 800 nm. Some non-limiting examples of compounds which may form part or all of a red light-emitting component include iridium coordination compounds such as: Bis[2-(2'-benzothienyl)-pyridinato-N,C3'] iridium (III)(acetylacetonate); Bis[(2-phenylquinolyl)-N,C2']iridium (III) (acetylacetonate); Bis[(1-phenylisoquinolinato-N,C2')]iridium (III) (acetylacetonate); Bis[(dibenzo[f,h]quinoxalino-N,C2')iridium (III)(acetylacetonate); Tris(2,5-bis-2'-(9',9'-dihexylfluorene)pyridine)iridium (III); Tris[1-phenylisoquinolinato-N,C2']iridium (III); Tris-[2-(2'-benzothienyl)-pyridinato-N,C3']iridium (III); Tris[1-thiophen-2-ylisoquinolinato-N,C3']iridium (III); and Tris[1-(9,9-dimethyl-9H-fluoren-2-yl)isoquinolinato-(N,C3')iridium (III)), etc.

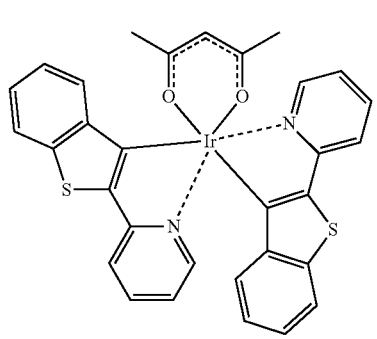

Ir(btp)₂(acac)

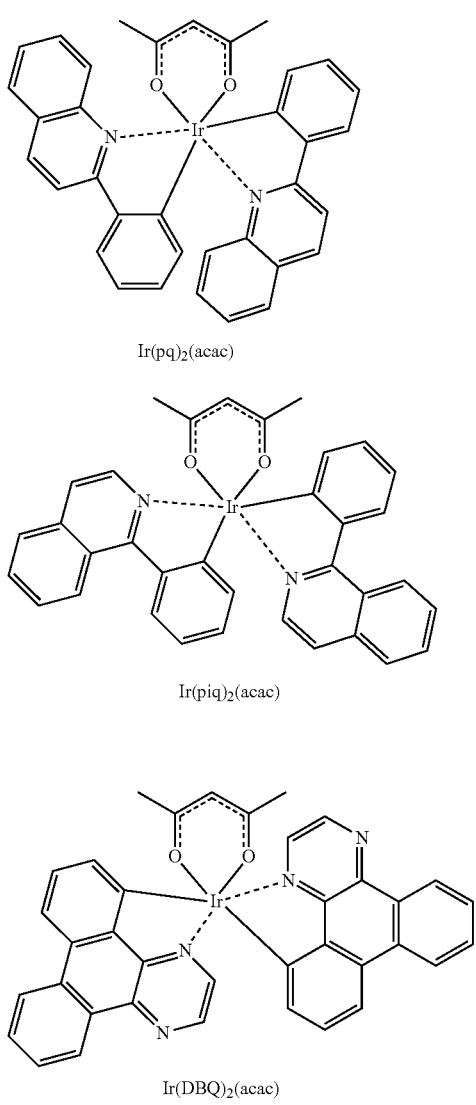
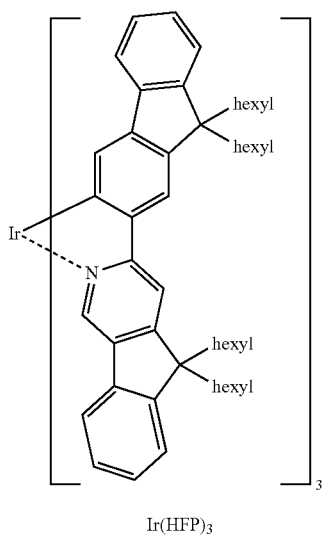
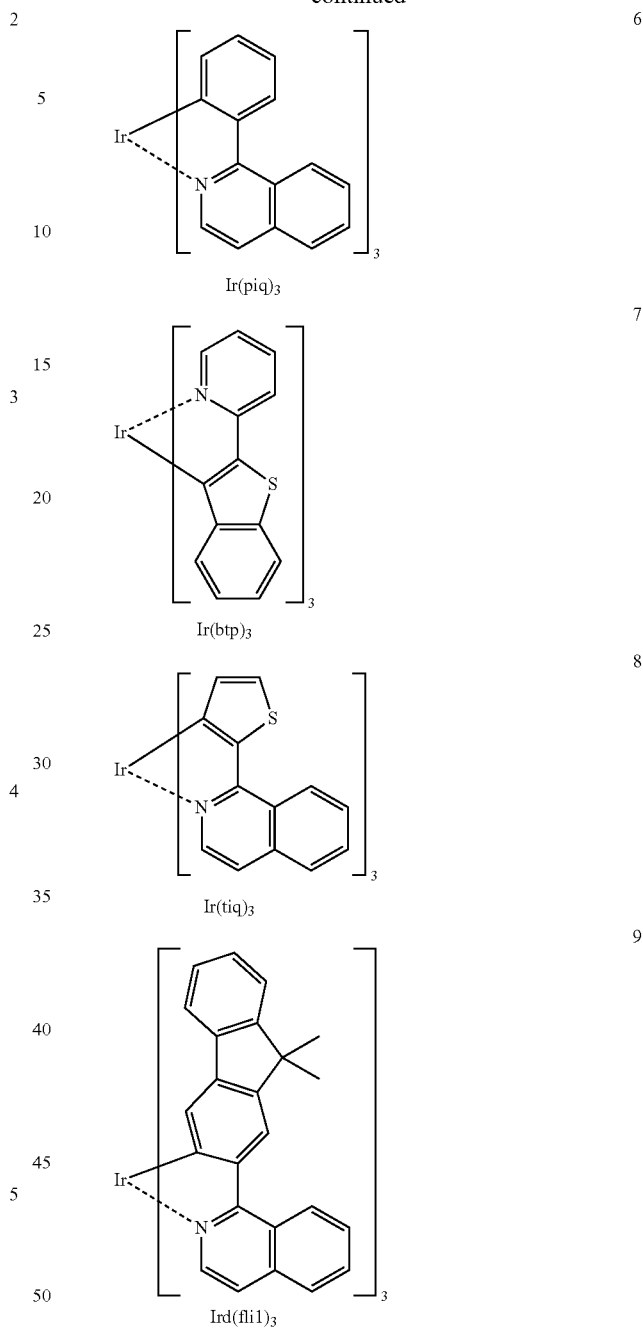

1. (Btp)$_2$Ir(III)(acac); Bis[2-(2'-benzothienyl)-pyridinato-N,C3']iridium (III)(acetylacetonate)
2. (Pq)$_2$Ir(III)(acac); Bis[(2-phenylquinolyl)-N,C2']iridium (III) (acetylacetonate)
3. (Piq)$_2$Ir(III)(acac); Bis[(1-phenylisoquinolinato-N,C2')]iridium (III) (acetylacetonate)
4. (DBQ)$_2$Ir(acac); Bis[(dibenzo[f,h]quinoxalino-N,C2')iridium (III)(acetylacetonate)
5. [Irr(HFP)$_3$], Tris(2,5-bis-2'-(9',9'-dihexylfluorene)pyridine)iridium (III)
6. Ir(piq)$_3$, Tris[1-phenylisoquinolinato-N,C2']iridium (III)
7. Ir(btp)$_3$, Tris-[2-(2'-benzothienyl)-pyridinato-N,C3']iridium (III)

8. Ir(tiq)₃, Tris[1-thiophen-2-ylisoquinolinato-N,C3']iridium (III)

9. Ir(fliq)₃; Tris[1-(9,9-dimethyl-9H-fluoren-2-yl)isoquinolinato-(N,C3')iridium (III))

A green light-emitting component may emit a combination of visible photons so that the light appears to have a green quality to an observer. In some embodiments, a green light-emitting component may emit visible photons having an average wavelength in the range of about 490 nm or about 500 nm to about 570 nm or about 600 nm. Some non-limiting examples of compounds which may form part or all of a green light-emitting component include iridium coordination compounds such as: Bis(2-phenylpyridinato-N,C2')iridium(III)(acetylacetonate) [Ir(ppy)₂(acac)], Bis(2-(4-tolyl)pyridinato-N,C2')iridium(III)(acetylacetonate) [Ir(mppy)₂(acac)], Bis(2-(4-tert-butyl)pyridinato-N,C2')iridium (III) (acetylacetonate) [Ir(t-Buppy)₂(acac)], Tris(2-phenylpyridinato-N,C2')iridium (III) [Ir(ppy)₃], Bis(2-phenyloxazolinato-N,C2')iridium (III) (acetylacetonate) [Ir(op)₂(acac)], Tris(2-(4-tolyl)pyridinato-N,C2')iridium(III) [Ir(mppy)₃], etc.

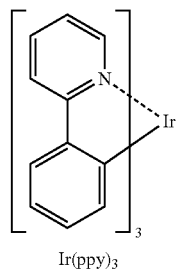

Ir(ppy)₃

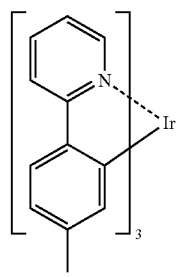

Ir(mppy)₃

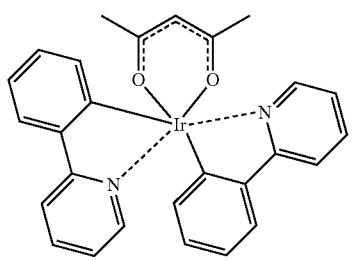

Ir(ppy)₂(acac)

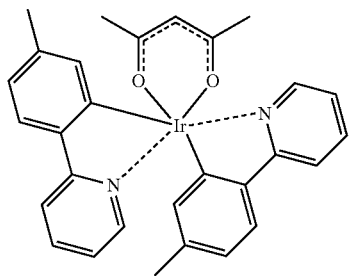

Ir(mppy)₂(acac)

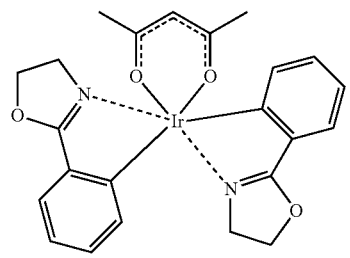

Ir(op)₂(acac)

An orange light-emitting component may emit a combination of visible photons so that the light appears to have an orange quality to an observer. In some embodiments, an orange light-emitting component may emit visible photons having an average wavelength in the range of about 570 nm or about 585 nm to about 620 nm or about 650 nm. Some non-limiting examples of compounds which may form part or all of an orange light-emitting component include iridium coordination compounds such as: Bis[2-phenylbenzothiazolato-N,C2']iridium (III)(acetylacetonate), Bis[2-(4-tert-butylphenyl)benzothiazolato-N,C2']iridium(III)(acetylacetonate), Bis[(2-(2'-thienyl)pyridinato-N,C3')]iridium (III) (acetylacetonate), Tris[2-(9,9-dimethylfluoren-2-yl)pyridinato-(N,C3')]iridium (III), Tris[2-(9,9-dimethylfluoren-2-yl)pyridinato-(N,C3')]iridium (III), Bis[5-trifluoromethyl-2-[3-(N-phenylcarbzolyl)pyridinato-N,C2']iridium(III) (acetylacetonate), (2-PhPyCz)₂Ir(III)(acac), etc.

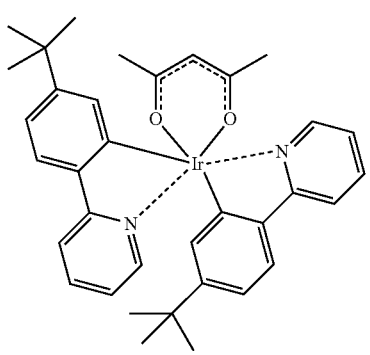

Ir(t-Buppy)₂(acac)

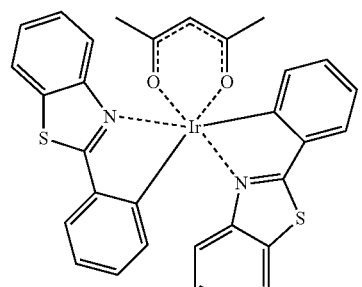

(bt)₂Ir(III)(acac)
Bis[2-phenylbenzothiazolato-
N,C2']iridium (III)(acetylacetonate)

-continued

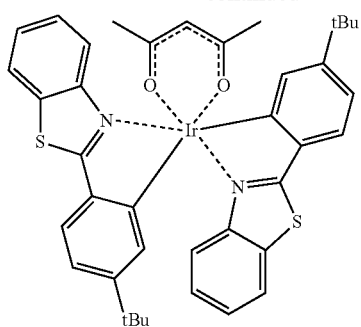

(t-bt)₂Ir(III)(acac)
Bis[2-(4-tert-
butylphenyl)benzothiazolato-
N,C2′]iridium(III)(acetykacetonate)

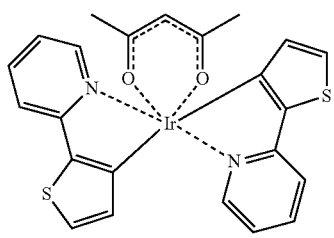

(thp)₂Ir(III)(acac)
Bis[(2-(2′-
thienyl)pyridinato-
N,C3′)]iridium (III)
(acetylacetonate)

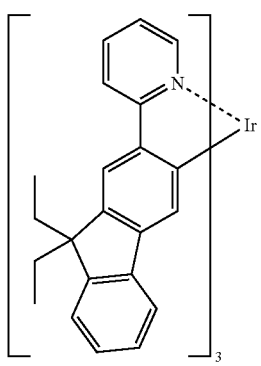

[Ir(FIpy)₃]
Trisp[2-(9,9-
dimethylfluoren-2-
yl)pyridinato-
(N,C3′)]iridium (III)

-continued

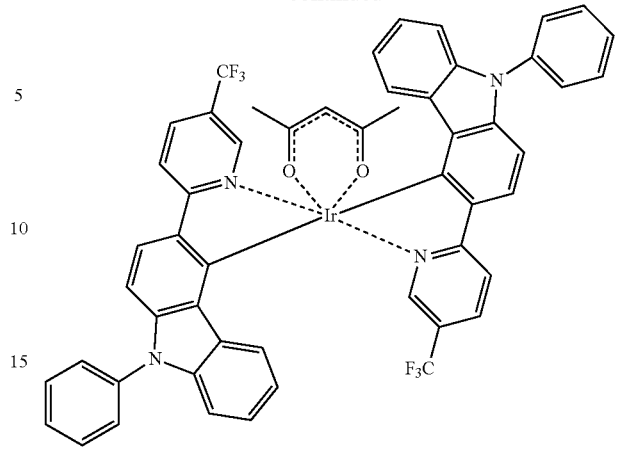

(Cz-CF₃)Ir(III)(acac)
Bis[5-trifluromethyl-2-[3-(N-
phenylcarbzolyl)pyridinato-
N,C2′]iridium(III)(acetylacetonate)

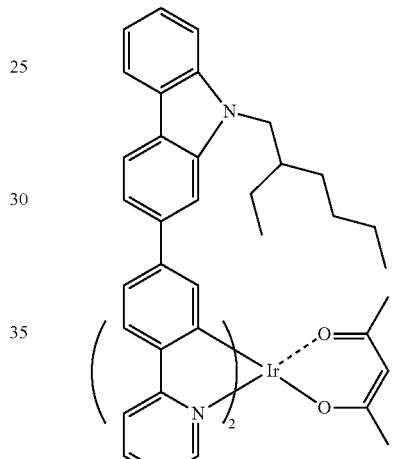

(2-PhPyCz)₂Ir(III)(acac)

The thickness of a light-emitting layer may vary. In one embodiment, a light-emitting layer may have a thickness in the range of from about 1 nm to about 150 nm or about 200 nm.

In some embodiments, the light-emitting device may emit white light. A light-emitting layer may be configured to emit white light by including a white light emitter, or a combination of colored emitters which have a combined emission that appears white. Alternatively, a combination of different colored light-emitting layers may be configured to emit white light.

In some embodiments, the organic component may further comprise a hole-transport layer disposed between the anode and the light-emitting layer. The hole-transport layer may comprise at least one hole-transport material. In some embodiments, the hole-transport material comprises at least one of an aromatic-substituted amine, a carbazole, a polyvinylcarbazole (PVK), e.g. poly(9-vinylcarbazole); polyfluorene; a polyfluorene copolymer; poly(9,9-di-n-octylfluorene-alt-benzothiadiazole); poly(paraphenylene); poly[2-(5-cyano-5-methylhexyloxy)-1,4-phenylene]; a benzidine; a phenylenediamine; a phthalocyanine metal complex; a polyacetylene; a polythiophene; a triphenylamine; copper phthalocyanine; 1,1-Bis(4-bis(4-methylphenyl)aminophenyl)cyclohexane; 2,9-Dimethyl-4,7-diphenyl-1,10-phenanthroline; 3,5-Bis(4-tert-butyl-phenyl)-4-phenyl[1,2,4]triazole; 3,4,5-Triphenyl-1,2,3-triazole; 4,4',4'-tris(3-methylphenylphenylamino)triphenylamine (MTDATA); N,N'-bis(3-methylphenyl)N,N'-diphenyl-[1,1'-biphenyl]-4,4'-diamine (TPD); 4,4'-bis[N-(naphthyl)-N-phenyl-amino]biphenyl (α-NPD); 4,4', 4''-tris(carbazol-9-yl)-triphenylamine (TCTA); 4,4'-bis[N, N'-(3-tolyl)amino]-3,3'-dimethylbiphenyl (HMTPD); 4,4'-N,N'-dicarbazole-biphenyl (CBP); 1,3-N,N-dicarbazole-benzene (mCP); Bis[4-(p,p'-ditolyl-amino)phenyl]diphenylsilane (DTASi); 2,2'-bis(4-carbazolylphenyl)-1,1'-biphenyl (4CzPBP); N,N'N''-1,3,5-tricarbazoloylbenzene (tCP); N,N'-bis(4-butylphenyl)-N,N'-bis(phenyl)benzidine; or the like.

In some embodiments, the organic component may further comprise an electron-transport layer disposed between the cathode and the light-emitting layer. In some embodiments, the electron-transport layer may comprise a compound described herein. Other electron-transport materials may be included, such as 2-(4-biphenylyl)-5-(4-tert-butylphenyl)-1, 3,4-oxadiazole (PBD); 1,3-bis(N,N-t-butyl-phenyl)-1,3,4-oxadiazole (OXD-7), 1,3-bis[2-(2,2'-bipyridine-6-yl)-1,3,4-oxadiazo-5-yl]benzene; 3-phenyl-4-(1'-naphthyl)-5-phenyl-1,2,4-triazole (TAZ); 2,9-dimethyl-4,7-diphenyl-phenanthroline (bathocuproine or BCP); aluminum tris(8-hydroxyquinolate) (Alq3); and 1,3,5-tris(2-N-phenylbenzimidazolyl)benzene; 1,3-bis[2-(2,2'-bipyridine-6-yl)-1,3,4-oxadiazo-5-yl]benzene (BPY-OXD); 3-phenyl-4-(1'-naphthyl)-5-phenyl-1,2,4-triazole (TAZ), 2,9-dimethyl-4,7-diphenyl-phenanthroline (bathocuproine or BCP); and 1,3,5-tris[2-N-phenylbenzimidazol-z-yl]benzene (TPBI). In one embodiment, the electron transport layer may be aluminum quinolate (Alq$_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

If desired, additional layers may be included in the light-emitting device. These additional layers may include an electron injection layer (EIL), a hole-blocking layer (HBL), an exciton-blocking layer (EBL), and/or a hole-injection layer (HIL). In addition to separate layers, some of these materials may be combined into a single layer.

In some embodiments, the light-emitting device can include an electron injection layer between the cathode layer and the light emitting layer. In some embodiments, the lowest unoccupied molecular orbital (LUMO) energy level of the electron injection material(s) is high enough to prevent it from receiving an electron from the light emitting layer. In other embodiments, the energy difference between the LUMO of the electron injection material(s) and the work function of the cathode layer is small enough to allow the electron injection layer to efficiently inject electrons into the light-emitting layer from the cathode. A number of suitable electron injection materials are known to those skilled in the art. Examples of suitable electron injection material(s) include but are not limited to, an optionally substituted compound selected from the following: LiF, CsF, Cs doped into electron transport material as described above or a derivative or a combination thereof.

In some embodiments, the device can include a hole-blocking layer, e.g., between the cathode and the light-emitting layer. Various suitable hole-blocking materials that can be included in the hole-blocking layer are known to those skilled in the art. Suitable hole-blocking material(s) include but are not limited to, an optionally substituted compound selected from the following: bathocuproine (BCP), 3,4,5-triphenyl-1, 2,4-triazole, 3,5-bis(4-tert-butyl-phenyl)-4-phenyl-[1,2,4] triazole, 2,9-dimethyl-4,7-diphenyl-1,10-phenanthroline, and 1,1-bis(4-bis(4-methylphenyl)aminophenyl)-cyclohexane.

In some embodiments, the light-emitting device can include an exciton-blocking layer, e.g., between the light-emitting layer and the anode. In an embodiment, the band gap energy of the material(s) that comprise exciton-blocking layer may be large enough to substantially prevent the diffusion of excitons. A number of suitable exciton-blocking materials that can be included in the exciton-blocking layer are known to those skilled in the art. Examples of material(s) that can compose an exciton-blocking layer include an optionally substituted compound selected from the following: aluminum quinolate (Alq$_3$), 4,4'-bis[N-(naphthyl)-N-phenyl-amino]biphenyl (α-NPD), 4,4'-N,N'-dicarbazole-biphenyl (CBP), and bathocuproine (BCP), and any other material(s) that have a large enough band gap to substantially prevent the diffusion of excitons.

In some embodiments, the light-emitting device can include a hole-injection layer between the light-emitting layer and the anode. Various suitable hole-injection materials that can be included in the hole-injection layer are known to those skilled in the art. Exemplary hole-injection material(s) include an optionally substituted compound selected from the following: a polythiophene derivative such as poly(3,4-ethylenedioxythiophene (PEDOT)/polystyrene sulphonic acid (PSS), a benzidine derivative such as N,N,N',N'-tetraphenyl-benzidine, poly(N,N'-bis(4-butylphenyl)-N,N'-bis(phenyl) benzidine), a triphenylamine or phenylenediamine derivative such as N,N'-bis(4-methylphenyl)-N,N'-bis(phenyl)-1,4-phenylenediamine, 4,4',4''-tris(N-(naphthylen-2-yl)-N-phenylamino)triphenylamine, an oxadiazole derivative such as 1,3-bis(5-(4-diphenylamino)phenyl-1,3,4-oxadiazol-2-yl) benzene, a polyacetylene derivative such as poly(1,2-bis-benzylthio-acetylene), and a phthalocyanine metal complex derivative such as phthalocyanine copper (CuPc). In some embodiments, hole-injection materials, while still being able to transport holes, may have a hole mobility substantially less than the hole mobility of conventional hole transport materials.

Light-emitting devices comprising the compounds described herein can be fabricated using techniques known in the art, as informed by the guidance provided herein. For example, a glass substrate can be coated with a high work functioning metal such as ITO which can act as an anode. After patterning the anode layer, a hole-injection and/or hole-transport layer may be deposited on the anode in that order. A light-emitting layer that includes a light-emitting component can be deposited on the anode, the hole-transport layer, or the hole-injection layer. The light-emitting layer may contain a compound described herein, and/or a compound described herein may be part of an electron-transport layer and/or an electron-injecting layer, deposited in that order, or may be part of an electron-injecting and electron-transport layer. The cathode layer, comprising a low work functioning metal (e.g., Mg:Ag), can then be deposited, e.g., by vapor deposition or sputtering. The device may also contain an exciton-blocking layer, an electron blocking layer, a hole blocking layer, a second light-emitting layer, or other layers that can be added to the device using suitable techniques.

Figure 1:
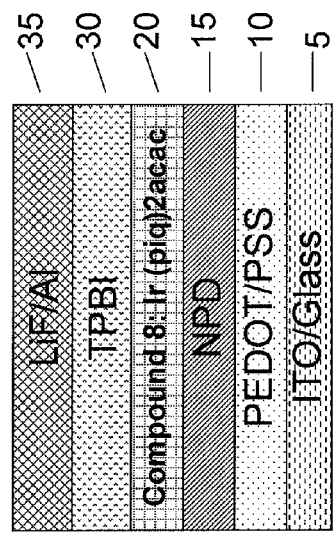
FIG. 1 is a schematic diagram of an embodiment of a device described herein.

An example of a configuration of the device comprising a compound described herein is shown in FIG. 1. The device comprises the following layers in the order given: an ITO/Glass anode 5, a PEDOT/PSS hole-injection layer 10, a hole-transport layer (NPD) 15, a light-emitting layer 20, an electron-transport layer (TPBI) 30, and a LiF/Al cathode 35.

In some embodiments, the OLED may be made by a wet process such as a process that comprises at least one of spraying, spin coating, drop casting, inkjet printing, screen printing, etc. Some embodiments provide a composition which may be a liquid suitable for deposition onto a substrate. The liquid may be a single phase, or may comprise one or more additional solid or liquid phases dispersed in it. The liquid typically comprises a light-emitting compound, a host material described herein and a solvent.

Phototherapy

The devices disclosed herein may be useful in phototherapy. Typically, phototherapy involves exposing at least a portion of the tissue of a mammal with light, such as light from a device described herein.

The phototherapy may have a therapeutic effect, such as the diagnosis, cure, mitigation, treatment, or prevention of disease, or otherwise affecting the structure or function of the body of man or other animals. Some examples of conditions that phototherapy may be useful to treat or diagnose include, but are not limited to, infection, cancer/tumors, cardiovascular conditions, dermatological conditions, a condition affecting the eye, obesity, pain or inflammation, conditions related to immune response, etc.

Examples of infections may include microbial infection such as bacterial infection, viral infection, fungus infection, protozoa infection, etc.

Examples of cancer or tumor tissues include vascular endothelial tissue, an abnormal vascular wall of a tumor, a solid tumor, a tumor of a head, a tumor of the brain, a tumor of a neck, a tumor of a gastrointestinal tract, a tumor of a liver, a tumor of a breast, a tumor of a prostate, a tumor of a lung, a nonsolid tumor, malignant cells of one of a hematopoietic tissue and a lymphoid tissue, lesions in a vascular system, a diseased bone marrow, diseased cells in which the disease is one of an autoimmune and an inflammatory disease, etc.

Examples of cardiovascular conditions may include myocardial infarction, stroke, lesions in a vascular system, such as atherosclerotic lesions, arteriovenous malformations, aneurysms, venous lesions, etc. For example, a target vascular tissue may be destroyed by cutting off circulation to the desired location.

Examples of dermatological conditions may include hair loss, hair growth, acne, psoriasis, wrinkles, discoloration, skin cancer, rosacea, etc.

Examples of eye conditions may include age related macular degeneration (AMD), glaucoma, diabetic retinopathy, neovascular disease, pathological myopia, ocular histoplasmosis, etc.

Examples of pain or inflammation include arthritis, carpal tunnel, metatarsalgia, plantar fasciitis, TMJ, pain or inflammation affecting an elbow, an ankle, a hip, a hand, etc. Examples of conditions related to immune response include, HIV or other autoimmune disease, organ transplant rejection, etc.

Other non-limiting uses of phototherapy may include treating benign prostate hyperplasia, treating conditions affecting adipose tissue, wound healing, inhibiting cell growth, and preserving donated blood.

The light itself may be at least partially responsible for the therapeutic effects of the phototherapy, thus phototherapy may be carried out without a photosensitive compound. In embodiments where a photosensitive compound is not used, light in the red range (approximately 630 nm to 700 nm) may decrease inflammation in injured tissue, increase ATP production, and otherwise stimulate beneficial cellular activity. Light in the red range may also be used in conjunction with light of other spectral wavelengths, for example blue or yellow, to facilitate post operative healing. Facial rejuvenation may be effected by applying about 633 nm radiation to the desired tissue for about 20 minutes. In some embodiments, facial skin rejuvenation is believed to be attained by applying light in the red range for a therapeutically effective amount of time.

The light may also be used in conjunction with a photosensitive compound. The photosensitive compound may be administered directly or indirectly to body tissue so that the photosensitive compound is in or on the tissue. At least a portion of the photosensitive compound may then be activated by exposing at least a portion of tissue with light.

For example, a photosensitive compound may be administered systemically by ingestion or injection, topically applying the compound to a specific treatment site on a patient's body, or by some other method. This may be followed by illumination of the treatment site with light having a wavelength or waveband corresponding to a characteristic absorption waveband of the photosensitive compound, such as about 500 or about 600 nm to about 800 nm or about 1100 nm, which activates the photosensitive compound. Activating the photosensitive compound may cause singlet oxygen radicals and other reactive species to be generated, leading to a number of biological effects that may destroy the tissue which has absorbed the photosensitive compound such as abnormal or diseased tissue.

The photosensitive compound may be any compound or pharmaceutically acceptable salts or hydrates thereof, which react as a direct or indirect result of absorption of ultraviolet, visible, or infrared light. In one embodiment, the photosensitive compound reacts as a direct or indirect result of absorption of red light. The photosensitive compound may be a compound which is not naturally in the tissue. Alternatively, the photosensitive compound may naturally be present in the tissue, but an additional amount of the photosensitive compound may be administered to the mammal. In some embodiments, the photosensitive compound may selectively bind to one or more types of selected target cells and, when exposed to light of an appropriate waveband, absorb the light, causing substances to be produced that impair or destroy the target cells.

While not limiting any embodiment, for some types of therapies, it may be helpful if the photosensitive compound has low enough toxicity so as not to cause more harm than the disease or the condition that is to be treated with the phototherapy to which it is administered or is capable of being formulated in a composition with sufficiently low toxicity that can be administered to the animal. In some embodiments, it may also be helpful if the photodegradation products of the photosensitive compounds are nontoxic.

Some non-limiting examples of photosensitive chemicals may be found in Kreimer-Birnbaum, Sem. Hematol, 26:157-73, (1989), incorporated by reference herein in its entirety, and include, but are not limited to, chlorins, e.g., Tetrahydroxylphenyl chlorin (THPC) [652 nm], bacteriochlorins [765 nm], e.g., N-Aspartyl chlorin e6 [664 nm], phthalocyanines [600-700 nm], porphyrins, e.g., hematoporphyrin [HPD][630 nm], purpurins, e.g., [1,2,4-Trihydroxyanthraquinone] Tin Etiopurpurin [660 nm], merocyanines, psoralens, benzoporphyrin derivatives (BPD), e.g., verteporfin, and porfimer sodium; and pro-drugs such as delta-aminolevulinic acid or methyl aminolevulinate, which can produce photosensitive agents such as protoporphyrin IX. Other suitable photosensitive compounds include indocyanine green (ICG) [800 nm], methylene blue [668 nm, 609 nm], toluidine blue, texaphyrins, Talaportin Sodium (mono-L-aspartyl chlorine)[664 nm], verteprofin [693 nm], which may be useful for phototherapy treatment of conditions such as age-related macular degeneration, ocular histoplasmosis, or pathologic myopia], lutetium texaphyrin [732 nm], and rostaporfin [664 nm].

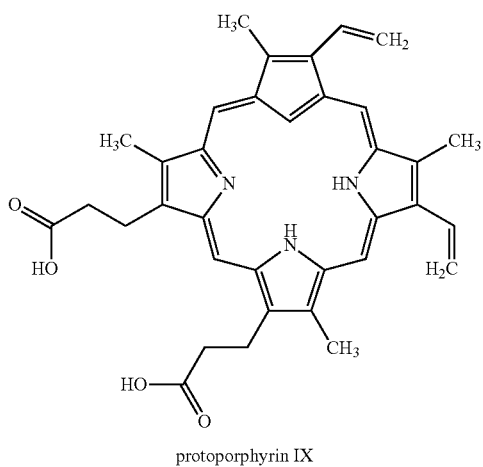
protoporphyrin IX

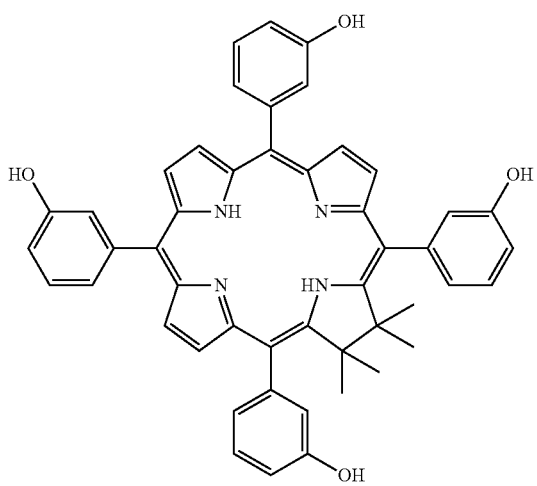
Tetrahydroxylphenyl chlorin (THPC)

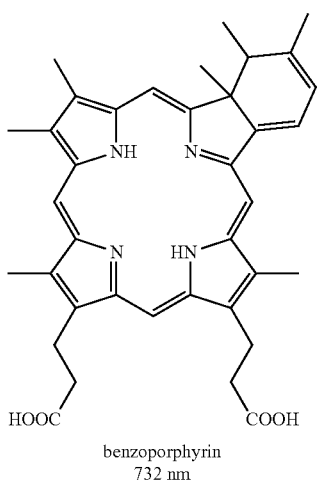
benzoporphyrin
732 nm

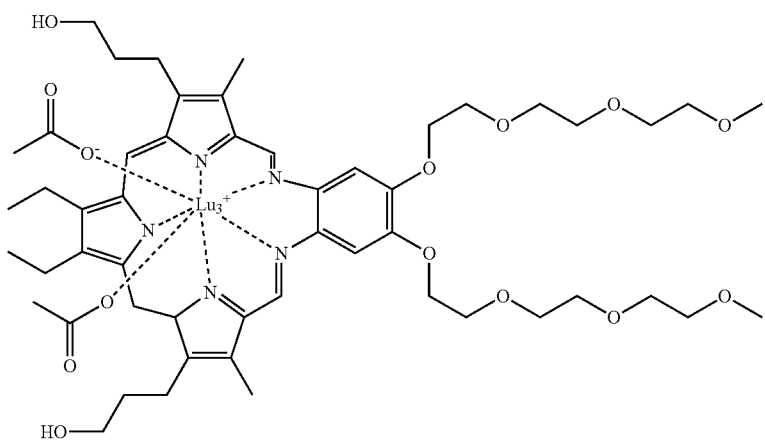
Motexafin lutetium

In some embodiments, the photosensitive compound comprises at least one component of porfimer sodium. Porfimer sodium comprises a mixture of oligomers formed by ether and ester linkages of up to eight porphorin units. The structural formula below is representative of some of the compounds present in porfimer, wherein n is 0, 1, 2, 3, 4, 5, or 6 and each R is independently —CH(OH)CH$_3$ or —CH=CH$_2$.

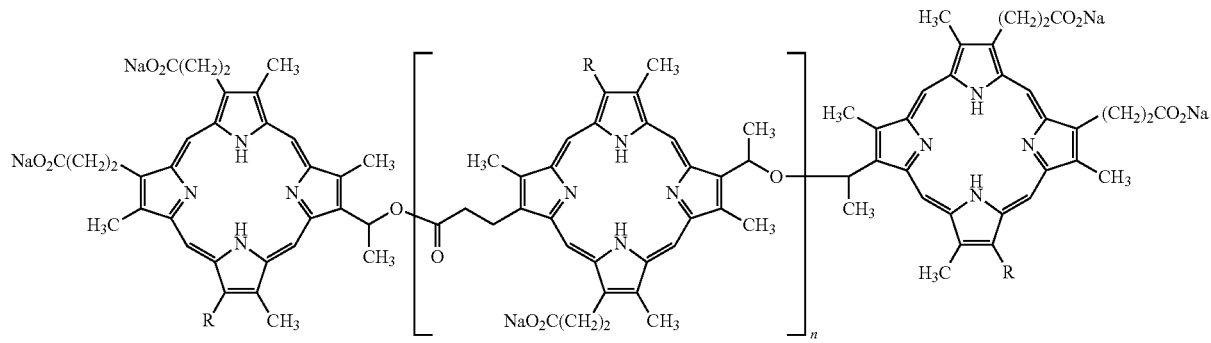

In some embodiments, the photosensitive compound is at least one of the regioisomers of verteporphin, shown below.

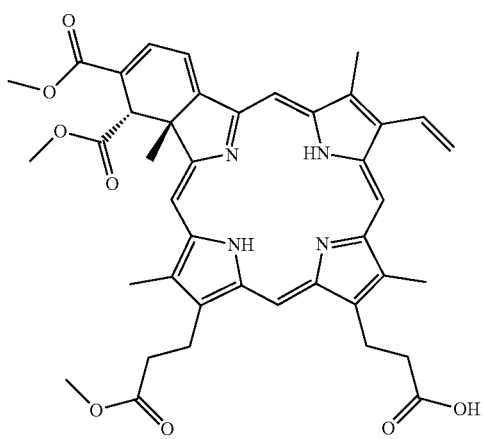

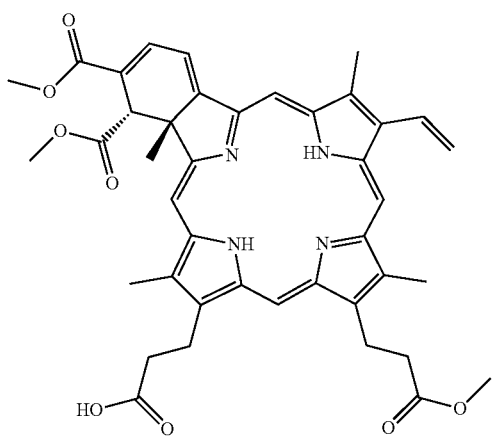

Vertiporphin regioisomers

In some embodiments, the photosensitive compound comprises a metal analogue of phthalocyanine shown below.

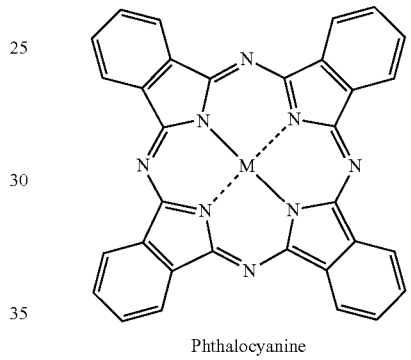

Phthalocyanine

In one embodiment, M is zinc. In one embodiment, the compound can be zinc phthalocyanine or zinc phthalocyanine tetrasulfonate.

A photosensitive agent can be administered in a dry formulation, such as a pill, a capsule, a suppository or a patch. The photosensitive agent may also be administered in a liquid formulation, either alone, with water, or with pharmaceutically acceptable excipients, such as those disclosed in Remington's Pharmaceutical Sciences. The liquid formulation also can be a suspension or an emulsion. Liposomal or lipophilic formulations may be desirable. If suspensions or emulsions are utilized, suitable excipients may include water, saline, dextrose, glycerol, and the like. These compositions may contain minor amounts of nontoxic auxiliary substances such as wetting or emulsifying agents, antioxidants, pH buffering agents, and the like. The above described formulations may be administered by methods which may include but are not limited to intradermal, intramuscular, intraperitoneal, intravenous, subcutaneous, intranasal, epidural, oral, sublingual, intranasal, intracerebral, intravaginal, transdermal, iontophoretical, rectally, by inhalation, or topically to the desired target area, for example, the body cavity (oral, nasal, rectal), ears, nose, eyes, or skin. The preferred mode of administration is left to the discretion of the practitioner, and will depend in-part upon the site of the medical condition (such as the site of cancer or viral infection).

The dose of photosensitive agent may vary. For example, the target tissue, cells, or composition, the optimal blood level, the animal's weight, and the timing and duration of the radiation administered, may affect the amount of photosensitive agent used. Depending on the photosensitive agent used, an equivalent optimal therapeutic level may have to be empirically established. The dose may be calculated to obtain a desired blood level of the photosensitive agent, which in some embodiments may be from about 0.001 g/mL or 0.01 μg/ml to about 100 μg/ml or about 1000 μg/ml.

In some embodiments, about 0.05 mg/kg or about 1 mg/kg to about 50 mg/kg or about 100 mg/kg is administered to the mammal. Alternatively, for topical application, about 0.15 mg/m² or about 5 mg/m² to about 30 mg/m² or about 50 mg/m² may be administered to the surface of the tissue.

The light may be administered by an external or an internal light source, such as an OLED device described herein. The intensity of radiation or light used to treat the target cell or target tissue may vary. In some embodiments, the intensity may be about 0.1 mW/cm² to about 100 mW/cm², about 1 mW/cm² to about 50 mW/cm², or about 3 mW/cm² to about 30 mW/cm². The duration of radiation or light exposure administered to a subject may vary. In some embodiments the exposure ranges from about 1 minute, about 60 minutes, or about 2 hours to about 24 hours, about 48 hours, or about 72 hours.

A certain amount of light energy may be required to provide a therapeutic effect. For example, a certain amount of light energy may be required to activate the photosensitive compounds. This may be accomplished by using a higher power light source, which may provide the needed energy in a shorter period of time, or a lower power light source may be used for a longer period of time. Thus, a longer exposure to the light may allow a lower power light source to be used, while a higher power light source may allow the treatment to be done in a shorter time. In some embodiments, the total fluence or light energy administered during a treatment may be in the range of 5 Joules to 1,000 Joules, 20 Joules to 750 Joules, or 50 Joules to 500 Joules.

Figure 2:
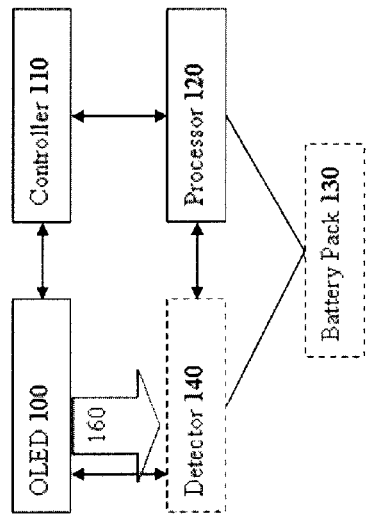
FIG. 2 is a schematic diagram of some embodiments comprising a controller and processor.

FIG. 2 is a schematic of some embodiments which further include a controller 110 and processor 120 electrically connected to an organic light-emitting diode 100 (OLED), which may help to provide a uniform power supply to facilitate homogeneous light exposure of the tissue. In some embodiments, the apparatus further includes an optional detector 140, such as photodiode, which detects a portion of the light 160 emitted from the OLED 100, to help determine the amount of light being emitted by the OLED 100. For example, the detector 140 may communicate a signal related to the intensity of the light 160 received from the OLED 100 to the processor 120, which, based upon the signal received, may communicate any desired power output information to the controller 100. Thus, these embodiments may provide real time feedback which allows the control of the intensity of light emitted from the OLED 100. The detector 140 and the processor 120 may be powered by compact power supply, such as a battery pack 130, or by some other power source.

In some embodiments related to phototherapy, the LED device may further comprise a dosage component. A dosage component may be configured to provide a sufficient amount of light to activate a sufficient portion of a photosensitive compound to provide a therapeutic effect for treating a disease. For example, a dosage component may be a timer that is configured to deliver light from the device for an amount of time sufficient to deliver the appropriate light dosage. The timer may automatically stop the emission from the device once the appropriate light dosage has been delivered. The dosage component may also comprise a positioning component that positions the device so that emitted light is delivered to the appropriate area of a mammal body and is at an appropriate distance from the affected tissue to deliver an effective amount of light. The dosage component may be configured to work with a particular photosensitive compound, or may provide flexibility. For example, a physician, a veterinarian, or another appropriate medical practitioner may set the parameters of the dosage component for use by a patient outside of the practitioner's office, such as at the patient's home. In some embodiments, the device may be provided with a set of parameters for various photosensitive compounds to assist a medical practitioner in configuring the device.

In some embodiments, the device may further include a wireless transmitter electrically connected to an component of the apparatus generating treatment information, e.g., level of intensity, time of application, dosage amount, to communicate/transfer data to another external receiving device, like cell phone, PDA or to doctor's office. In some embodiments, the apparatus may further include an adhesive tape which may be used to attach the apparatus on the tissue surface so as to stabilize it on the target area.

For phototherapy and other applications, a wavelength convertor may be positioned in the device to receive at least a portion of light emitted from the organic light-emitting diode in a lower wavelength range, such as about 350 nm to less than about 600 nm, and convert at least a portion of the light received to light in a higher wavelength range, such as about 600 nm to about 800 nm. The wavelength convertor may be a powder, a film, a plate, or in some other form and, may comprise: yttrium aluminum garnet (YAG), alumina ($Al_2O_3$), yttria ($Y_2O_3$), titania ($TiO_2$), and the like. In some embodiments, the wavelength convertor may comprise at least one dopant which is an atom or an ion of an element such as Cr, Ce, Gd, La, Tb, Pr, Sm, Eu, etc.

In some embodiments, translucent ceramic phosphor is represented by a formula such as, but not limited to $(A_{1-x}E_x)_3D_5O_{12}$, $(Y_{1-x}E_x)_3D_5O_{12}$; $(Gd_{1-x}E_x)_3D_5O_{12}$; $(La_{1-x}E_x)_3D_5O_{12}$; $(Lu_{1-x}E_x)_3D_5O_{12}$; $(Tb_{1-x}E_x)_3D_5O_{12}$; $(A_{1-x}E_x)_3Al_5O_{12}$; $(A_{1-x}E_x)_3Ga_5O_{12}$; $(A_{1-x}E_x)_3In_5O_{12}$; $(A_{1-x}Ce_x)_3D_5O_{12}$; $(A_{1-x}E_x)_3D_5O_{12}$; $(A_{1-x}Tb_x)_3D_5O_{12}$; $(A_{1-x}E_x)_3Nd_5O_{12}$; and the like. In some embodiments, the ceramic comprises a garnet, such as a yttrium aluminum garnet, with a dopant. Some embodiments provide a composition represented by the formula $(Y_{1-x}Ce_x)_3Al_5O_{12}$. In any of the above formulas, A may be Y, Gd, La, Lu, Tb, or a combination thereof; D may be Al, Ga, In, or a combination thereof; E may be Ce, Eu, Tb, Nd, or a combination thereof; and x may be in the range of about 0.0001 to about 0.1, from about 0.0001 to about 0.05, or alternatively, from about 0.01 to about 0.03

Example 1

Compound 3 was prepared as follows.

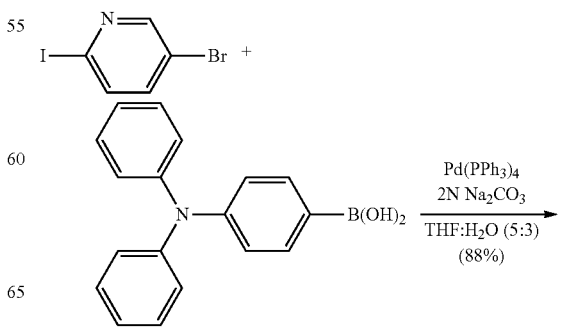

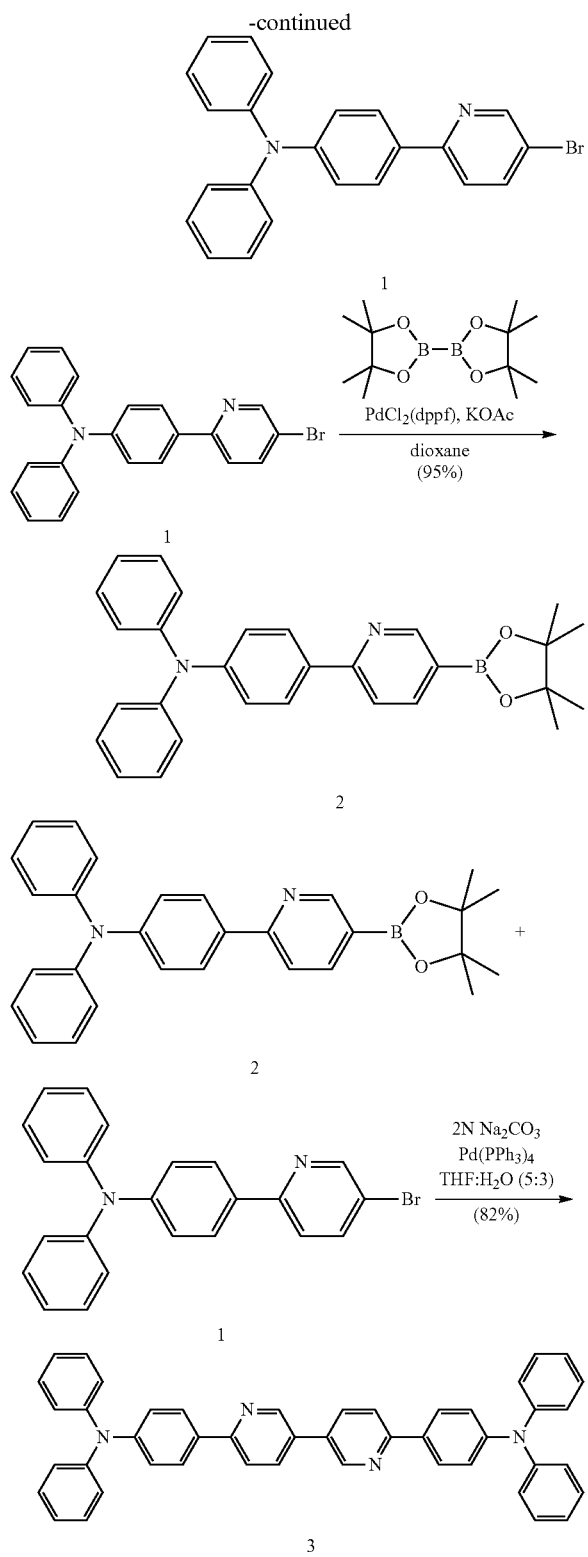

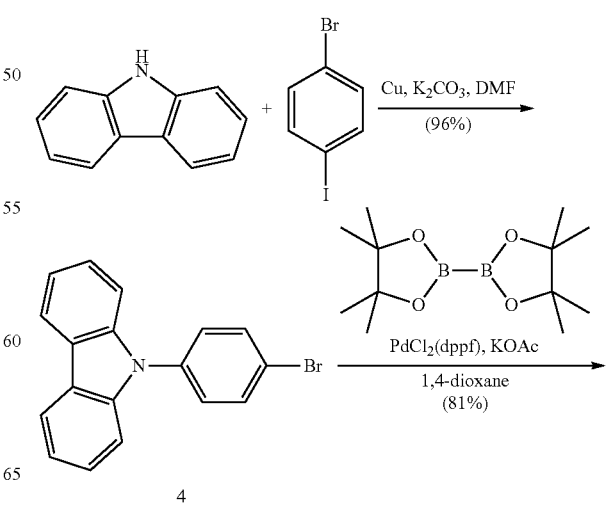

under argon at 80° C. for about 19 h. Upon confirming consumption of the starting material by thin layer chromatography (TLC) (SiO$_2$, 19:1 hexanes-EtOAc), the reaction was cooled to room temperature (RT) and poured over EtOAc (500 mL). The organics were then washed with sat. NaHCO$_3$, H$_2$O and brine, dried over MgSO$_4$, filter and concentrated in vacuo. The crude product was then purified via flash chromatography (SiO$_2$, 2:1 hexanes-dichloromethane) to afford compound 1 (9.54 g, 98% yield) as a light yellow, crystalline solid.

N,N-diphenyl-4-(5-(4,4,5,5-tetramethyl-1,3,2-dioxaborolan-2-yl)pyridin-2-yl)aniline (2). A mixture of 1 (6.00 g, 15.0 mmol), bis(pinacolato)diboron (4.18 g, 16.4 mmol), [1,1'-bis(diphenylphosphino)-ferrocene]dichloropalladium(II) (0.656 g, 0.897 mmol), potassium acetate (4.40, 44.9 mmol) and anhydrous 1,4-dioxane (90 mL) was degassed with argon for about 50 min while stirring. The stirring reaction mixture was then maintained under argon at 80° C. for about 67 h. Upon confirming consumption of the starting material by TLC (SiO$_2$, 4:1 hexanes-acetone), the reaction was cooled to RT, filtered and the filtrant washed copiously with EtOAc (ca. 200 mL). The organics were then washed with sat. NaHCO$_3$, H$_2$O, sat. NH$_4$Cl and brine, dried over MgSO$_4$, filtered and concentrated in vacuo. The crude was then taken up in hexanes (ca. 300 mL), the insolubles filtered off and the filtrate concentrated to yield 2 (6.34 g, 95% yield) as a yellow foam, which was carried forward without further purification.

4,4'-(3,3'-bipyridine-6,6'-diyl)bis(N,N-diphenylaniline) (3). A mixture of 1 (3.05 g, 7.59 mmol), 2 (3.40 g, 7.59 mmol), tetrakis(triphenylphosphine)palladium(0) (0.438 g, 0.379 mmol), Na$_2$CO$_3$ (7.42 g, 70.0 mmol), H$_2$O (70 mL) and THF (115 mL) was degassed with argon for about 1.25 h while stirring. The stirring reaction mixture was then maintained under argon at 80° C. for about 65 h. Upon confirming consumption of the starting materials by TLC (SiO$_2$, CH$_2$Cl$_2$), the reaction was cooled to room temperature (RT) and poured over CH$_2$Cl$_2$ (400 mL). The organics were then washed with sat. NaHCO$_3$, H$_2$O and brine, dried over MgSO$_4$, filter and concentrated in vacuo. Purification of the crude product via flash chromatography (SiO$_2$, 100% CH$_2$Cl$_2$ to 49:1 CH$_2$Cl$_2$-acetone) provided 3 (3.98 g, 82% yield) as a yellow solid.

Example 2

Compound 8 was prepared as follows 4-(5-bromopyridin-2-yl)-N,N-diphenylaniline (1). A mixture of 4-(diphenylamino)phenylboronic acid (7.00 g, 24.2 mmol), 5-bromo-2-iodopyridine (7.56 g, 26.6 mmol), tetrakis(triphenylphosphine)palladium(0) (1.40 g, 1.21 mmol), Na$_2$CO$_3$ (9.18 g, 86.6 mmol), H$_2$O (84 mL) and THF (140 mL) was degassed with argon for about 1.5 hours (h) while stirring. The stirring reaction mixture was then maintained

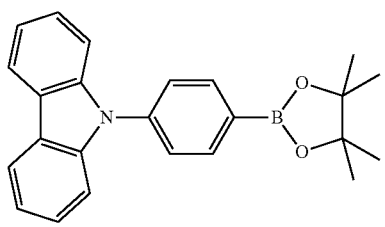

5

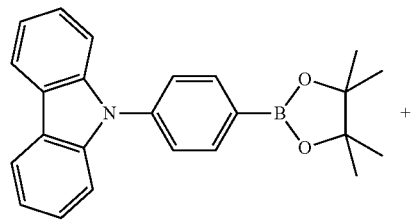

5 +

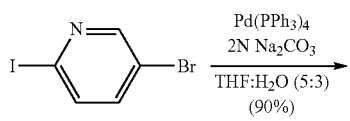

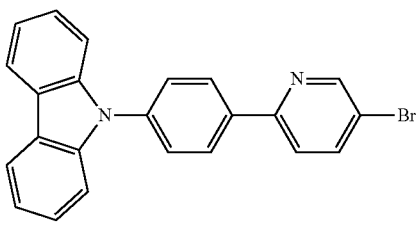

6

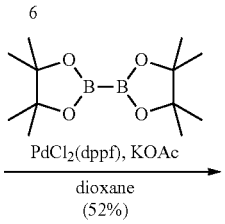

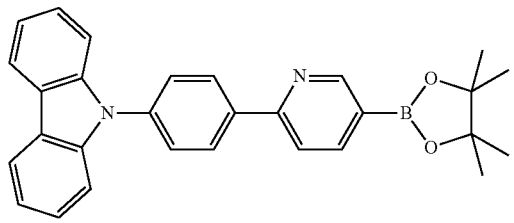

7

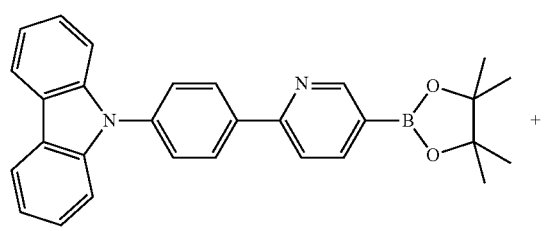

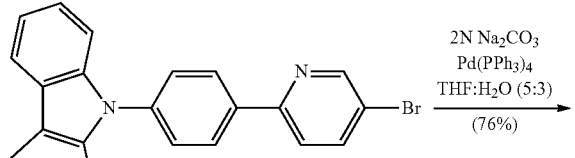

6

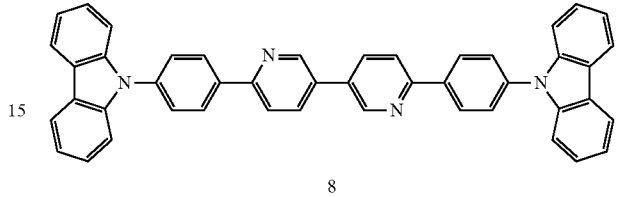

8

9-(4-bromophenyl)-9H-carbazole (4). Compound 4 was prepared as follows: a mixture of carbazole (6.30 g, 37.7 mmol), 1-bromo-4-iodobenzene (15.99 g, 56.52 mmol), copper powder (4.79 g, 75.4 mmol), $K_2CO_3$ (20.83 g, 150.7 mmol) and anhydrous DMF (100 mL) was degassed with argon for about 1 h while stirring. The stirring reaction mixture was then maintained under argon at about 130° C. for about 42 h. Upon confirming consumption of the starting material by TLC ($SiO_2$, 4:1 hexanes-dichloromethane), the mixture was cooled to RT, filtered, the filtrant washed copiously with EtOAc (ca. 200 mL) and the resulting filtrate concentrated in vacuo. Purification of the crude product by flash chromatography ($SiO_2$, hexanes) afforded compound 4 (11.7 g, 96% yield) as a pale yellow solid. (See Xu, H.; Yin, K.; Huang, W. *Chem. Eur. J.,* 2007, 13(36), 10281-10293.)

9-(4-(4,4,5,5-tetramethyl-1,3,2-dioxaborolan-2-yl)phenyl)-9H-carbazole (5). Compound 5 was prepared as follows: a mixture of 4 (11.64 g, 36.12 mmol), bis(pinacolato)diboron (19.26 g, 75.85 mmol), [1,1'-bis(diphenylphosphino)-ferrocene]dichloropalladium(II) (1.59 g, 2.17 mmol), potassium acetate (10.64, 108.4 mmol) and anhydrous 1,4-dioxane (200 mL) was degassed with argon for about 2 h while stirring. The stirring reaction mixture was then maintained under argon at about 80° C. for about 67 h. Upon confirming consumption of the starting material by TLC ($SiO_2$, hexanes), the mixture was cooled to RT, filtered through a short silica gel plug and the filtrant washed copiously with EtOAc (ca. 400 mL). The organics were then washed with sat. $NaHCO_3$, $H_2O$ and brine, dried over $MgSO_4$, filtered and concentrated in vacuo. Purification of the crude product via flash chromatography ($SiO_2$, 7:3 to 1:1 hexanes-dichloromethane) provided compound 5 (10.8 g, 81% yield) as a colorless solid. (See Sun, Y.; Zhu, X.; Chen, Z.; Zhang, Y.; Cao, Y. *J. Org. Chem.,* 2006, 71(16), 6281-6284.)

9-(4-(5-bromopyridin-2-yl)phenyl)-9H-carbazole (6). Following the procedure for 1, 5 (4.84 g, 13.1 mmol), 5-bromo-2-iodopyridine (3.72 g, 13.1 mmol), tetrakis(triphenylphosphine)palladium(0) (0.757 g, 0.655 mmol), $Na_2CO_3$ (4.97 g, 46.9 mmol), $H_2O$ (45 mL) and THF (75 mL) yielded 6 (4.73 g, 90% yield) as a colorless solid after flash chromatography ($SiO_2$, 1:1 hexanes-dichloromethane) and subsequent trituration with EtOAc.

9-(4-(5-(4,4,5,5-tetramethyl-1,3,2-dioxaborolan-2-yl)pyridin-2-yl)phenyl)-9H-carbazole (7). Following the procedure for 2, 6 (6.22 g, 15.6 mmol), bis(pinacolato)diboron (4.35 g, 17.1 mmol), [1,1'-bis(diphenylphosphino)-ferrocene]dichloropalladium(II) (0.684 g, 0.935 mmol), potassium acetate (4.59, 46.7 mmol) and anhydrous 1,4-dioxane (93 mL) yielded 7 (6.55 g, 94%) as a brownish gray solid.

6,6'-bis(4-(9H-carbazol-9-yl)phenyl)-3,3'-bipyridine (8). A mixture of 6 (4.11 g, 10.3 mmol), 7 (4.60 g, 10.3 mmol), tetrakis(triphenylphosphine)palladium(0) (0.595 g, 0.515 mmol), Na$_2$CO$_3$ (5.41 g, 51.0 mmol), H$_2$O (55 mL) and THF (92 mL) was degassed with argon for about 1 h while stirring. The stirring reaction mixture was then maintained under argon at about 80° C. for about 18 h. Upon confirming consumption of the starting materials by TLC (SiO$_2$, 49:1 dichloromethane-acetone), the reaction was cooled to RT, filtered and filtrant washed with EtOAc and H$_2$O to afford 8 (5.92 g, 90%) as an off-white solid.

Example 3

Compound 10 was prepared as follows.

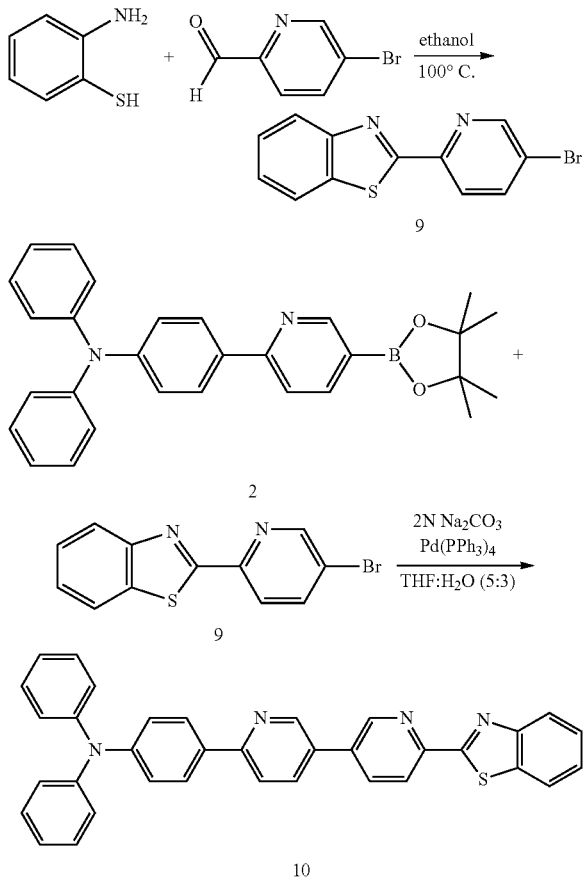

10

2-(5-bromopyridin-2-yl)benzo[d]thiazole (9). A mixture of 2-aminothiophenol (5.01 g, 40.0 mmol), 5-bromo-2-formylpyridine (7.44 g, 40.0 mmol) and ethanol (40 mL) was heated to reflux (100° C.) while open to the atmosphere for 3 days. Upon confirming consumption of the starting materials by TLC (SiO$_2$, 29:1 hexanes-acetone), the reaction was cooled to RT, the resulting mixture filtered and the filtrant washed copiously with ethanol to afford 9 (5.62 g, 48% yield) as an off-white solid.

4-(6'-(benzo[d]thiazol-2-yl)-3,3'-bipyridin-6-yl)-N,N-diphenylaniline (10). Following the procedure for 3, 2 (0.521 g, 1.16 mmol), 9 (0.338 g, 1.16 mmol), tetrakis(triphenylphosphine)palladium(0) (67.1 mg, 58.1 µmol), Na$_2$CO$_3$ (1.59 g, 15.0 mmol), H$_2$O (15 mL) and THF (25 mL) yielded 10 (0.50 g, 81% yield) as a bright yellow solid after flash chromatography (SiO$_2$, 100% CH$_2$Cl$_2$ to 99:1 CH$_2$Cl$_2$— CH$_3$OH).

Example 4

Compound 12 was prepared as follows.

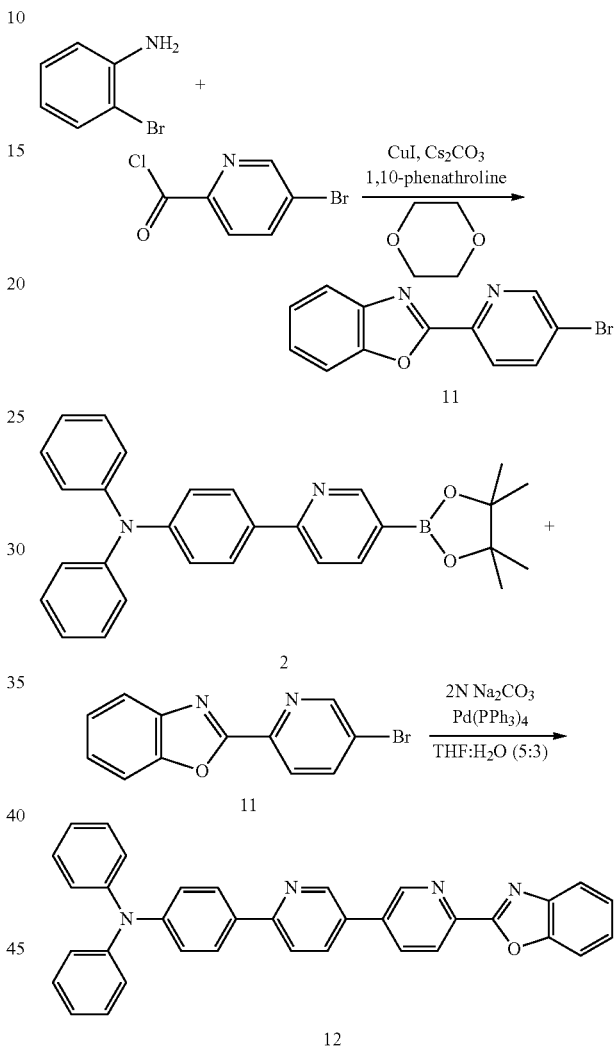

2-(5-bromopyridin-2-yl)benzo[d]oxazole (11). A mixture of 2-bromoaniline (3.90 g, 22.7 mmol), 5-bromopyridine-2-carbonyl chloride (5.00 g, 22.7 mmol), Cs$_2$CO$_3$ (14.78 g, 45.36 mmol), 1,10-phenanthroline (0.409 g, 2.27 mmol), CuI (0.216 g, 1.13 mmol) and anhydrous 1,4-dioxane (40 mL) was degassed with argon for about 40 min while stirring. The stirring reaction mixture was then maintained under argon at about 120° C. for about 40 h. Upon completion, the reaction was cooled to RT and poured over CH$_2$Cl$_2$ (300 mL). The organics were then washed with sat. NaHCO$_3$, H$_2$O and brine, dried over MgSO$_4$, filter and concentrated in vacuo. Purification of the crude product via flash chromatography (SiO$_2$, 4:1 dichloromethane-hexanes) and subsequent recrystallization from hexanes afforded compound 11 (1.86 g, 30% yield) as colorless fibers.

4-(6'-(benzo[d]oxazol-2-yl)-3,3'-bipyridin-6-yl)-N,N-diphenylaniline (12). Following the procedure for 3, 2 (0.868 g, 1.94 mmol), 11 (0.533 g, 1.94 mmol), tetrakis(triphenylphosphine)palladium(0) (112 mg, 96.8 µmol), Na₂CO₃ (1.59 g, 15.0 mmol), H₂O (15 mL) and THF (25 mL) yielded 12 (0.77 g, 77% yield) as a bright yellow solid after flash chromatography (SiO₂, 100% CH₂Cl₂ to 19:1 CH₂Cl₂-acetone).

Example 5

Compound 14 was prepared as follows.

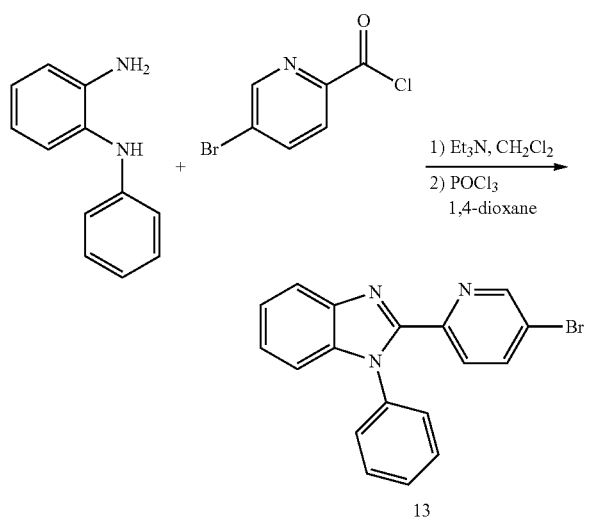

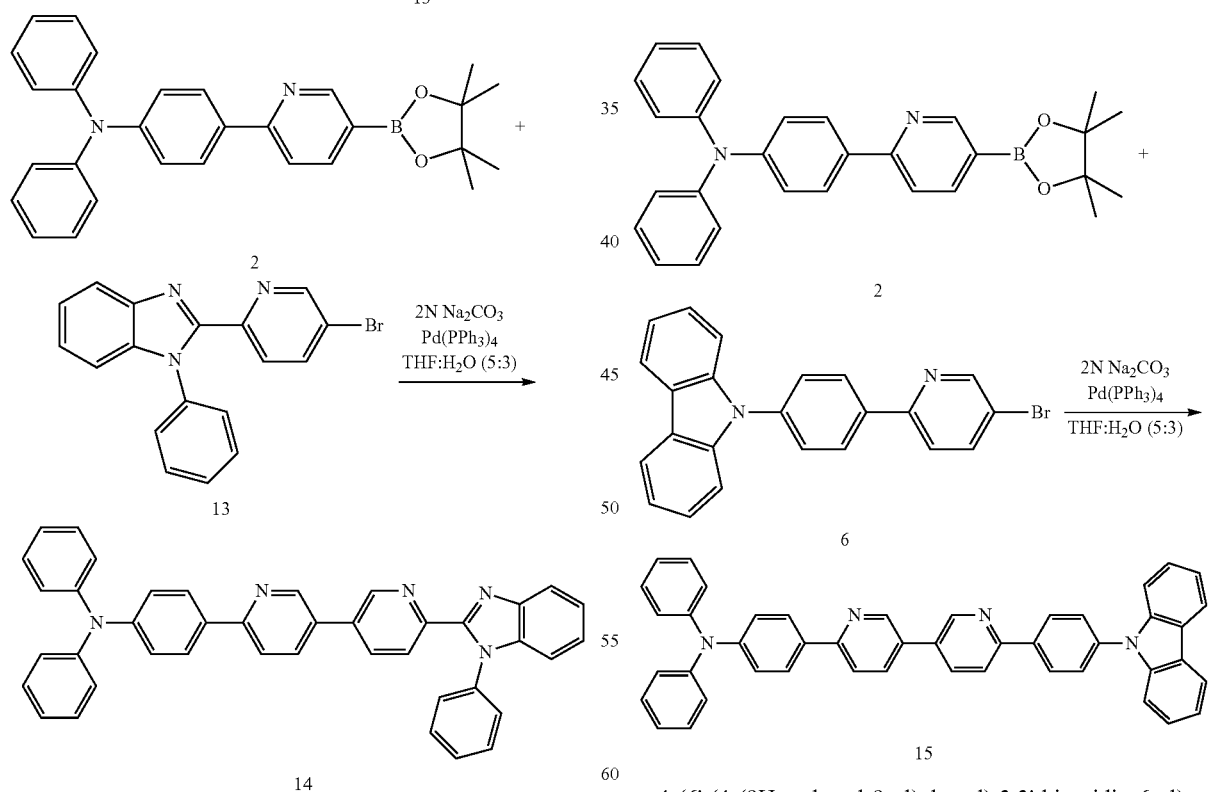

2-(5-bromopyridin-2-yl)-1-phenyl-1H-benzo[d]imidazole (13). To a stirring solution of N-phenyl-o-phenylenediamine (2.10 g, 11.4 mmol) in anhydrous CH₂Cl₂ (55 mL) was added 5-bromopyridine-2-carbonyl chloride (2.50 g, 11.3 mmol) portion-wise, followed by drop-wise addition of Et₃N (3.16 mL) via syringe. Stirring was continued at RT until TLC (SiO₂, 7:3 CH₂Cl₂-hexanes) indicated no further consumption of the starting material (10 days). The reaction was then poured over water (300 mL) and extracted with CH₂Cl₂ (150 mL). The combined organics were washed with sat. NaHCO₃, H₂O and brine, dried over MgSO₄, filtered and concentrated. The resulting solid was then partially purified via flash chromatography (SiO₂, 17:3 hexanes:EtOAc) to afford the crude intermediate. Anhydrous 1,4-dioxane (50 mL) was added to the crude solid and the mixture heated to about 70° C. Upon forming a solution, phosphorus oxychloride (3.11 mL, 33.3 mmol) was added slowly, dropwise via syringe and the reaction maintained at about 115° C. Upon completion (1 h), the reaction was cooled to RT, quenched by pipet-wise addition of sat. NaHCO₃ and poured over CH₂Cl₂ (300 mL). The organic phase was then washed with sat. NaHCO₃ (2×), H₂O and brine, dried over MgSO₄, filtered and concentrated in vacuo. Purification of the crude product via flash chromatography (SiO₂, 100% CH₂Cl₂ to 19:1 CH₂Cl₂-acetone) afforded 13 (2.20 g, 55%) as a light brown solid.

N,N-diphenyl-4-(6'-(1-phenyl-1H-benzo[d]imidazol-2-yl)-3,3'-bipyridin-6-yl)aniline (14). Following the procedure for 3, 2 (0.758 g, 1.69 mmol), 13 (0.592 g, 1.69 mmol), tetrakis(triphenylphosphine)palladium(0) (97.6 mg, 84.5 µmol), Na₂CO₃ (1.59 g, 15.0 mmol), H₂O (15 mL) and THF (25 mL) yielded 14 (0.88 g, 88%) as a yellow solid after flash chromatography (SiO₂, 100% CH₂Cl₂ to 9:1 CH₂Cl₂-acetone).

Example 6

Compound 15 was prepared as follows.

4-(6'-(4-(9H-carbazol-9-yl)phenyl)-3,3'-bipyridin-6-yl)-N,N-diphenylaniline (15). Following the procedure for 3, 2 (0.700 g, 1.56 mmol), 6 (0.623 g, 1.56 mmol), tetrakis(triphenylphosphine)palladium(0) (90 mg, 78 µmol), Na₂CO₃ (1.59 g, 15.0 mmol), H₂O (15 mL) and THF (25 mL) yielded 15 (0.81 g, 81%) as a light yellow solid after flash chromatography (SiO₂, 100% CH₂Cl₂ to 49:1 CH₂Cl₂-acetone).

Example 7

Compound 17 was prepared as follows:

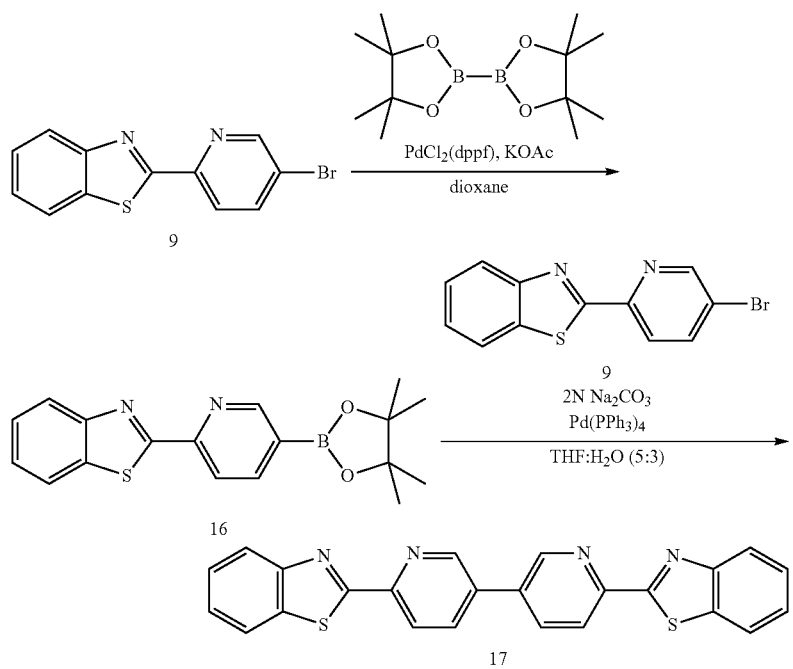

2-(5-(4,4,5,5-tetramethyl-1,3,2-dioxaborolan-2-yl)pyridin-2-yl)benzo[d]thiazole (16). A mixture of 9 (3.00 g, 10.3 mmol), bis(pinacolato)diboron (2.88 g, 11.3 mmol), [1,1'-bis(diphenylphosphino)-ferrocene]dichloropalladium(II) (0.452 g, 0.618 mmol), potassium acetate (3.03, 30.9 mmol) and anhydrous 1,4-dioxane (60 mL) was degassed with argon for about 40 min while stirring. The stirring reaction mixture was then maintained under argon at about 80° C. for about 23 h. Upon confirming consumption of the starting material by TLC (SiO$_2$, 49:1 CH$_2$Cl$_2$-acetone), the mixture was cooled to RT, filtered and the filtrant washed copiously with EtOAc (ca. 300 mL). The organics were then washed with sat. NaHCO$_3$, H$_2$O and brine, dried over MgSO$_4$, filtered and concentrated in vacuo. The crude was then taken up in hexanes (ca. 300 mL), the insolubles filtered off and the filtrate concentrated to yield 16 (2.38 g, 68%) as a brown solid, which was carried forward without further purification.

6,6'-di(benzo[d]thiazol-2-yl)-3,3'-bipyridine (17). A mixture of 9 (0.591 g, 2.03 mmol), 16 (0.700 g, 2.07 mmol), tetrakis(triphenylphosphine)palladium(0) (117 mg, 102 μmol), Na$_2$CO$_3$ (1.59 g, 15.0 mmol), H$_2$O (15 mL) and THF (25 mL) was degassed with argon for about 20 min while stirring. The stirring reaction mixture was then maintained under argon at about 80° C. for about 19 h. Upon completion, the mixture was cooled to RT, filtered and the precipitate collected as a white solid (0.83 g, 97%). This compound was found to be insoluble in numerous common organic solvents.

Example 8

Compound 18 was prepared as follows:

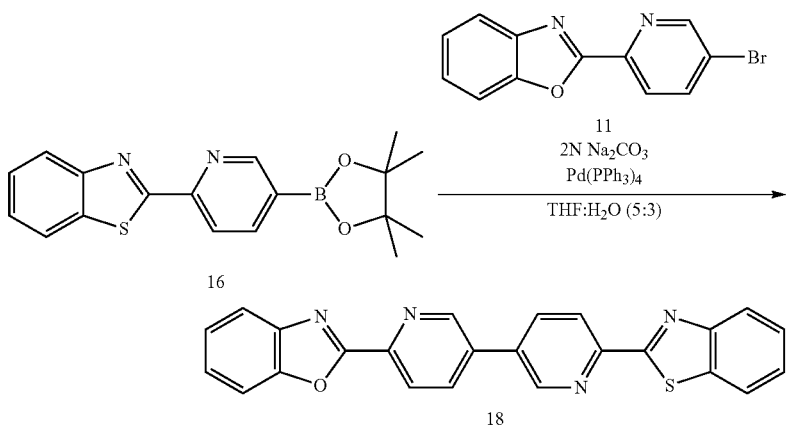

2-(6'-(benzo[d]thiazol-2-yl)-3,3'-bipyridin-6-yl)benzo[d]oxazole (18). Following the procedure for 17, 11 (0.558 g, 2.03 mmol), 16 (0.700 g, 2.07 mmol), tetrakis(triphenylphosphine)palladium(0) (117 mg, 102 µmol), Na$_2$CO$_3$ (1.59 g, 15.0 mmol), H$_2$O (15 mL) and THF (25 mL) yielded an insoluble white solid (0.70 g, 84%) after filtration.

Example 9

Compound 19 was prepared as follows:

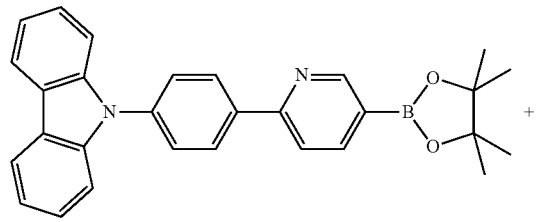

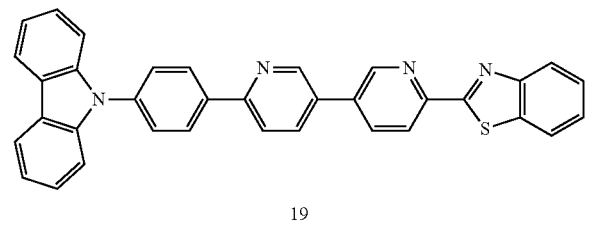

2-(6'-(4-(9H-carbazol-9-yl)phenyl)-3,3'-bipyridin-6-yl)benzo[d]thiazole (19). A mixture of 7 (0.841 g, 1.89 mmol), 9 (0.549 g, 1.89 mmol), tetrakis(triphenylphosphine)palladium(0) (109 mg, 94.2 µmol), Na$_2$CO$_3$ (1.59 g, 15.0 mmol), H$_2$O (15 mL) and THF (25 mL) was degassed with argon for about 20 min while stirring. The stirring reaction mixture was then maintained under argon at about 80° C. for about 18 h. Upon confirming consumption of the starting materials by TLC (SiO$_2$, CH$_2$Cl$_2$), the mixture was cooled to RT and poured over CHCl$_3$ (300 mL). The organics were then washed with sat. NaHCO$_3$, H$_2$O and brine, dried over MgSO$_4$, filter and concentrated in vacuo. Purification of the crude product via flash chromatography (SiO$_2$, 100% CH$_2$Cl$_2$ to 49:1 CH$_2$Cl$_2$-acetone) provided 19 (0.72 g, 72%) as a light yellow solid.

Example 10

Compound 20 was prepared as follows:

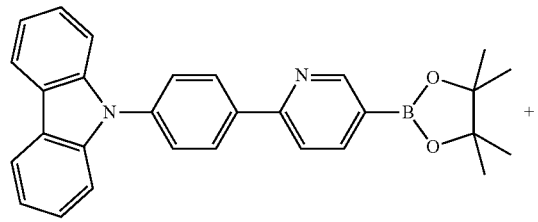

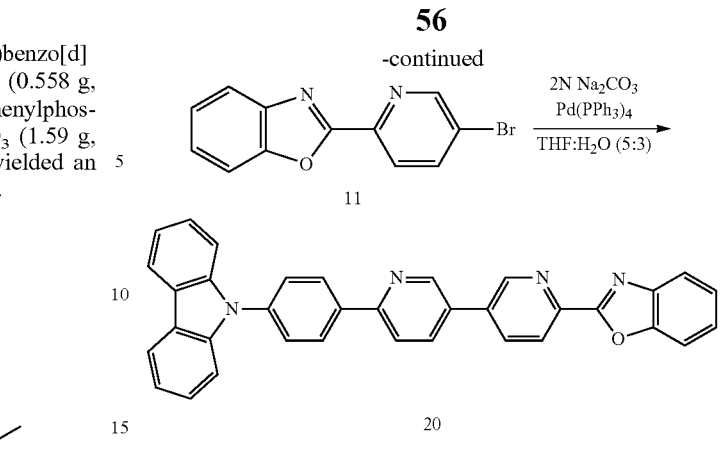

2-(6'-(4-(9H-carbazol-9-yl)phenyl)-3,3'-bipyridin-6-yl)benzo[d]oxazole (20). Following the procedure for 19, 7 (0.868 g, 1.95 mmol), 11 (0.535 g, 1.95 mmol), tetrakis(triphenylphosphine)palladium(0) (112 mg, 97.2 µmol), Na$_2$CO$_3$ (1.59 g, 15.0 mmol), H$_2$O (15 mL) and THF (25 mL) yielded 20 (0.81 g, 81%) as a white solid after flash chromatography (SiO$_2$, 100% CH$_2$Cl$_2$ to 19:1 CH$_2$Cl$_2$-acetone).

Example 11

Compound 21 was prepared as follows:

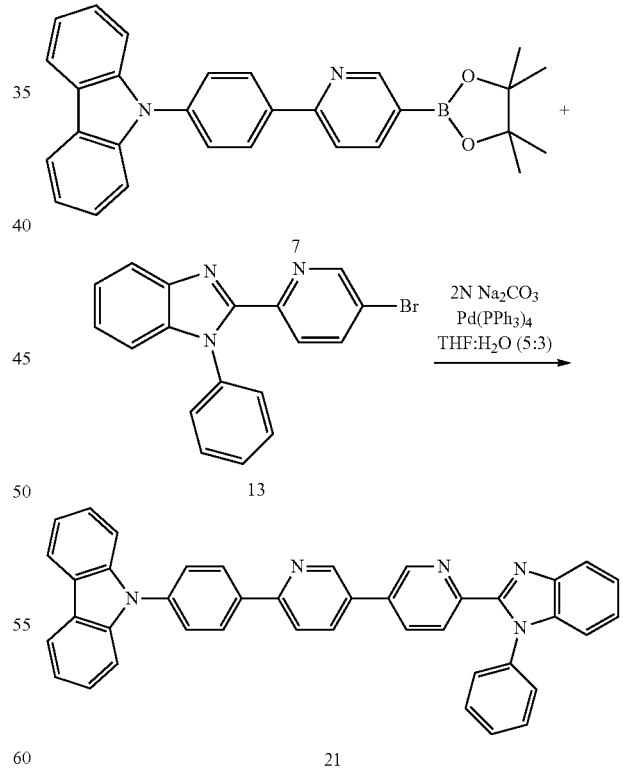

9-(4-(6'-(1-phenyl-1H-benzo[d]imidazol-2-yl)-3,3'-bipyridin-6-yl)phenyl)-9H-carbazole (21). Following the procedure for 19, 7 (0.757 g, 1.70 mmol), 13 (0.594 g, 1.70 mmol), tetrakis(triphenylphosphine)palladium(0) (98 mg, 85 µmol), Na$_2$CO$_3$ (1.59 g, 15.0 mmol), H$_2$O (15 mL) and THF (25 mL)

yielded 21 (0.70 g, 70% yield) as a light yellow solid after flash chromatography (SiO$_2$, 100% CH$_2$Cl$_2$ to 19:1 CH$_2$Cl$_2$-acetone).

Example 12

Compound 22 was prepared as follows:

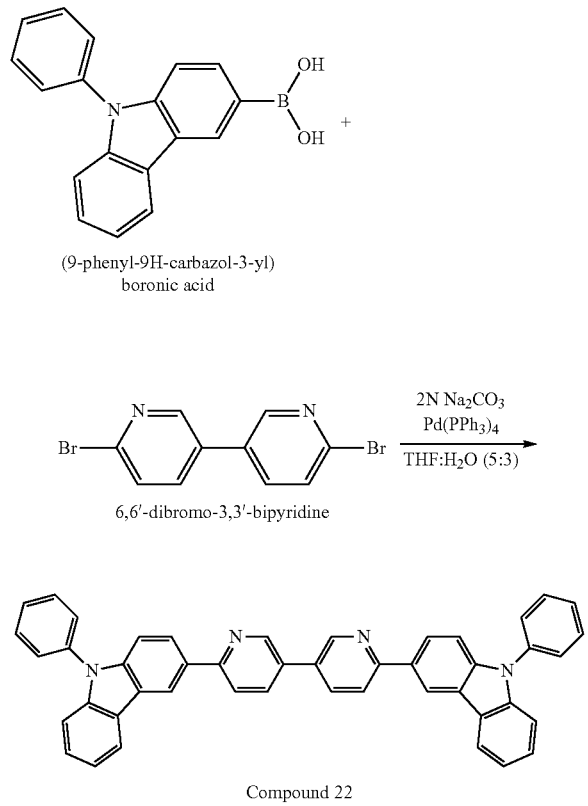

6,6'-bis(9-phenyl-9H-carbazol-3-yl)-3,3'-bipyridine (Compound 22). A mixture of (9-phenyl-9H-carbazol-3-yl) boronic acid (1.41 g, 4.92 mmol), 6,6'-dibromo-3,3'-bipyridine (0.750 g, 2.39 mmol), tetrakis(triphenylphosphine)palladium(0) (0.166 g, 0.143 mmol), Na$_2$CO$_3$ (1.59 g, 15.0 mmol), H$_2$O (15 mL) and THF (25 mL) was degassed with argon for about 25 min while stirring. The reaction mixture was then maintained at about 85° C. under argon. Upon confirming consumption of the starting material by thin layer chromatography (TLC) (SiO$_2$, dichloromethane), the reaction was cooled to RT and poured over CH$_2$Cl$_2$ (ca. 350 mL). The organics were then washed with saturated NaHCO$_3$, H$_2$O and brine, dried over MgSO$_4$, filtered and concentrated in vacuo. Purification of the crude via flash chromatography (SiO$_2$, 100% CH$_2$Cl$_2$ to 29:1 CH$_2$Cl$_2$-acetone) afforded Compound 22 (0.98 g, 64%) as an off-white solid. MS (ES$^+$) m/z: 639 (C$_{46}$H$_{30}$N$_4$ requires 639).

Example 13

Device Fabrication

Fabrication of Light-Emitting Device:
A device was fabricated as follows. The ITO substrates having sheet resistance of about 14 ohm/sq were cleaned ultrasonically and sequentially in detergent, water, acetone and then IPA; and then dried in an oven at about 80° C. for about 30 min under ambient environment. Substrates were then baked at about 200° C. for about 1 hour in an ambient environment, then under UV-ozone treatment for about 30 minutes. PEDOT:PSS (hole-injection material) was then spin-coated onto the annealed substrate at about 4000 rpm for about 30 sec. The coated layer was then baked at about 100° C. for about 30 min in an ambient environment, followed by baking at about 200° C. for about 30 min inside a glove box (N$_2$ environment). The substrate was then transferred into a vacuum chamber, where N,N'-Bis(naphthalen-1-yl)-N,N'-bis(phenyl)-2,2'-dimethylbenzidine (a-NPD [hole transporting material]) was vacuum deposited at a rate of about 0.1 nm/s rate under a base pressure of about 2×10$^{-7}$ torr. Bis(1-phenylisoquinoline)(acetylacetonate)iridium (III) ("Ir(piq)$_2$acac") (10 wt %) was co-deposited as an emissive layer with Compound 8 host material at about 0.01 nm/s and about 0.10 nm/s, respectively, to make the appropriate thickness ratio. 1,3,5-Tris(1-phenyl-1H-benzimidazol-)2-yl)benzene (TPBI) is then deposited at about 0.1 nm/s rate on the emissive layer. A layer of lithium fluoride (LiF) (electron injection material) was deposited at about 0.005 nm/s rate followed by deposition of the cathode as Aluminium (Al) at about 0.3 nm/s rate. The representative device structure was: ITO (about 150 nm thick)/PEDOT:PSS (about 40 nm thick)/α-NPD (about 40 nm thick)/Compound 8: Ir(piq)$_2$acac (about 30 nm thick)/TPBI (about 30 nm thick)/LiF(about 0.5 nm thick)/Al (about 120 nm thick). The device was then encapsulated with a getter attached glass cap to cover the emissive area of the OLED device in order to protect from moisture, oxidation or mechanical damage. Each individual device has an area of about 1.6 cm$^2$.

Figure 4:
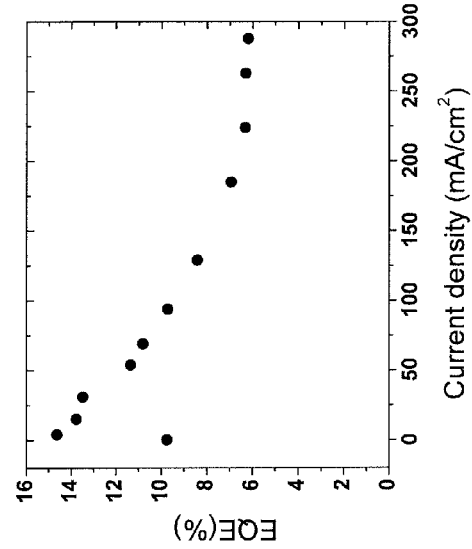
FIG. 4 is a current density/brightness vs. voltage curve of an embodiment of a light emitting device.
Figure 5:
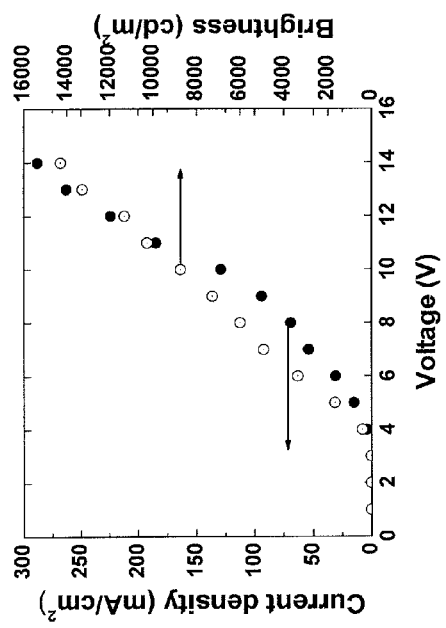
FIG. 5 shows the EQE (external quantum efficiency) and the luminescence efficiency with respect to the current density of an embodiment of a light-emitting device.
Figure 6:
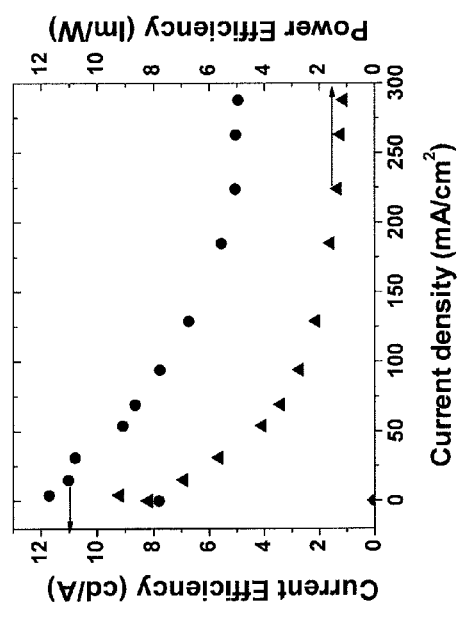
FIG. 6 is a plot of current efficiency/power efficiency vs. current density of an embodiment of a light emitting device.

The electroluminescence spectrum (EL) of the device fabricated above was collected at 3 V (FIG. 3). In addition, device performance of the device was evaluated by measuring the current density and luminance as a function of the driving voltage, as shown in FIG. 4-6. The turn-on voltage for the device was about 2.6 volts and the maximum luminance was about 14,000 cd/m$^2$ with 1.6 cm$^2$ area device at 14V. The EQE (external quantum efficiency), luminous efficiency and power efficiency of the device at 1000 cd/m$^2$ were about 14.6%, 11.3 cd/A and 8.1 μm/w at 630 nm emission. Four additional devices were constructed similar to that described above (emissive layers separately comprising Compounds 3, 10, 12 or bis(10-hydroxybenzo[h]quinolinato)beryllium complex (Bebq2 [Luminescence Technology, Taipei, Taiwan; and San Jose, Calif., USA] were used instead of Compound 8).

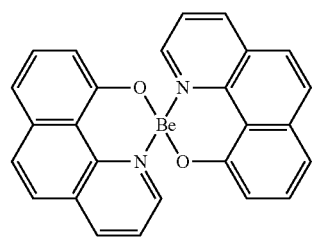

Bebq2

Figure 7:
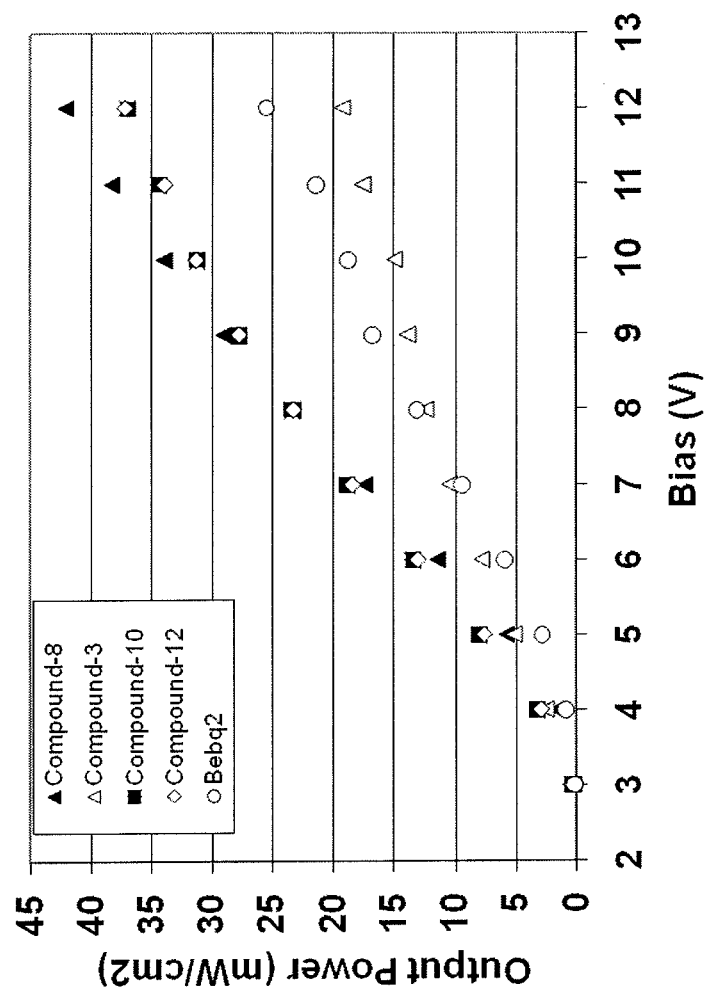
FIG. 7 is a plot of power output vs. voltage of an embodiment of a light emitting device.

Device performance was also evaluated by measuring the power output as a function of applied bias as shown in FIG. 7.

A device efficiency of 14% was higher than expected, and demonstrates that Compound 8 may be useful as host material in a light emitting device.

Example 14

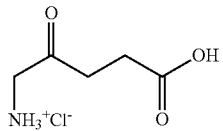

5-Aminolevulinic acid HCl

5-Aminolevulinic acid HCl (20% topical solution, available as LEVULAN® KERASTICK® from DUSA® Pharmaceuticals) is topically applied to individual lesions on a person suffering from actinic keratoses. About 14-18 hours after application, the treated lesions are illuminated with a red light emitting OLED device constructed as set forth in Example 13 (Compound 8:Ir(piq)$_2$acac emissive layer and no wavelength convertor layer) at an intensity of about 20 mW/cm$^2$ for about 8.3 minutes.

After the treatment, the number or severity of the lesions is anticipated to be reduced. The treatment is repeated as needed.

Example 15

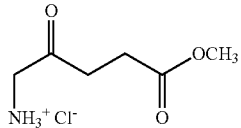

Methyl aminolevulinate

Methyl aminolevulinate (16.8% topical cream, available as METVIXIA® Cream from GALERMA LABORATORIES, Fort Worth, Tex., USA) is topically applied to individual lesions on a person suffering from actinic keratoses. The excess cream is removed with saline, and the lesions are illuminated with the red light emitting OLED constructed as set forth in Example 13.

Nitrile gloves are worn at all times during the handling of methyl aminolevulinate. After the treatment, it is anticipated that the number or severity of the lesions is reduced. The treatment is repeated as needed.

Example 16

Verteporphin is intravenously injected, over a period of about 10 minutes at a rate of about 3 mL/min, to a person suffering from age-related macular degeneration. The verteporphin (7.5 mL of 2 mg/mL reconstituted solution, available as Visudyne® from Novartis) is diluted with 5% dextrose to a volume of 30 mL using a sufficient quantity of the reconstituted verteporphin so that the total dose injected is about 6 mg/m$^2$ of body surface.

About 15 minutes after the start of the 10 minute infusion of verteporphin, the verteporphin is activated by illuminating the retina with a red light emitting OLED device as set forth in Example 13.

After treatment, the patient's vision is anticipated to be stabilized. The treatment is repeated as needed.

Example 17

Verteporphin is intravenously injected, over a period of about 10 minute at a rate of about 3 mL/min, to a person suffering from pathological myopia. The verteporphin (7.5 mL of 2 mg/mL reconstituted solution, available as Visudyne® from Novartis) is diluted with 5% dextrose to a volume of 30 mL using a sufficient quantity of the reconstituted verteporphin so that the total dose injected is about 6 mg/m$^2$ of body surface.

About 15 minutes after the start of the 10 minute infusion of verteporphin, the verteporphin is activated by illuminating the retina with a red light emitting OLED device as set forth in Example 13.

After treatment, the patient's vision is anticipated to be stabilized. The treatment is repeated as needed.

Example 18

Verteporphin is intravenously injected, over a period of about 10 minutes at a rate of about 3 mL/min, to a person suffering from presumed ocular histoplasmosis. The verteporphin (7.5 mL of 2 mg/mL reconstituted solution, available as Visudyne® from Novartis) is diluted with 5% dextrose to a volume of 30 mL using a sufficient quantity of the reconstituted verteporphin so that the total dose injected is about 6 mg/m$^2$ of body surface.

About 15 minutes after the start of the 10 minute infusion of verteporphin, the verteporphin is activated by illuminating the retina with a red light emitting OLED device as set forth in Example 13.

After treatment, the patient's vision is anticipated to be stabilized. The treatment is repeated as needed.

Example 19

Figure 8:
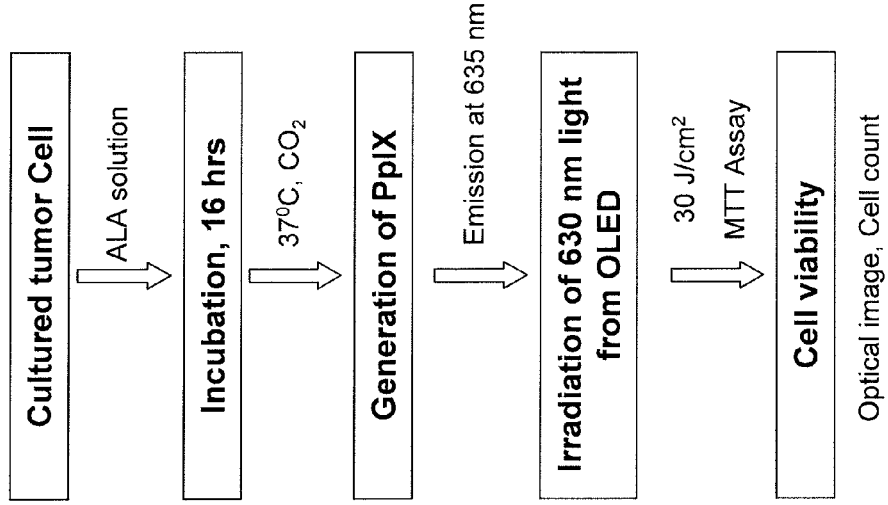
FIG. 8 is a schematic diagram of an in vitro efficacy study with typical tumor cells.

An efficacy study has been performed with 5-aminolevulinic acid (ALA) and CHO-K1 (Chinese Hamster Ovarian Cancer, ATCC, CRL-2243) cell line. FIG. 8 exhibits the efficacy study scheme. Cells were cultured in a 96-well media (Hyclone F-12K medium and dulbecco phosphate buffer saline, DPBS) and incubated at 37° C. under CO$_2$ atmosphere for about 16 hrs. The cells were then calibrated by cell counting with a standard cross area under optical microscope (Olympus IX-70) to establish a base reference number of cells about 10,000 counts in 100 uL medium per well plate. ALA solutions (0.84 mg/mL~3.3 mg/mL in F-12K medium) with two different concentrations as 1 mM, and 2 mM were introduced into same media as mentioned above and incubated for about 16 hrs at 37° C. under CO$_2$ atmosphere. While not being limited by theory, it is believed that in this process, ALA undergoes a biological transformation and is converted to protoporphyrin IX (PpIX). The generation of PpIX was confirmed by fluorescence emission at 635 nm.

Figure 9B:
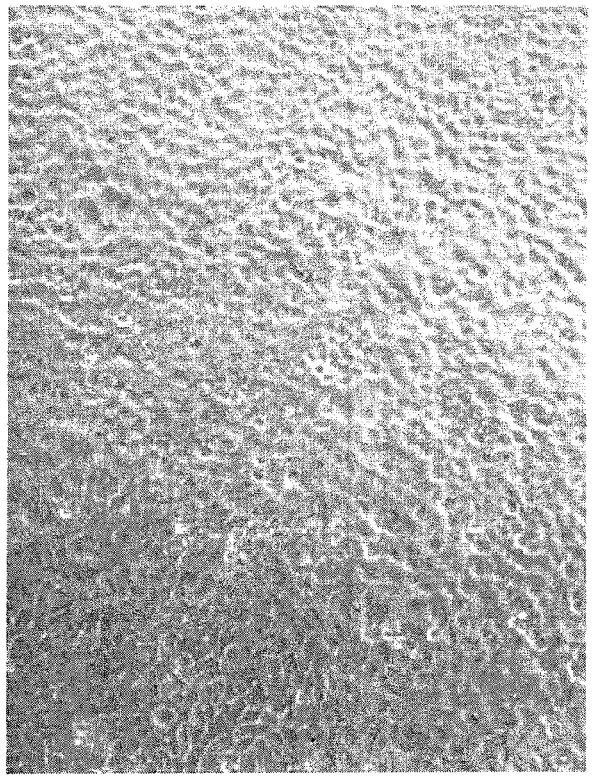
FIG. 9B shows optical microscope images of ALA treated CHO-K1 cells after 30 $J/cm^2$ irradiation with an embodiment of a light-emitting device.
Figure 9A:
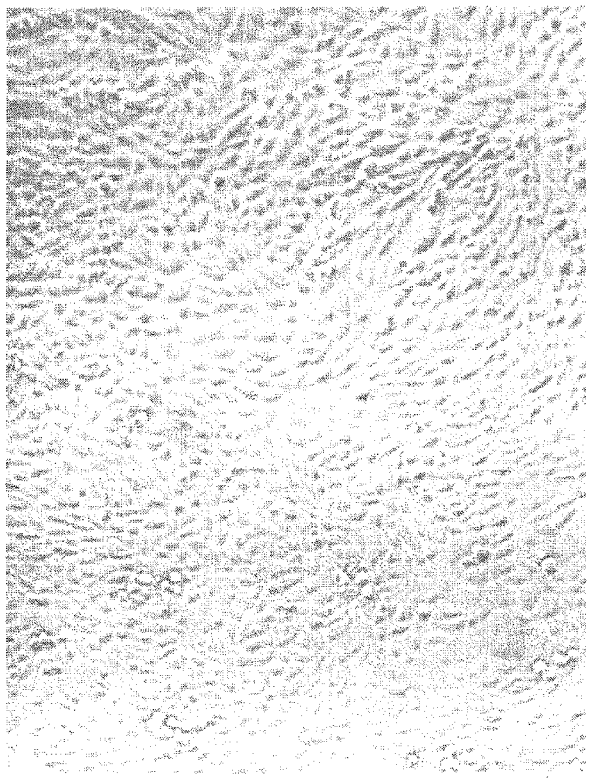
FIG. 9A shows optical microscope images of untreated CHO-K1 cells.

An OLED was constructed as described in Example 13 (emissive layer comprising Compound 2:Ir(piq)$_2$acac). The cells were then irradiated with red light (630 nm) from the OLED with a total dose of 30 J/cm$^2$. While not being limited by theory, it is believed PpIX absorbs 630 nm light and is excited to its singlet state followed by intersystem crossing to triplet state. Since the triplet state has longer lifetime, the triplet PpIX interacts with molecular oxygen and generates singlet oxygen and other reactive oxygen species (ROS). These ROS have short lifetime, and thus diffuse only about several tens of nm before reacting with different cell components such as cell membrane, mitocondria, lissome, golgy bodies, nucleus etc. This destroys the cell components, and thus kills the tumor cell. Optical microscope (Olympus IX-70) images of the cells after 30 J/cm² red light irradiation shows (FIG. 9) that the healthy leafy type cells (FIG. 9A) transforms to droplet type (FIG. 9B) upon light irradiation indicating significant cell death.

Figure 10:
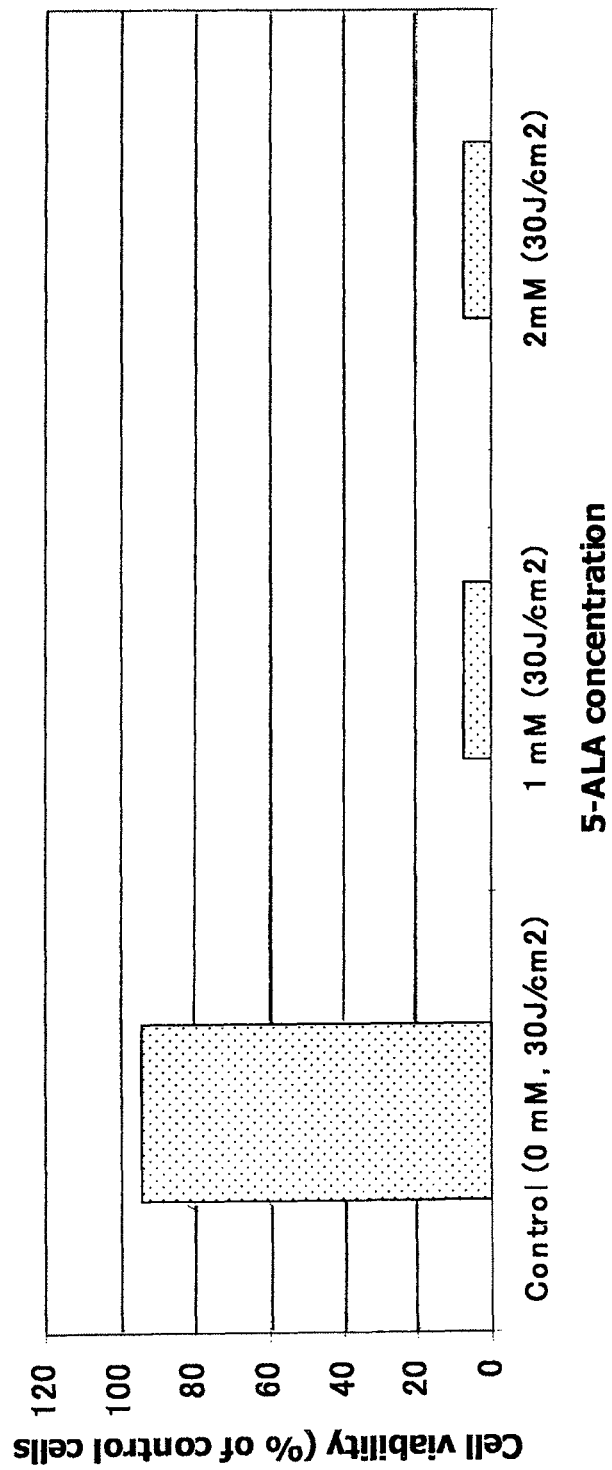
FIG. 10 is a graph depicting cell viability vs. 5-ALA concentrations

Followed by light irradiation, 10 uL of MTT solution (Invitrogen, 3,(4,5-dimethylthiazol-2-yl)-2,5-diphenyl tetrazolium bromide, 5 mg/mL in DPBS) was added to each well including the control well and shaken well to mix completely. The wells were incubated (37° C., 5% $CO_2$) for about 1.5 hrs to generate purple crystals. Then 100 uL MTT solubilization solution were added to each well and incubated (37° C., 5% $CO_2$) for about 16 hrs to dissolve the purple crystals. Finally the absorbance of the cells at about 570 nm with a reference wavelength at 690 nm were recorded by a microplate reader (BioTeK MQX-200) in order to estimate cell viability (%). Cell viability results are shown in FIG. 10. FIG. 10 shows that at the concentrations of ALA applied, of about 1 mM or higher, cell death was about 90% or higher at a near-IR light dose of 30 J/cm². The reference cells were irradiated with same dose of light but without ALA. For a better comparison identical cells were kept at normal environment without light irradiation and compared with reference.

Although the claims have been explained in the context of certain preferred embodiments and examples, it will be understood by those skilled in the art that the present claims extends beyond the specifically disclosed embodiments to other alternative embodiments and/or uses and obvious modifications and equivalents thereof. Thus, it is intended that the scope of the present claims should not be limited by the particular disclosed embodiments described above.

What is claimed is:

1. A compound represented by Formula 2:

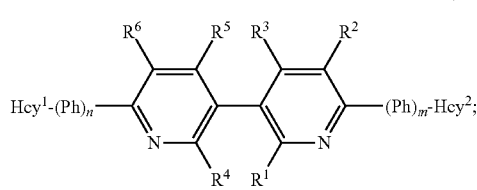

(Formula 2)

wherein each Ph is independently optionally substituted phenyl;
n and m are independently 0, 1, or 2;
$Hcy^1$ is optionally substituted carbazolyl, optionally substituted diphenylamine, optionally substituted benzimidazolyl, optionally substituted benzothiazolyl, or optionally substituted benzoxazolyl;
$Hcy^2$ is optionally substituted benzimidazolyl, optionally substituted benzothiazolyl, or optionally substituted benzoxazolyl; and
$R^1$, $R^2$, $R^3$, $R^4$, $R^5$, and $R^6$ are independently selected from the group consisting of H, optionally substituted $C_{1-12}$ alkyl, and optionally substituted phenyl.

2. The compound of claim 1, wherein $R^1$, $R^2$, $R^3$, $R^4$, $R^5$, and $R^6$ are H.

3. The compound of claim 1, wherein n is 1 and m is 0.

4. The compound of claim 1, further represented by Formula 4:

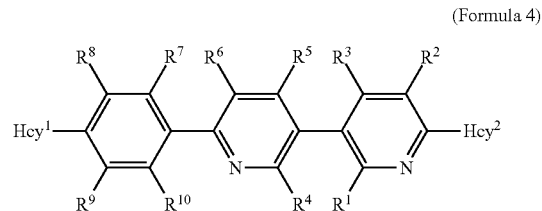

(Formula 4)

wherein $R^1$, $R^2$, $R^3$, $R^4$, $R^5$, $R^6$, $R^7$, $R^8$, $R^9$, and $R^{10}$ are independently selected from the group consisting of H, optionally substituted $C_{1-12}$ alkyl, and optionally substituted phenyl.

5. The compound of claim 4, wherein $R^1$, $R^2$, $R^3$, $R^4$, $R^5$, $R^6$, $R^7$, $R^8$, $R^9$, and $R^{10}$ are H.

6. The compound of claim 1, further represented by Formula 5:

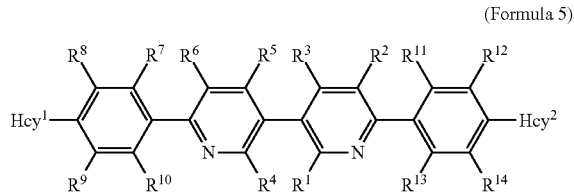

(Formula 5)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ are independently selected from the group consisting of H, optionally substituted $C_{1-12}$ alkyl, and optionally substituted phenyl.

7. The compound of claim 6, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ are H.

8. The compound of claim 1, further represented by Formula 8:

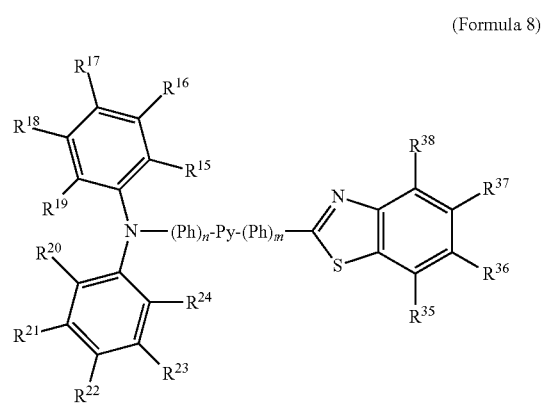

(Formula 8)

wherein Py is

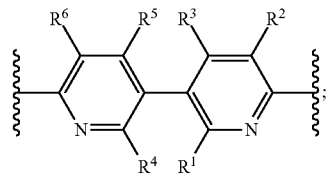

and $R^1, R^2, R^3, R^4, R^5, R^6, R^{15}, R^{16}, R^{17}, R^{18}, R^{19}, R^{20}, R^{21}, R^{22}, R^{23}, R^{24}, R^{35}, R^{36}, R^{37}$, and $R^{38}$ are independently selected from the group consisting of H, optionally substituted $C_{1-12}$ alkyl, and optionally substituted phenyl.

9. The compound of claim 8, wherein $R^{15}, R^{16}, R^{17}, R^{18}, R^{19}, R^{20}, R^{21}, R^{22}, R^{23}, R^{24}, R^{35}, R^{36}, R^{37}$, and $R^{38}$ are H.

10. The compound of claim 1, further represented by Formula 9:

(Formula 9)

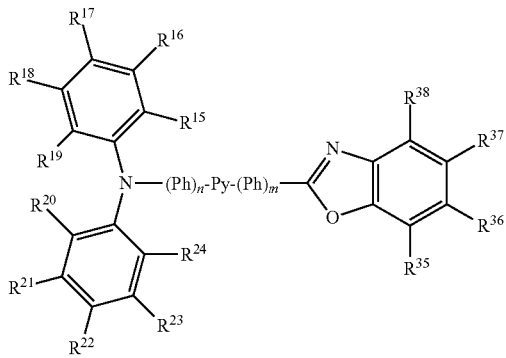

wherein Py is

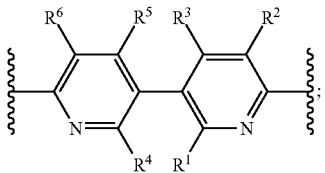

and $R^1, R^2, R^3, R^4, R^5, R^6, R^{15}, R^{16}, R^{17}, R^{18}, R^{19}, R^{20}, R^{21}, R^{22}, R^{23}, R^{24}, R^{35}, R^{36}, R^{37}$, and $R^{38}$ are independently selected from the group consisting of H, optionally substituted $C_{1-12}$ alkyl, and optionally substituted phenyl.

11. The compound of claim 10, wherein $R^{15}, R^{16}, R^{17}, R^{18}, R^{19}, R^{20}, R^{21}, R^{22}, R^{23}, R^{24}, R^{35}, R^{36}$, and $R^{38}$ are H.

12. The compound of claim 1, further represented by Formula 10:

(Formula 10)

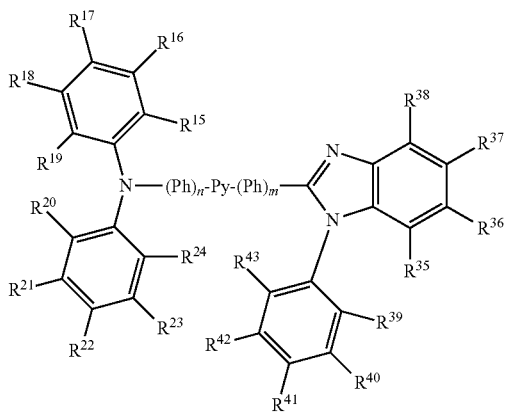

wherein Py is

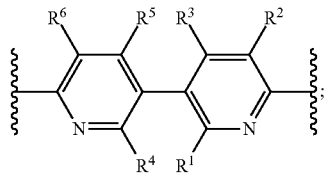

and $R^1, R^2, R^3, R^4, R^5, R^6, R^{15}, R^{16}, R^{17}, R^{18}, R^{19}, R^{20}, R^{21}, R^{22}, R^{23}, R^{24}, R^{35}, R^{36}, R^{37}, R^{38}, R^{39}, R^{40}, R^{41}, R^{42}$, and $R^{43}$ are independently selected from the group consisting of H, optionally substituted $C_{1-12}$ alkyl, and optionally substituted phenyl.

13. The compound of claim 12, wherein $R^{15}, R^{16}, R^{17}, R^{18}, R^{19}, R^{20}, R^{21}, R^{22}, R^{23}, R^{24}, R^{35}, R^{36}, R^{37}, R^{38}, R^{39}, R^{40}, R^{41}, R^{42}$, and $R^{43}$ are H.

14. The compound of claim 1, further represented by Formula 11:

(Formula 11)

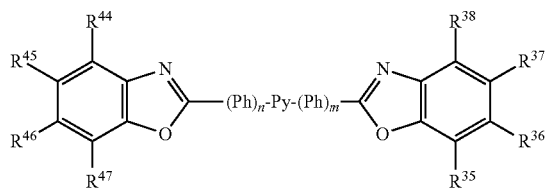

wherein Py is

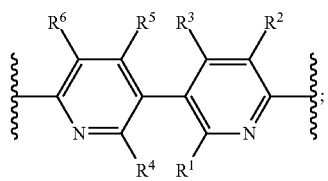

and $R^1, R^2, R^3, R^4, R^5, R^6, R^{35}, R^{36}, R^{37}, R^{38}, R^{44}, R^{45}, R^{46}$, and $R^{47}$ are independently selected from the group consisting of H, optionally substituted $C_{1-12}$ alkyl, and optionally substituted phenyl.

15. The compound of claim 14, wherein $R^{35}, R^{36}, R^{37}, R^{38}, R^{44}, R^{45}, R^{46}$, and $R^{47}$ are H.

16. The compound of claim 1, further represented by Formula 12:

(Formula 12)

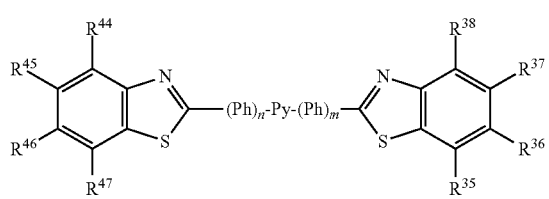

wherein Py is

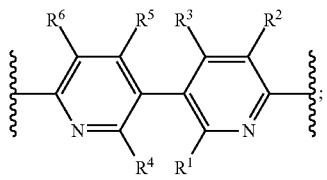

and

R$^1$, R$^2$, R$^3$, R$^4$, R$^5$, R$^6$, R$^{35}$, R$^{36}$, R$^{37}$, R$^{38}$, R$^{44}$, R$^{45}$, R$^{46}$, and R$^{47}$ are independently selected from the group consisting of H, optionally substituted C$_{1-12}$ alkyl, and optionally substituted phenyl.

17. The compound of claim 16, wherein R$^{35}$, R$^{36}$, R$^{37}$, R$^{38}$, R$^{44}$, R$^{45}$, R$^{46}$, and R$^{47}$ are H.

18. The compound of claim 1, further represented by Formula 13:

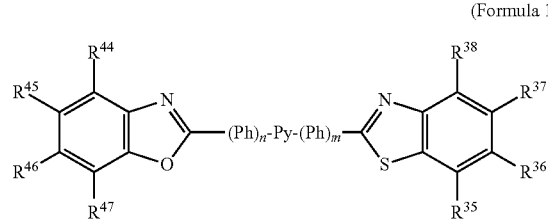
(Formula 13)

wherein Py is

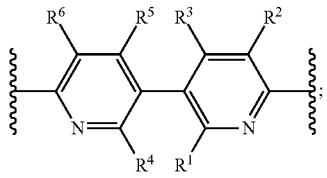

and

R$^1$, R$^2$, R$^3$, R$^4$, R$^5$, R$^6$, R$^{35}$, R$^{36}$, R$^{37}$, R$^{38}$, R$^{44}$, R$^{45}$, R$^{46}$, and R$^{47}$ are independently selected from the group consisting of H, optionally substituted C$_{1-12}$ alkyl, and optionally substituted phenyl.

19. The compound of claim 18, wherein R$^{35}$, R$^{36}$, R$^{37}$, R$^{38}$, R$^{44}$, R$^{45}$, R$^{46}$, and R$^{47}$ are H.

20. A compound represented by Formula 29:

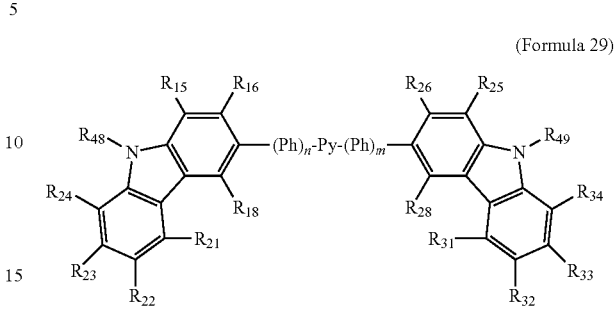
(Formula 29)

wherein Py is

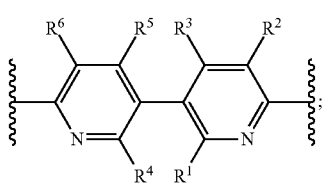

wherein each Ph is independently optionally substituted phenyl;

n and m are independently 0, 1, or 2; and

R$^1$, R$^2$, R$^3$, R$^4$, R$^5$, R$^6$, R$^{15}$, R$^{16}$, R$^{18}$, R$^{21}$, R$^{22}$, R$^{23}$, R$^{24}$, R$^{25}$, R$^{26}$, R$^{28}$, R$^{31}$, R$^{32}$, R$^{33}$, R$^{34}$, R$^{48}$, and R$^{49}$ are independently selected from the group consisting of H, optionally substituted C$_{1-12}$ alkyl, and optionally substituted phenyl.

21. The compound of claim 20, further represented by Formula 30:

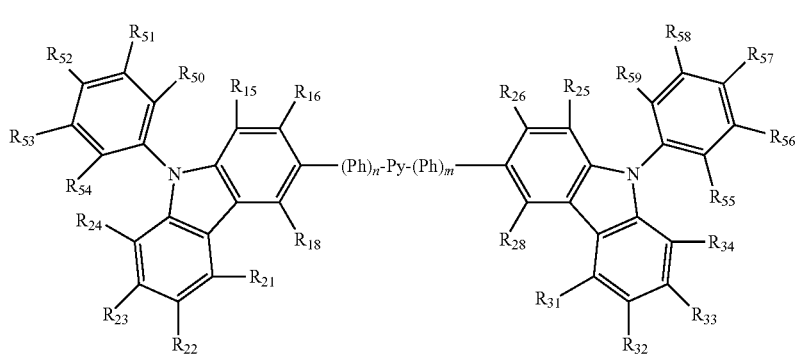
(Formula 30)

wherein R$^{50}$, R$^{51}$, R$^{52}$, R$^{53}$, R$^{54}$, R$^{55}$, R$^{56}$, R$^{57}$, R$^{58}$, and R$^{59}$ are independently selected from the group consisting of H, optionally substituted C$_{1-12}$ alkyl, and optionally substituted phenyl.

22. The compound of claim 1, selected from the group consisting of:

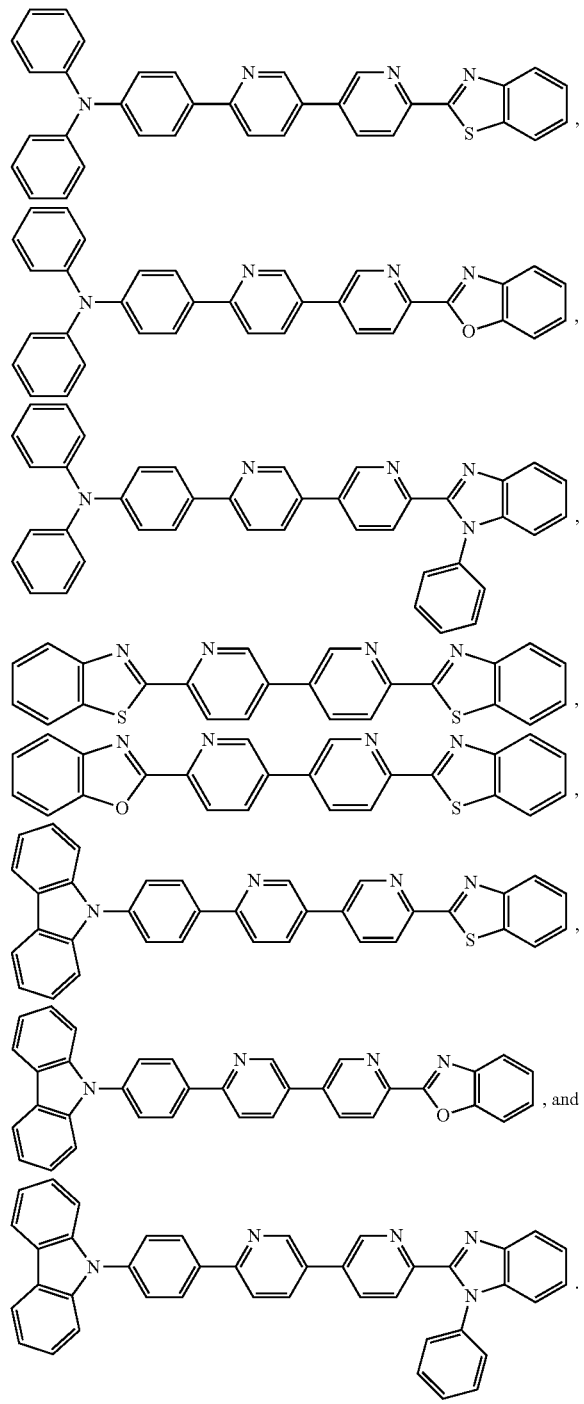

23. An organic light-emitting device comprising an organic component disposed between an anode and a cathode, wherein the organic component comprises a light-emitting component and a compound according to claim 1.

24. The device of claim 23, wherein the organic component further comprises a light-emitting layer comprising the light-emitting component.

25. The device of claim 23, wherein the organic component further comprises at least one layer comprising the compound, wherein the layer is selected from: an electron-transport layer, an electron-injecting layer, and an electron-injecting and electron-transport layer.

26. A composition comprising a compound according to claim 1 and fluorescent compound or a phosphorescent compound.

27. The composition of claim 26, wherein the fluorescent compound or phosphorescent compound is selected from the group consisting of: bis-{2-[3,5-bis(trifluoromethyl)phenyl]pyridinato-N,C2'}iridium(III)-picolinate, bis(2-[4,6-difluorophenyl]pyridinato-N,C2')iridium (III) picolinate, bis(2-[4,6-difluorophenyl]pyridinato-N, C2')iridium (acetylacetonate), Iridium (III) bis(4,6-difluorophenylpyridinato)-3-(trifluoromethyl)-5-(pyridine-2-yl)-1,2,4-triazolate, Iridium (III) bis(4,6-difluorophenylpyridinato)-5-(pyridine-2-yl)-1H-tetrazolate, bis[2-(4,6-difluorophenyl)pyridinato-N,C$^{2'}$]iridium(III)tetra (1-pyrazolyl)borate, Bis[2-(2'-benzothienyl)-pyridinato-N,C3']iridium (III)(acetylacetonate), Bis[(2-phenylquinolyl)-N,C2']iridium (III) (acetylacetonate), Bis[(1-phenylisoquinolinato-N,C2')]iridium (III) (acetylacetonate), Bis[(dibenzo[f,h]quinoxalino-N,C2')iridium (III)(acetylacetonate), Tris(2,5-bis-2'-(9',9'-dihexylfluorene)pyridine)iridium (III), Tris[1-phenylisoquinolinato-N,C2']iridium (III), Tris-[2-(2'-benzothienyl)-pyridinato-N,C3']iridium (III), Tris[1-thiophen-2-ylisoquinolinato-N,C3']iridium (III), Tris[1-(9,9-dimethyl-9H-fluoren-2-yl)isoquinolinato-(N,C3')iridium (III)), Bis(2-phenylpyridinato-N,C2')iridium(III) (acetylacetonate) [Ir(ppy)$_2$(acac)], Bis(2-(4-tolyl)pyridinato-N,C2')iridium(III)(acetylacetonate) [Ir(mppy)$_2$(acac)], Bis(2-(4-tert-butyl)pyridinato-N,C2')iridium (III) (acetylacetonate) [Ir(t-Buppy)$_2$(acac)], Tris(2-phenylpyridinato-N,C2')iridium (III) [Ir(ppy)$_3$], Bis(2-phenyloxazolinato-N,C2')iridium (III) (acetylacetonate) [Ir(op)$_2$(acac)], Tris(2-(4-tolyl)pyridinato-N,C2')iridium(III) [Ir(mppy)$_3$], Bis[2-phenylbenzothiazolato-N,C2']iridium (III)(acetylacetonate), Bis[2-(4-tert-butylphenyl)benzothiazolato-N,C2']iridium(III)(acetylacetonate), Bis[(2-(2'-thienyl)pyridinato-N,C3')]iridium (III) (acetylacetonate), Tris[2-(9,9-dimethylfluoren-2-yl)pyridinato-(N,C3')]iridium (III), Tris[2-(9,9-dimethylfluoren-2-yl)pyridinato-(N,C3')]iridium (III), Bis[5-trifluoromethyl-2-[3-(N-phenylcarbzolyl)pyridinato-N,C2']iridium(III)(acetylacetonate), (2-PhPyCz)$_2$Ir(III)(acac), and combinations thereof.

28. A method of carrying out phototherapy comprising:
exposing at least a portion of a tissue of a mammal to light from a device of claim 23.

29. The method of claim 28, further comprising administering a photosensitive compound to the tissue, and wherein at least a portion of the photosensitive compound is activated by exposing the portion of the tissue to light from the device.

30. A method of treating a disease, comprising:
administering a photosensitive compound to a tissue of a mammal in need thereof;
exposing at least a portion of the tissue to light from a device of claim 23; and
wherein at least a portion of the photosensitive compound is activated by at least a portion of the light from the device to which the tissue is exposed, to thereby treat the disease.

31. The method of claim 30, wherein activating the photosensitive compound produces singlet oxygen.

32. The method of claim 30, wherein the photosensitive compound is 5-aminolevulinic acid, verteporfin, zinc phthalocyanine, or pharmaceutically acceptable salts thereof.

33. The method of claim 30, wherein the disease is cancer.

34. The method of claim 30, wherein the disease is a microbial infection.

35. The method of claim 30, wherein the disease is a skin condition.

36. The method of claim 30, wherein the disease is an eye condition.

37. A phototherapy system comprising:
a device according to claim 23; and
a photosensitive compound;
wherein the photosensitive compound is suitable for administration to a tissue of a mammal in need of phototherapy; and
wherein the device is configured to emit light of a wavelength which can activate at least a portion of the photosensitive compound when it is in the tissue.

38. The compound of claim 20, represented by the following formula:

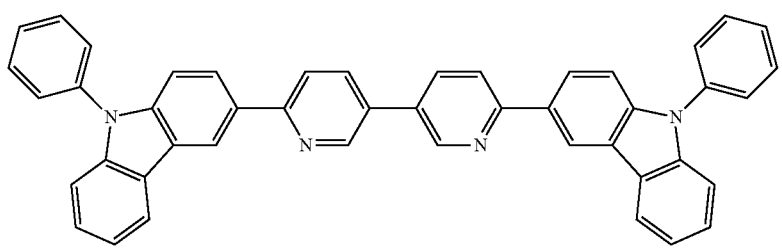 [SMILES: c1ccc(-n2c3ccccc3c3cc(-c4ccc(-c5ccc(-c6ccc7c(c6)c6ccccc6n7-c6ccccc6)nc5)cn4)ccc32)cc1]

* * * * *